United States Patent
Reddy et al.

(10) Patent No.: US 7,214,668 B2
(45) Date of Patent: May 8, 2007

(54) PHOSPHONIC ACID BASED PRODRUGS OF PMEA AND ITS ANALOGUES

(75) Inventors: K. Raja Reddy, San Diego, CA (US);
Mark D. Erion, Del Mar, CA (US);
Michael C. Matelich, San Diego, CA (US); Joseph J. Kopcho, San Diego, CA (US)

(73) Assignee: Metabasis Therapeutics, Inc., La Jolla, CA (US)

( * ) Notice: Subject to any disclaimer, the term of this patent is extended or adjusted under 35 U.S.C. 154(b) by 0 days.

(21) Appl. No.: 10/436,922

(22) Filed: May 12, 2003

(65) Prior Publication Data
US 2003/0229225 A1 Dec. 11, 2003

Related U.S. Application Data

(60) Provisional application No. 60/380,545, filed on May 13, 2002.

(51) Int. Cl.
C07F 9/6574 (2006.01)
A61K 31/675 (2006.01)
A61P 31/20 (2006.01)
A61P 31/14 (2006.01)
A61P 35/00 (2006.01)

(52) U.S. Cl. ......................... 514/81; 544/244
(58) Field of Classification Search ................ 544/244; 514/81
See application file for complete search history.

(56) References Cited

U.S. PATENT DOCUMENTS

| | | | |
|---|---|---|---|
| 3,018,302 | A | 1/1962 | Bielefeld et al. |
| 4,659,825 | A | 4/1987 | Holy et al. |
| 4,724,233 | A | 2/1988 | De Clercq et al. |
| 4,808,716 | A | 2/1989 | Holy et al. |
| 4,952,740 | A | 8/1990 | Juge et al. |
| 5,130,427 | A | 7/1992 | Alexander et al. |
| 5,142,051 | A | 8/1992 | Holy et al. |
| 5,157,027 | A | 10/1992 | Biller et al. |
| 5,514,798 | A | 5/1996 | Bischofberger et al. |
| 5,658,889 | A | 8/1997 | Gruber et al. |
| 5,665,386 | A | 9/1997 | Benet et al. |
| 5,686,629 | A | 11/1997 | Bischofberger et al. |
| 5,716,928 | A | 2/1998 | Benet et al. |
| 5,962,440 | A | 10/1999 | Sulsky |
| 5,962,522 | A | 10/1999 | Wacher et al. |
| 6,004,927 | A | 12/1999 | Benet et al. |
| 6,028,054 | A | 2/2000 | Benet et al. |
| 6,037,335 | A | 3/2000 | Takashima et al. |
| 6,054,587 | A | 4/2000 | Reddy et al. |
| 6,110,903 | A | 8/2000 | Kasibhatla et al. |
| 6,121,234 | A | 9/2000 | Benet et al. |
| 6,180,666 | B1 | 1/2001 | Wacher et al. |
| 6,284,748 | B1 | 9/2001 | Dang et al. |
| 6,294,672 | B1 | 9/2001 | Reddy et al. |
| 6,312,662 | B1 * | 11/2001 | Erion et al. ............... 424/9.1 |
| 6,399,782 | B1 | 6/2002 | Kasibhatla et al. |
| 6,489,476 | B1 | 12/2002 | Dang et al. |
| 6,752,981 | B1 * | 6/2004 | Erion et al. ............... 424/9.1 |
| 6,946,115 | B2 | 9/2005 | Erion et al. |
| 2003/0225277 | A1 * | 12/2003 | Kopcho et al. ............ 544/244 |
| 2003/0229225 | A1 | 12/2003 | Reddy et al. |
| 2004/0092476 | A1 | 5/2004 | Erion et al. |

(Continued)

FOREIGN PATENT DOCUMENTS

EP 0161955 A1 11/1985

(Continued)

OTHER PUBLICATIONS

March, Advanced Organic Chemistry: Reactions, Mechanisms, and Structures, McGraw Hill Book Company, New York, NY (1968) pp. 87-88.*

(Continued)

*Primary Examiner*—Mark L. Berch
(74) *Attorney, Agent, or Firm*—Sterne, Kessler, Goldstein & Fox P.L.L.C.

(57) ABSTRACT

Prodrugs of Formula I, their uses, their intermediates, and their method of manufacture are described:

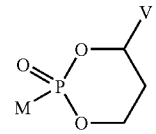

Formula 1 wherein:
M and V are cis to one another and $MPO_3H_2$ is a phosphonic acid selected from the group consisting of 9-(2-phosphonylmethoxyethyl)adenine, (R)-9-(2-phosphonylmethoxy propyl)adenine, 9-(2-phosphonylmethoxyethyl)guanine, 9-(2-phosphonylmethoxy ethyloxy)adenine, 9-(2-phosphonylmethoxyethyl)-2,6-diaminopurine, (S)-1-(3-hydroxy-2-phosphonylmethoxypropyl)cytosine, (S)-9-(3-hydroxy-2-phosphonylmethoxypropyl)adenine, 9-(3-hydroxy-2-phosphonylmethoxypropyl)guanine, and (S)-9-(3-fluoro-2-phosphonyl methoxypropyl)adenine;
V is selected from a group consisting of phenyl, 2-pyridyl, 3-pyridyl, 4-pyridyl, 2-furanyl, 3-furanyl, 2-thienyl, and 3-thienyl, all optionally substituted with 1-3 substituents selected from a group consisting of F, Cl, Br, C1-C3 alkyl, $CF_3$ and $OR^6$;
$R^6$ is selected from the group consisting of C1-C3 alkyl, and $CF_3$;
and pharmaceutically acceptable salts thereof.

30 Claims, 8 Drawing Sheets

U.S. PATENT DOCUMENTS

| | | | |
|---|---|---|---|
| 2004/0192651 A1 | 9/2004 | Boyer et al. | |
| 2005/0282782 A1* | 12/2005 | Martin | 514/81 |
| 2005/0288240 A1 | 12/2005 | Erion et al. | |
| 2006/0030545 A1* | 2/2006 | Cheng et al. | 514/81 |
| 2006/0046981 A1* | 3/2006 | Shibata | 514/81 |

FOREIGN PATENT DOCUMENTS

| | | |
|---|---|---|
| EP | 0180276 A1 | 5/1986 |
| EP | 0338372 A2 | 10/1989 |
| EP | 0 481 214 B1 | 9/1991 |
| EP | 0632048 A1 | 1/1995 |
| EP | 0353692 B1 | 10/1995 |
| WO | WO 93/19075 | 9/1993 |
| WO | WO 95/07920 | 3/1995 |
| WO | WO 96/01267 A1 | 1/1996 |
| WO | WO 91/19721 A1 | 12/1996 |
| WO | WO 97/03679 A1 | 2/1997 |
| WO | WO 98/39342 | 9/1998 |
| WO | WO 98/39343 | 9/1998 |
| WO | WO 98/39344 | 9/1998 |
| WO | WO 99/04774 A2 | 2/1999 |
| WO | WO 00/38666 | 7/2000 |
| WO | WO 00/52015 A2 | 9/2000 |
| WO | WO 02/08241 A2 | 1/2002 |

OTHER PUBLICATIONS

Wacher, V.J., et al., Advanced Drug Delivery Reviews 46:89-102 (2001).*

Wacher, et al., "Active Secretion and Enterocytic Drug Metabolism Barriers to Drug Absorption," *Adv. Drug Del. Rev.*, 46:89-102 (2001).

Yamamoto, et al., "Synthesis of Pyridine N-Oxide-SbCl5 Complexes and Their Intrmolecular and Oxygen-Transfer Reaction," *Tetrahedron Lett.*, 37:1871-3 (1981).

Phillion, et al., "Synthesis and Reactivity of Diethyl Phosphonomethyltriflate," *Tetrahedron Lett.*, 27(13):1477-80 (1986).

Quast, et al., "Herstellung von Methylphosphonsaure-dichlorid," *Synthesis*, 490 (1974).

Ramachandran, et al., "Efficient General Synthesis of 1,2- and 1,3-Diols in High Enantiomeric Excess via the Intramolecular Asymmetric Reduction of the Corresponding Ketoalkyl Diisopinocampheylborinate Intermediates," *Tetrahedron Lett.*, 38(5):761-4 (1997).

Russell, et al., "Determination of 9-[(2-phosphonylmethoxy)ethyl]adenine in rat urine by high-performance liquid chromatography with fluorescence detection," *J Chromatogr.*, 572(1-2):321-6 (1991).

Sakamoto, et al., "The Palladium-Catalyzed Arylation of 4H-1,3-Dioxin," *Tetrahedron Lett.*, 33(45):6845-8 (1992).

Serafinowska, et al., "Synthesis and in Vivo Evaluation of Prodrugs of 9-[2—(Phosphonomethoxy)ethoxy]adenine," *J. Med. Chem.*, 38:1372-9 (1995).

Shaw, et al., "Pharmacokinextics and Metabolism of Selected Prodrugs of PMEA in Rats," *Drug Metabolism Dis.*, 25(3):362-366 (1997).

Starrett, et al., "Synthesis, oral bioavailability determination, and in vitro evaluation of prodrugs of the antiviral agent 9-[2-(phosphonomethoxy)ethyl]adenine (PMEA)," *J Med Chem.*, 37(12):1857-64 (1994).

Still, et al., "Direct Synthesis of Z-Unsaturated Esters. A Useful Modification of the Horner-Emmons Olefination," *Tetrahedron Lett.*, 24(41):4405-8 (1983).

Stowell, et al., "The Mild Preparation of Synthetically Useful Phosphonic Dichlorides: Application to the Synthesis of Cyclic Phosphonic Diesters and Diamides," *Tetrahedron Lett.*, 31(23):3261-2 (1990).

Tawfik, et al., "1,8-Diazabicyclo[5.4.0]undecene Mediated Transesterification of p-Nitrophenyl Phosphonates: A Novel Route to Phosphono Esters," *Synthesis*, 968-72 (1993).

Turner, "A General Approach to the Synthesis of 1,6-, 1,7-, and 1,8-Naphthyridines," *J. Org. Chem.*, 55:4744-50 (1990).

Turner, et al., "Acylation off Ester Enolates by N-Methoxy-N-methylamides: An Effective Synthesis of β-Keto Ester," *J. Org. Chem.*, 54:4229-31 (1989).

Khamnei, et al., "Neighboring Group Catalysis in the Design of Nucleotide Prodrugs," *J. Med. Chem.*, 39:4109-15 (1996).

Kobayashi, et al., "Acylation of Active Methylene Compounds via Palladium Complex-Catalyzed Carbonylative Cross-Coupling of Organic Halides," *Tetrahedron Lett.*, 27(39):4745-8 (1986).

Mitsunobu, "The Use of Diethyl Azodicarboxylate and Triphenylphosphine in Synthesis and Transformation of Natural Products," *Synthe.*, 1-28 (1981).

Moriarty, et al., "Diphenyl Methylphosphonate as a Phosphonylation Reagent with High Diastereoselectivity at Phosphorus," *Tetrahedron Lett.*, 38(15):2597-600 (1997).

Mukaiyama, "Chapter 3: The Directed Aldol Reaction," *Org. React.*, 28:203-331 (1982).

Mulato, et al., "Nonsteroidal Anti-Inflammatory Drugs Effeciently Reduce the Transport and Cytotoxicity of Adefovir Mediated by the Human Renal Organic Anion Transporter 1," *J. Pharm. Exp. Ther.*, 295:10-15 (2001).

Murono, et al., "Prevention and inhibition of nasopharyngeal carcinoma growth by antiviral phosphonated nucleoside analogs," *Cancer Res.*, 61(21):7875-7 (2001).

Naesens, et al., "Therapeutic Potential of HPMPC (Cidofovir), PMEA (Adefovir) and Related Acyclic Nucleoside Phosphonate Analogues as Broad-Spectrum Antiviral Agents," *Nucleosides & Nucleotides*, 16(7-9):983-92 (1997).

Naesens, et al., "HPMPC (cidofovir), PMEA (adefovir) and Related Acyclic Nucleoside Phosphonate Analogues: A Review of Their Pharmacology and Clinical Potential in the Treatment of Viral Infections," *Antiviral Chem. Chemothera.*, 8(1):1-23 (1997).

Noble, et al., "Adefovir Dipivoxil," *Drugs*, 58(3):479-487 (1999).

Chashi, et al., "Synthesis of Phosphonosphingoglycolipid Found in Marine Snail Turbo Cornutus," *Tetrahedron Lett.*, 29(10):1189-92 (1988).

Oliyai, et al., "Kinetic Studies of the Degradation of Oxycarbonyloxymethyl Prodrugs of Adefovir and Tenofovir in Solution," *Nucleosides, Nucleotides & Nucleic Acids*, 20(4-7):1295-1298 (2001).

Patois, et al., "Easy Preparation of Alkylphosphonyl Dichlorides," *Bull. Soc. Chim. Fr.*, 130:485 (1993).

Benzaria, et al., "Synthesis, in Vitro Antiviral Evaluation, and Stability Studies of Bis(S-acyl-2-thioethyl) Ester Derivatives of 9-[2-(Phosphonomethoxy)ethyl]adenine (PMEA) as Potential PMEA Prodrugs with Improved Oral Bioavailability," *J. Med. Chem.*, 39:4958-65 (1996).

Berry, et al., "High-yield preparation of isolated rat liver parenchymal cells: a biochemical and fine structural study," *J Cell Biol.*, 43(3):506-20 (1969).

Bhongle, et al., "Expedient and High-Yield Synthesis of Alkylphosphonyl Dichlorides Under Mild, Neutral Conditions: Reaction of Bis(Trimethylsilyl)Alkyl Phosphonates with Oxalyl Chloride/Dimethylformamide," *Synthetic Comm.*, 17(9):1071-6 (1987).

Bijsterbosch, et al., "Disposition of the acyclic nucleoside phosphonate (S)-9-(3-hydroxy-2-phosphonylmethoxypropyl)adenine," *Antimicrob Agents Chemother* 42(5):1146-50 (1998).

Brechbuhler, et al., "Die Reaktion von Carbonsauren mit Acetalen des N,N-Dimethylformamids: eine Veresterungsmethode," *Helvetica Chimica Acta.*, 48(187):1746-71 (1965).

Bronson, et al., *Nucleotide Analogues as Antiviral Agents*, ACS symposium Series 401, American Chemical Society (1989).

Campagne, et al., "Synthesis of Mixed Phosphonate Diester Analogues of Dipeptides using BOP or PyBOP Reagents," *Tetrahedron Lett.*, 34(42):6743-4 (1993).

Campbell, "The Synthesis of Phosphonate Esters, and Extension of the Mitsunobu Reaction," *J. Org. Chem.*, 57:6331-5 (1992).

Casara, et al., "Synthesis of Acid Stabel 5'-O-Fluoromethyl Phosphonates of Nucleosides. Evaluation as Inhibitors of Reverse Transcriptase," *Bioorg. Med. Chem. Lett.*, 2(2):145-148 (1992).

Chu, et al., "A Regiospecific Synthesis of 1-Methylamino-6-fluoro-7-(4-methylpiperazin-1-yl)-1,4-dihydro-4-oxoquinoline-3-carboxylic Acid," *J. Het. Chem.*, 22:1033-34 (1985).

Chu, et al., "Chemistry and Antiviral Activities of Acyclonucleosides," *J. Het. Chem.*, 23:289-319 (1986).

Coppi, et al., "Lewis Acid Mediated Condensation of Alkenols and Aldehydes. A Selective Synthesis of Tetrahydropyrans and Oxepanes," *J. Org. Chem.*, 53:911-3 (1988).

Cundy, "Clinical pharmacokinetics of the antiviral nucleotide analogues cidofovir and adefovir," *Clin Pharmacokinet.*, 36(2):127-43 (1999).

Cundy, et al., "Oral formulations of adefovir dipivoxil: in vitro dissolution and in vivo bioavailability in dogs," *J Pharm Sci.*, 86(12):1334-8 (1997).

De Clercq, et al., "Antiviral activity of phosphonylmethoxyalkyl derivatives of purine and pyrimidines.," *Antiviral Res.* 8(5-6):261-72 (1987).

De Waziers, et al., "Cytochrome P 450 isoenzymes, Epoxide Hydrolase and Glutathione Transferases in Rat and Human Hepatic and Extrahepatic Tissues," *J. Pharm. Experimental Ther.*, 253(1):387-394 (1990).

Deeks, et al., "The Safety and Efficacy of Adefovir Diplvoxil, a Novel Anti-Human Immunodeficiency Virus (HIV) Therapy, in HIV-Infected Adults: A, Randomized, Double-Blind, Placebo-Controlled Trial," *J. Infect. Dis.*, 176:1517-23 (1997).

Gao, et al., "Asymmetric Synthesis of Both Enantiomers of Tomoxetine and Fluoxetine. Selective Reduction of 2,3-Epoxycinnamyl Alcohol with Red-Al," *J. Org. Chem.*, 53:4081-4 (1988).

Gilead Press Release, "Gilead Achieves Primary Endpoint in Phase III Study of Adefovir Diplvoxil for Chronic Hepatitis B Virus Infection," (2001).

Groen, et al., "Intracellular compartmentation and control of alanine metabolism in rat liver parenchymal cells," *Eur J Biochem.*, 122(1):87-93 (1982).

Harada, et al., "Resolution of 1,3-Alkanediols via Chiral Spiroketals Derived from τ-Menthone," *Tetrahedron Lett.*, 28(41):4843-6 (1987).

Hatse, "Mechanistic study on the cytostatic and tumor cell differentiation-inducing properties of 9-(2-phosphonylmethoxyethyl)adenine (PMEA, adefovir)-collected publications," *Verh K Acad Geneeskd Belg.*, 62(5):373-84 (2000).

Holy, et al., Acyclic nucleotide analogues: synthesis, antiviral activity and inhibitory effects on some cellular and virus-encoded enzymes in vitro, *Antiviral Res.*, 13(6):295-311 (1990).

Inanaga, et al., "A Rapid Esterification by Means of Mixed Anhydride and its Application to Large-Ring Lactonization," *Bull. Chem. Soc. Jpn.*, 52(7):1989-1993 (1979).

Alexander, et al., "Preparation of 9-(2-Phosphonomethoxyethyl)Adenine Esters as Potential Prodrugs," *Collect. Czech. Chem. Commun.*, 59:1853-69 (1994).

Benhamou, et al., "Safety and efficacy of adefovir dipivoxil in patients co-infected with HIV-1 and lamivudine-resistant hepatitis B virus: an open-label pilot study," *Lancet.*, 358(9283):718-23 (2001).

Erion, M.D., et al., "HepDirect Prodrugs for Targeting Nucleotide-Based Antiviral Drugs to the Liver," *Curr. Opin. Invest. Drugs* 7(2):109-117, The Thomson Corporation (2006).

Amin, D., et al., "1-Hydroxy-3-(methylpentylamino)-propylidene-1,1-bisphosphonic Acid as a Potent Inhibitor of Squalene Synthase," *Arzneim.-Forsch/Drug Res.* 46:759-762, Blackwell Publishing, Inc. (1996).

Atiq, O., et al., "Treatment of Unresectable Primary Liver Cancer with Intrahepatic Fluorodeoxyuridine and Mitomycin C Through an Implantable Pump," *Cancer* 69:920-924, John Wiley and Sons, Inc. (1992).

Auberson, Y., et al., "N-Phosphonoalkyl-5-Aminomethylquinoxaline-2,3-Diones: In Vivo Active AMPA and NMDA-(Glycine) Antagonists," *Bioorg. Med. Chem. Lett.* 9:249-254, Elsevier Science Ltd. (1999).

Balthazor, T. and Grabiak, R.C., "Nickel-Catalyzed Arbuzov Reaction: Mechanistic Observations," *J. Org. Chem.* 45:5425-5426, American Chemical Society (1980).

Balzarini, J. et al., "Activity of the (R)-Enantiomers of 9-(2-Phosphonylmethoxypropyl)-Adenine and 9-(2-Phosphonylmethoxypropyl)-2,6-diamiopurine against Human Immunodeficiency Virus in Different Human Cell Systems" *Biochem. and Biophys. Res. Commun.* 219:337-341, Academic Press, Inc. (1996).

Beaucage, S.L. and Iyer, R.P., "The Synthesis of Modified Oligonucleotides by the Phosphoramidite Approach and Their Applications," *Tetrahedron* 49:6123-6194, Pergamon Press Ltd. (1993).

Bespalov, A., et al., "Prolongation of morphine analgesia by competitive NMDA receptor antagonist D-CPPene (SDZ EAA 494) in rats," *Eur. J. Pharmacol.* 351:299-305, Elsevier Science B.V. (1998).

Bird, J., et al., "Synthesis of Novel N-Phosphonoalkyl Dipeptide Inhibitors of Human Collagenase," *J. Med. Chem.* 37:158-169, American Chemical Society (1994).

Borch, R.F. and Millard, J.A., "The Mechanism of Activation of 4-Hydroxycyclophosphamide," *J. Med. Chem.* 30:427-431, American Chemical Society (1987).

Brill, T. and Landon S.J., "Arbuzov-like Dealkylation Reactions of Transition-Metal-Phosphite Complexes," *Chem. Rev.* 84:577-585, American Chemical Society (1984).

Bronson, J.J., et al., "Synthesis and Antiviral Activity of Phosphonylmethoxyethyl Derivatives of Purine and Pyrimidine Bases," in *Nucleotide Analogues as Antiviral Agents, ACS Symposium Series 401*, American Chemical Society (1989).

Bronson, J.J., et al., "Synthesis and Antiviral Activity of Nucleotide Analogues Bearing the (S)-(3-Hydroxy-2-phosphonylmethoxy)propyl Moiety Attached to Adenine, Guanine, and Cytosine," in *Nucleotide Analogues as Antiviral Agents, ACS Symposium Series 401*, American Chemical Society (1989).

Casteel, D. and Peri, S.P., "Steric and Electronic Effects in the Aryl Phosphate to Arylphosphonates Rearrangement," *Synthesis* (9):691-693, Georg Thieme Vertag KG (1991).

Chen, L. and Waxman, D.J., "Intratumoral Activation and Enhanced Chemotherapeutic Effect of Oxazaphosphorines following Cytochrome P-450 Gene Transfer: Development of a Combined Chemotherapy/Cancer Gene Therapy Strategy," *Cancer Res.* 55:581-589, The American Association for Cancer Research (1995).

Chen, L., et al., "Sensitization of Human Breast Cancer Cells to Cyclophosphamide and Ifosfamide by Transfer of a Liver Cytochrome P450 Gene," *Cancer Res.* 56:1331-1340, The American Association for Cancer Research (1996).

Cooper, D.B., et al., "Use of Carbohydrate Derivatives for Studies of Phosphorus Stereochemistry. Part II. Synthesis and Configurational Assignments of 1,-3,2-Oxathiaphosphorinan-2-ones and 1,3,2-Dioxaphosphorinan-2-thiones," *J .Chem. Soc. Perkin I* 3/2422:1049-1052, Royal Society of Chemistry (1974).

Dearfield, K., et al., "Analysis of the genotoxicity of nine acrylate/methacrylate compounds in L5178Y mouse lymphoma cells," *Mutagenesis* 4:381-393, Oxford University Press (1989).

De Clercq, E., et al., "A novel selective broad-spectrum anti-DNA virus agent," *Nature* 323:464-467, Nature Publishing Group (1986).

De Lombaert, S., et al., "Pharmacological Profile of a Non-Peptidic Dual Inhibitor of Neutral Endopeptidase 24.11 and Endothelin-Converting Enzyme," *Biochem. Biophys. Res. Commun.* 204:407-412, Academic Press, Inc. (1994).

De Lombaert, S., et al., "N-Phosphomomethyl Dipeptides and Their Phosphonate Prodrugs a New Generation of Neutral Endopeptidase (NEP, EC 3.4.24.11) Inhibitors," *J. Med. Chem.* 37:498-511, American Chemical Society (1994).

Desos, P., et al., "Structure-Activity Relationships in a Series of 2(1H)-Quinolones Bearing Different Acidic Function in the 3-Position: 6,7-Dichloro-2(1H)-oxoquinoline-3-phosphonic Acid, a New Potent and Selective AMPA/Kainate Antagonists with Neuroprotective Properties," *J. Med. Chem.* 39:197-206, American Chemical Society (1996).

Dickson, J.K., et al., "Orally Active Squalene Synthase Inhibitors: Bis((acyloxy)alkyl) Prodrugs of the α-Phosphonosulfonic Acid Moiety," *J. Med. Chem.* 39:661-664, American Chemical Society (1996).

Edmundson, R.S., et al., "Cyclic Organophosphorous Compounds. Part 23. Configurational Assignments in the 4-Phenyl-1,3,2Λ-dioxaphosphorinane Series. X-Ray Molecular Structure of cis-2-

Benzylamino-4-phenyl-1,3,2-dioxaphosphorinane 2-Oxide," *J. Chem. Research (S)*, 122-123, Science Reviews Ltd. (1989).

Enriquez, P., et al., "Conjugation of Adenine Arabinoside 5'-Monophosphate to Arabinogalactan: Synthesis, Characterization, and Antiviral Activity," *Bioconjugate Chem.* 6:195-202, American Chemical Society (1995).

Erion, M., et al., "Design, Synthesis, and Characterization of a Series of Cytochrome $P_{450}$ 3A-Activated Prodrugs (HepDirect Prodrugs) Useful for Targeting Phosph(on)ate-Based Drugs to the Liver," *J. Am. Chem. Soc.* 126:5154-5163, American Chemical Society (Apr. 2004).

Erion, M., et al., "HepDirect™ Prodrugs: A Novel Strategy for Targeting Drugs to the Liver," *Hepatology* 36:301A, AASLD Abstract No. 551, John Wiley & Sons, Inc. (Oct. 2002).

Erion, M., et al., "Liver-Targeted Drug Delivery Using HepDirect Prodrugs" *J. Pharmacol. Exper. Ther.* 312:554-560, American Society for Pharmacology and Experimental Therapeutics (Feb. 2005).

Erion, M., "Liver-Targeted Nucleoside Prodrugs," presented at the *Gordon Research Conference: Purines, Pyrimidines and Related Substances*, Newport, RI (Jun.-Jul. 2003).

Evans, D.A., et al., "New Procedure for the Direct Generation of Titanium Enolates. Diasteroselective Bond Constructions with Representative Electrophiles," *J. Am. Chem. Soc.* 112:8215-8216, American Chemical Society (1998).

Evans, D.A., et al., "Stereoselective Aldol Reactions of Cholrotitanium Enolates. An Efficient Method of the Assemblage of Polypropionate-Related Synthons," *J. Am. Chem. Soc.* 113:1047, American Chemical Society (1991).

Farquhar, D., et al., "Biologically-Cleavable Phosphate Protective Groups: 4-Acyloxy-1,3,2-Dioxaphosphorinanes as Neutral Latent Precursors of Dianionic Phosphates," *Tetrahedron Lett.* 36:655-658, Elsevier Science Ltd. (1995).

Farquhar, D., et al., "Biologically Reversible Phosphate-Protective Groups," *J. Pharm. Sci.* 72:324-325, American Chemical Society (1983).

Farquhar, D. and Smith, R., "Synthesis and Biological Evaluation of 9-5'-(2-Oxo-1,3,2-oxazaphosphorinan-2-yl)- β -D-arabinosyl) adenine and 9-[5-(2-Oxo-1,3,2-dioxazaphosphorinan-2-yl)- β -D-arabinosyl]adenine: Potential Neutral Precursors of 9-[β-D-Arabinofuranosyl]adenine 5'-Monophosphate," *J. Med. Chem.* 28:1358-1361, American Chemical Society (1985).

Farquhar, D., et al., "5'-4-(Pivaloyloxy)-1,3,2-dioxaphosphorinan-2-yl-2'-deoxy-5-fluorouridine: A Membrane-Permeating Prodrug of 5-Fluoro-2'-deoxyuridylic Acid (FdUMP)," *J. Med. Chem.* 38:488-495, American Chemical Society (1995).

Farquhar, D., et al., "Synthesis and Antitumor Evaluation of Bis[(pivaloyloxy) methyl] 2'-Deoxy-5-fluorouridine 5'-Monophosphate (FdUMP): A Strategy to Introduce Nucleotides into Cells," *J. Med. Chem.* 37:3902-3909, American Chemical Society (1994).

Farquhar, D., et al., "Synthesis and Biological Evaluation of Neutral Derivatives of 5-Fluoro-2'-deoxyuridine 5'-Phosphate," *J. Med. Chem.* 26:1153-1158, American Chemical Society (1983).

Fiume, L., et al., "Inhibition of Hepatitis B Virus Replication by Vidarabine Monophosphate Conjugated with Lactosaminated Serum Albumin," *The Lancet* 2:13-15, The Lancet Publishing Group (1988).

Freed, J.J., et al., "Evidence for Acyloxymethyl Esters of Pyrimidine, 5'-Deoxyribonucleotides as Extracellular Sources of Active 5'-Deoxyribonucleotides in Cultured Cells," *Biochem. Pharm.* 38:3193-3198, Elsevier Inc. (1989).

Friis, G.J. and Bundgaard, H., "Prodrugs of phosphates and phosphonates: Novel lipophilic α-acyloxyalkyl ester derivatives of phosphate- or phosphonate containing drugs masking the negative charges of these groups," *Euro. J. Pharm. Sci.* 4:49-59, Elsevier Science B.V. (1996).

Furegati, S., et al., "Sterochemistry of the Inhibition of α-Chymotrypsin with Optically Active cis-Decaline-Type Organophosphates: $^{31}$P-NMR Studies," *Helvetica Chimica Acta* 81:1127-1138, Wiley-VCH Verlag GmbH & Co. KGaA (1998).

Guida, W.C., et al., "Structure-Based Design of Inhibitors of Purine Nucleoside Phosphorylase. 4. A Study of Phosphate Mimics," *J. Med. Chem.* 37:1109-1114, American Chemical Society (1994).

He, K., et al., "Inactivation of Cytochrome P450 3A4 by Bergamottin, a Component of Grapefruit Juice," *Chem. Res. Toxicol.* 11:252-259, American Chemical Society (1998).

Hillers, S., et al., "Analogs of pyrimidinemono-and polynucleotides. VI. Phosphates of 1-(1,4-dihydroxy-2-pentyl)thymine and 1-(1,3-dihydroxy-2-propyl) uracil," *Chemical Abstracts* 89(17), Chemical Abstracts Service (1978).

Hirayama, N., et al., "Structure and conformation of a novel inhibitor of angiotensin I converting enzyme—a tripeptide containing phosphonic acid," *Int. J. Pept. Protein Res.* 38:20-24, Blackwell Publishing (1991).

Hong, Z. and Lin, C.-C., "Clinical Update of Remofovir (Hepavir B): a Liver-targeting Prodrug of PMEA for the Treatment of Hepatitis B," Presented at the *SRI-Antiviral Drug Discovery & Development Summit*, Mar. 30, 2004.

Hong, Z., "Hepavir B: a Safer and Liver-Targeting Prodrug of PMEA," Presented at the *SRI-Antiviral Drug Discovery & Development Summit*, Ribopharm Inc., Mar. 27, 2003.

Hunston, R., et al., "Synthesis and Biological Properties of Some Cyclic Phosphotriesters Derived from 2'-Deoxy-5-fluorouridine," *J. Med. Chem.* 27:440-444, American Chemical Society (1984).

Jones, S. and Selitsianos, D., "A Simple and Effective Method for Phosphoryl Transfer Using $TiCl_4$ Catalysis" *Org. Lett.* 4:3671-3673, American Chemical Society (published online Sep. 2002).

Keenan, R., et al., "Pathology Reevaluation of the Kociba et al. (1978) Bioassay of 2,3,7,8-TCDD: Implications for Risk Assessment," *J. Tox. Envir. Health* 34:279-296, Hemisphere Publishing Corporation (1991).

Kelley, J.L., et al., "[[(Guaninylalkyl)phosphinico] methyl]phosphonic Acids. Multisubstrate Analogue Inhibitors of Human Erythrocyte Purine Nucleoside Phosphorylase," *J. Med. Chem.* 38:1005-1014, American Chemical Society (1995).

Khorana, H.G., et al., "Cyclic Phosphates. III. Some General Observations on the Formation of Properties of Five-,Six- and Seven-membered Cyclic Phosphate Esters," *J. Am. Chem. Soc.* 79:430-436, American Chemical Society (1957).

Korba, B.A., et al., "Liver-Targeted Antiviral Nucleosides: Enhanced Antiviral Activity of Phosphatidyl-Dideoxyguanosine in Woodchuck Hepatitis Virus Infection In Vivo," *Hepatology* 25:958-963, John Wiley & Sons, Inc. (1996).

Krise, D.P. and Stella, V.J., "Prodrugs of phosphates, phosphonates, and phosphinates," *Adv. Drug. Del. Rev.* 19:287-310, Elsevier Science B.V. (1996).

Kryuchkov, A.A., et al., "Influence of Solvent on the Strength of Cyclic Oxygen-Containing Phosphorus Acids," *Bull. Acad. Sci. USSR, A translation of Izvestiya Akademii Nauk SSSR, Ser. Khim.* 36:1145-1148, Consultants Bureau (1987).

Lau, D., et al., "Safety, Tolerability, Pharmacokinetics and Pharmacodynamics of Remofovir in Chronic HBV Patients in USA and Canada Following Daily Dosing for 28 Days," Presented at the 40th *Annual Meeting of EASL*, Paris, France, *J. Hepatology* 42(Suppl. 2):32, Abstract No. 74, Elsevier Ireland Ltd. (Apr. 2005).

Lefebvre, I., et al., "Mononucleoside Phosphotriester Derivatives with S-Acyl-2-thioethyl Bioreversible Phosphate-Protecting Groups: Intracellular Delivery of 3'-Azido-2',3'-dideoxythymidine 5'-Monophosphate," *J. Med. Chem.* 38:3941-3950, American Chemical Society (1995).

Lin, C.-C., et al., "Development of Hepavir B, A Prodrug of PMEA with Excellenht Liver-Targeting Properties," *Abstracts of the 39*[th] *Annual Meeting of the EASL*, Berlin, Germany, *J. Hepatology* 40:Abstract No. 374, Elsevier Ireland Ltd. (Apr. 2004).

Lin, C.-C., et al., "Pradefovir is a Substrate, but Neither an Inhibitor nor an Inducer for Cytochrome P450," AASLD Abstracts, *Hepatology* 514A:Abstract No. 811, John Wiley & Sons, Inc. (Oct. 2005).

Lin, C.-C., et al., "Remofovir mesylate: a prodrug of PMEA with improved liver-targeting and safety in rats and monkeys," *Antiviral Chem. Chemother.* 15:307-316, International Medical Press (2004).

Lin, C.-C., et al., "Safety, Tolerance, Pharmacokinetics and Pharmacodynamics of Remofovir, A Liver-Targeting Prodrug of PMEA in HBV Patients Following Daily Dosing for 28 Days," AASLD Abstracts, *Hepatology* 40:658A, Abstract No. 1141, John Wiley & Sons, Inc. (Oct. 2004).

Lok, A.S.F., et al., "Neurotoxicity associated with adenine arabinoside monophosphate in the treatment of chronic hepatitis B virus infection," *J. Antimicrob. Chemotherap.* 14:93-99, Oxford University Press (1984).

Lu, X. and Zhu, J., "Palladium-Catalyzed Reaction of Aryl Polyfluoroalkanesulfonates with O,O-Dialkyl Phosphonates," *Synthesis* (8):726-727, Georg Thieme Verlag (1987).

Ludeman, S.M., et al., "Synthesis and Antitumor Activity of Cyclophosphamide Analogues. 4. Preparation, Kinetic Studies, and Anticancer Screening of "Phenylketophosphamide" and Similar Compounds Related to the Cyclophosphamide Metabolite Aldophosphamide," *J. Med. Chem.* 29:716-727, American Chemical Society (1986).

McGuigan, C., et al., "Intracellular Delivery of Bioactive AZT Nucleotides by Aryl Phosphate Derivatives of AZT," *J. Med. Chem.* 36:1048-1052, American Chemical Society (1993).

McGuigan, C., et al., "Kinase Bypass: A New Strategy for Anti-HIV Drug Design," *Bioorg. Med. Chem. Lett.* 3:1207-1210, Pergamon Press Ltd. (1993).

Meier, C., et al., "Cyclic Saligenyl Phosphotriesters of 2',3'-Dideoxy-2',3'-didehydrothymidine (d4T)—A New Pro-Nucleotide Approach -" *Bioorg. Med. Chem. Lett.* 7:99-104, Elsevier Science Ltd. (1997).

Meijer, D.K.F., et al., "Covalent and Noncovalent Protein Binding of Drugs: Implications for Hepatic Clearance, Storage, and Cell-Specific Drug Delivery," *Pharm. Res.* 6:105-118, Plenum Publishing Corporation (1989).

Melvin, L.S., "An Efficient Synthesis of 2-Hydroxyphenylphosphonates," *Tetrahedron Lett.* 22:3375-3376, Pergamon Press Ltd. (1981).

Meyer, R., et al., "2'-O-Acyl-6-thioinosine Cyclic 3',5'-Phosphates as Prodrugs of Thioinosinic Acid," *J. Med. Chem.* 22:811-815, American Chemical Society (1979).

Mitchell, A., et al., "Bioreversible Protection for the Phospho Group: Bioactivation of the Di(4-acyloxybenzyl) and Mono(4-acyloxybenzyl) Phosphoesters of Methylphosphonate and Phosphonacetate," *J. Chem. Soc. Perkin Trans. 1*, 2345-2353, Royal Society of Chemistry (1992).

Moore, M., et al., "Comparison of mutagenicity results for nine compounds evaluated at the hgprt locus in the standard and suspension CHO assays," *Mutagenesis* 6:77-85, Oxford University Press (1991).

Mosbo, J.A. and Verkade, J.G., "Dipole Moment, Nuclear Magnetic Resonance, and Infrared Studies of Phosphorus Configurations and Equalibria in 2-R-2-Oxo-1,3,2-dioxaphosphorinames," *J. Org. Chem.* 42:1549-1555, American Chemical Society (1977).

Murray, G., et al., "Cytochrome P450 CYP3A in human renal cell cancer," *Brit. J. Cancer* 79:1836-1842, Nature Publishing Group (1999).

Murray, G., et al., "Cytochrome P450 Expression Is a Common Molecular Event in Soft Tissue Sarcomas," *J. Pathology* 171:49-52, John Wiley & Sons, Ltd. (1993).

Nakayama, K. and Thompson, W.J., "A Highly Enantioselective Synthesis of Phosphate Triesters," *J. Am. Chem. Soc.* 112:6936-6942, American Chemical Society (1990).

Neidlein, R., et al., "Mild Preparation of 1-Benzyloxyiminoalkylphosphonic Dichlorides: Application to the Synthesis of Cyclic Phosphonic Deisters and Cyclic Monoester Amides," *Heterocycles* 35:1185-1203, Elsevier Science (1993).

Nifantyev, E.E., et al., "Synthesis and Structure of Some Stable Phospholane-Phospholanes," *Phosphorus, Sulfu Silicon and Related Elements* 113:1-13, Taylor & Francis (1996).

Ogg, M., et al., "A reporter gene assay to assess the molecular mechanisms of xenobiotic-dependent induction of the human CYP3A4 gene in vitro," *Xenobiotica* 29:269-279, Taylor & Francis Ltd. (1999).

Ozoe, Y., et al., "Actions of cyclic esters, S-esters, and amides of phenyl-and phenylthiophosphonic acids on mammalia and insect GABA-gated chloride channels," *Bioorg. Med. Chem.* 6:73-83, Elsevier Science Ltd. (1998).

Petrakis, K. and Nagabhushan, T.L., "Palladium-Catalyzed Substitutions of Triflates Derived from Tyrosine-Containing Peptides and Simpler Hydroxyarenes Forming 4-(Diethoxyphosphinyl)phenylalanines and Diethyl Arylphosphonates," *J. Am. Chem. Soc.* 109:2831-2833, American Chemical Society (1987).

Pitcher, H.R., "Built-in Bypass," *Nature* 429:39, Nature Publishing Group (May 2004).

Predvoditelev, D.A., et al., "Glycero-2-Hydroxymethylene Phosphates," *J. Org. Chem. USSR, A Translation of Zhur. Org. Khim.* 13:1489-1492, Plenum Publishing Corporation (1977).

Predvoditelev, D.A., et al., "Synthesis of Lipids and Their Models on the Basis of Glycerol Alkylene Phosphites. V. Cyclic Phosphatidylglycerol and Phosphatidylhydroxyhomocholine," *J. Org. Chem. USSR, A Translation of Zhur. Org. Khim.* 17:1156-1165, Plenum Publishing Corporation (1981).

Prisbe, E.J., et al., "Synthesis and Antiherpes Virus Activity of Phosphate and Phosphonate Derivates of 9-[(1,3-Dihydorxy-2-propoxy)methyl]guanine", *J. Med. Chem.* 29:671-675, American Chemical Society (1986).

Reddy, K.R., et al., "Stereoselective synthesis of nucleoside monophosphate HepDirect™ prodrugs," *Tetrahedron Lett.* 46:4321-4324, Elsevier Ltd. (2005).

Reddy, M.R., et al., "Development of a Quantum Mechanics-Based Free-Energy Perturbation Method: Use in the Calculation of Relative Solvation Free Energies," *J. Am. Chem. Soc.* 126:6224-6225, American Chemical Society (published online Apr. 2004).

Redmore, D., "Phosphorus Derivatives of Nitrogen Heterocycles. 2. Pyridinophosphonic Acid Derivatives," *J. Org. Chem.* 35:4114-4117, American Chemical Society (1970).

Schlachter, S.T., et al., "Anti-Inflammatory/Antiarthritic Ketonic Bisphosphonic Acid Esters," *Bioorg. Med. Chem. Lett.* 8:1093-1096, Elsevier Science Ltd. (1998).

Schultz, C. "Prodrugs of Biologically Active Phosphate Esters" *Bioorganic & Medicinal Chemistry* 11:885-898, Elsevier Science Ltd. (Mar. 2003).

Schultze, L.M. et al., "Practical Synthesis of the anti-HIV Drug, PMPA" *Tetrahedron Lett.* 39:1853-1856, Elsevier Science Ltd. (1998).

Shaw, J.-P. and Cundy, K.C., "Biological Screens of PMEA Prodrugs," *Pharm. Res.* 10:S-294, Kluwer Academic Publishers B.V., Abstract No. PDD 7480 (1993).

Shih, Y.-E., et al., "Preparation and Structures of 2-Dimethylamino-4-phenyl-1,3,2-dioxaphosphorinane-2-oxides," *Bull. Inst. Chem. Acad. Sin.* 41:9-16, Academia Sinica, Nankang, Taipei, Taiwan (1994).

Sullivan-Bolyai, J., et al., "Safety, Tolerability, Antiviral Activity, and Pharmacokinetics of Pradefovir Mesylate in Patients with Chronic Hepatitis B Virus Infection: 24-Week Interim Analysis of a Phase 2 Study," AASLD Program, *Hepatology* 78A:Abstract No. LB 07, John Wiley & Sons, Inc. (Oct. 2005).

Thomson, W., et al., "Synthesis, Bioactivation and Anti-HIV Activity of the Bis(4-acyloxybenzyl) and Mono(4-acyloxybenzyl) Esters of the 5'-monophosphate of AZT," *J. Chem. Soc. Perk. Trans. 1*,1239-1245, Royal Society of Chemistry (1993).

Van Poelje, P., et al., "MB6866 (Hepavir B), A HepDirect™ Prodrug of Adefovir: Mechanism of Activation and Liver Targeting," AASLD Abstracts, *Hepatology* 706A:Abstract No. 1143, John Wiley & Sons, Inc. (Oct. 2003).

Venook, A., "Treatment of Hepatocellular Carcinoma: Too Many Options?," *J. Clin. Oncol.* 12:1323-1334, American Society of Clinical Oncology (1994).

Vo-Quang, Y., et al., "(1-Amino-2-propenyl)phosphonic Acid, an Inhibitor of Alanine Racemase and D-Alanine:D-Alanine Ligase," *J. Med. Chem.* 29:579-581, American Chemical Society (1986).

Wagner, A., et al., "Direct Conversion of Tetrahydropyranylated Alcohols to the Corresponding Bromides," *Tetra. Lett.* 30:557-558, Pergamon Press plc (1989).

Wallace, E.M., et al., "Design and Synthesis of Potent, Selective Inhibitors of Endothelin-Converting Enzyme," *J. Med. Chem.* 41:1513-1523, American Chemical Society (1998).

Walsh, E., et al., "Phenoxymethylphosphonic Acids and Phosphonic Acid Ion-exchange Resins," *Phenoxymethylphosphonic Acid Ion-Exchange Resins* 78:4455-4458, American Chemical Society (1956).

Watkins, P., "Noninvasive tests of CYP3A enzymes," *Pharmacogenetics* 4:171-184, Lippincott Williams & Wilkins (1994).

Weber, G.F. and Waxman, D.J., "Activation of the Anti-cancer Drug Ifosphamide by Rat Liver Microsomal P450 Enzymes," *Biochem. Pharm.* 45:1685-1694, Pergamon Press Ltd. (1993).

Weibel, M., et al., "Potentiating Effect of {2-[2-[(2-Amino-1,6-Dihydro-6-Oxo-9H-Purin-9-yl)Methyl-Phenyl] Ethenyl]-Phosphonic Acid (MDL 74,428), A Potent Inhibitor of Purine Nucleoside Phosphorylase, on the Antiretroviral Activities of 2',3'-Dideoxyinosine Combined to Ribavirin in Mice," *Biochem. Pharmacol.* 48:245-252, Elsevier Science Ltd. (1994).

Wileman, T., et al., "Receptor-mediated endocytosis," *Biochem. J.* 232:1-14, Portland Press (1985).

Yu, L. J., et al., "In vivo Modulation of Alternative Pathways of P-450-Catalyzed Cyclophosphamide Metabolism: Impact on Pharmacokinetics and Antitumor Activity," *J. Pharmacol. Exp. Ther.* 288:928-937, The American Society for Pharmacology and Experimental Therapeutics (1999).

Zon, G., "Cyclophosphamide Analogues" in *Progress in Medicinal Chemistry*, Ellis, G.P., et al., eds., Elsevier Biomedical Press, Chapter 4, pp. 205-246 (1982).

Zon, G., et al., "NMR Spectroscopic Studies of Intermediary Metabolites of Cyclophosphamide. A Comprehensive Kinetic Analysis of the Interconversion of *cis*-and *trans*-4-Hydroxycyclophosphamide with Aldophosphamide and the Concomitant Partitioning of Aldophosphamide between Irreversible Fragmentation and Reversible Conjugation Pathways," *J. Med. Chem.* 27:466-485, American Chemical Society (1984).

International Search Report for International Application No. PCT/US03/14821, mailed Feb. 15, 2005, International Searching Authority/US Patent Office, Alexandria, VA.

Office Action for U.S. Appl. No. 10/436,799, Kopcho et al., mailed Jul. 1, 2004.

Office Action for U.S. Appl. No. 10/436,799, Kopcho et al., mailed Sep. 23, 2005.

Dang, Q., et al., "A New Regio-Defined Synthesis of PMEA," *Nucleosides & Nucleotides* 17/8: 1445-1451, Marcel Dekker, Inc. (1998).

Desta, Z., et al., "Stereoselective Metabolism of Cisapride and Enantiomer-Enantiomer Interaction in Human Cytochrome P450 Enzymes: Major Role of CYP3A," *J. Pharmacol. Exp. Ther.* 298/2:508-520, American Society for Pharmacology and Experimental (2001).

Dyatkina, Natalja, et al., "Synthesis of the Four Possible Stereoisomeric 5'-Nor Carbocyclic Nucleosides from One Common Enantiomerically Pure Starting Material," *Tetrahedron Letters* 35/13: 1961-1994 Elsevier Science Ltd. (1994).

Echizen, H., et al., "Identification of CYP3A4 as the Enzyme Involved in the Mono-N-Dealkylation of Disopyramide Enantiomers in Humans," *Drug Metabolism and Disposition* 28/3: 937-944, American Society for Pharmacology and Experimental Therapeutics (2000).

Fang, C., et al., "Liver-Targeting Prodrug of PMEA Induces a Much More Favorable Kidney and Liver Toxicological Gene Expression in Rats Compared to BisPOM-PMEA," Abstract #1274, 42nd Annual Meeting of the Society of Toxicology, Salt Lake City, UT (Mar. 9-13, 2003).

Fang, C., et al., "Renal Toxicological Gene Response to Anti-Hepatitis B Prodrugs Hepavir B and Hepsera in Rats," Abstract #1472, 43rd Annual Meeting of the Society of Toxicology, Baltimore, MD (Mar. 21-25, 2004).

Li, X., et al., "Enantiomer/Enantiomer Interactions between the S- and R- Isomers of Omeprazole in Human Cytochrome P450 Enzymes: Major Role of CYP2C19 and CYP3A44," *J. Pharmacol. Exp. Ther.* 315/2: 777-787, American Society for Pharm and Exp Ther (2005).

Lilja, J.J., et al., "Grapefruit juice—simvastatin interaction: Effect on serum concentrations of simvastatin, simvastatin acid, and HMG-CoA reductase inhibitors," *Clin. Pharmacol. Ther.* 64:477-483, Mosby, Inc. (1998).

Lin, C.-C., et al., "Comparative Disposition and Metabolic Profiles of [$^{14}$C]Remofovir and [$^{14}$C]Adefovir Dipivoxil in Rat Liver and Kidney," Abstracts of the 40th Annual Meeting of the European Association for the Study of the Liver, Paris, France, *J. Hepatology* 42/2 Abstract #405 Elsevier (Apr. 2005).

Lin, C.-C., et al., "Single-Dose Pharmacokinetics and Metabolism of [$^{14}$C]Remofovir in Rats and Cynomolgus Monkeys," *Antimicrobial Agents and Chemotherapy* 49/3: 925-930, American Society for Microbiology (Mar. 2005).

Lown, K.S., et al., "Grapefruit Juice Increases Felodipine Oral Availability in Humans by Decreasing Intestinal CYP3A Protein Expression," *J. Clin. Invest.* 99:2545-2553, American Society for Clinical Investigation, Inc. (1997).

Martin, John C., et al., "Synthesis and Antiviral Activity of Various Esters of 9-[(1,3-Dihydroxyl-2-propoxy)methyl]guanine," *J. Pharmaceutical Sciences* 76/2: 180-184, American Pharmaceutical Association (1987).

Paine, M.F., et al., "The Human Intestinal Cytochrome P450 'Pie'," *Drug Metabolism and Disposition* 34/5: 880-886, Williams and Wilkins (2006).

Reddy, K. Raja, et al., "Pradefovie (MB06866Q+): A Novel Hepatitis B Antiviral Therapy Using the HepDirect® Prodrug Technology for Targeting Adefovir to the Liver," poster presented at the XVII International Roundtable on Nucleosides, Nucleotides and Nucleic Acids, Bern, Switzerland (Sep. 3-7, 2006).

Reddy, K. Raja, et al., "HepDirect™ Prodrugs of Adefovir: Design, Synthesis and Optimization," Abstract for 227th ACS National Meeting in Anaheim, CA (Mar. 28-Apr. 1, 2004).

Reddy, K Raja, "MB06866 (Hepavir B) A HepDirect™ Prodrug of Adefovir: Mechanism of Activation and Liver Targeting," Abstract for 227th ACS National Meeting in Anaheim, CA (Mar. 28-Apr. 1, 2004).

Shimada, T., et al., "Interindividual Variations in Human Liver Cytochrome P-450 Enzymes Involved in the Oxidation of Drugs, Carcinogens and Toxic Chemicals: Studies with Liver Microsomes of 30 Japanes and 30 Caucasians," *J. Pharmacol. Exp. Ther.* 270:414-423, American Society for Pharmacology and Experimental Therapeutics (1994).

Vitarella, D., et al., "Hepavir B, A CYP3A4-Activated Prodrug of PMEA, Showed Better Safety than Hepsera in Pre-Clinical Studies," Abstract #995 of the 43rd Annual Meeting of the Society of Toxicology, Baltimore, MD (Mar. 2004).

Xu, C.R., et al., "Toxicokinetics of Remofovir in Mice, Rats and Monkeys After Repeated Oral Administrations," Abstract #PB-P008 of the 64th International Congress FIP World Congress of Pharmacy and Pharmaceutical Science, New Orleans, LA (Sep. 2004).

Xu, C.R., et al., "Toxicokinetics of Adefovir Dipivoxil and Remofovir in 28-Day Toxicity Studies," Abstract #PB-P009 of the 64th International Congress FIP World Congress of Pharmacy and Pharmaceutical Science, New Orleans, LA (Sep. 2004).

Office Action for U.S. Appl. No. 11/145,194, Erion et al., mailed Mar. 24, 2005.

\* cited by examiner

Ketoconazole Inhibition of Compound 4 Activation in Human Liver Microsomes

Liver PMEApp Levels Following I.V. Administration

Liver PMEApp Levels Following Oral Administration

ORAL

Liver Concentration – Time Profile of PMEApp

Accumulation of PMEApp in Rat Hepatocytes

Liver Tissue Distribution

Kidney Tissue Distribution

Small Intestine Tissue Distribution

PHOSPHONIC ACID BASED PRODRUGS OF PMEA AND ITS ANALOGUES

RELATED APPLICATIONS

This application claims benefit of U.S. Provisional Application No. 60/380,545 filed May 13, 2002 and which is incorporated by reference herein in its entirety, including figures.

FIELD OF THE INVENTION

The present invention is directed towards novel phosphonate prodrugs with antiviral and anticancer activity, to their preparation, to their synthetic intermediates, and to their uses. More specifically, the invention relates to the area of optionally substituted cyclic 1,3-propanyl-1-aryl esters of phosphonic acid antivirals based on PMEA or related analogues.

BACKGROUND OF THE INVENTION

The following description of the background of the invention is provided to aid in understanding the invention, but is not admitted to be, or to describe, prior art to the invention. All publications are incorporated by reference in their entirety.

9-(2-phosphonylmethoxyethyl)adenine (PMEA) and related analogues (U.S. Pat. No. 4,808,716; U.S. Pat. No. 5,142,051; De Clercq, et al., *Antiviral Res.* 8(5–6):261–72 (1987)) are phosphonic ac exhibit antiviral activity, including activity against hepatitis B and HIV. The dipivaloyloxy methylene ester of PMEA ("Bis POM PMEA") is in clinical trials for the treatment of hepatitis B. (Benhamou, et al., *Lancet* 358(9283):718–23 (2001)) PMEA is thought to act by blocking DNA polymerase of HBV. In addition, some studies have shown that these compounds also show anticancer activity. (Murono, et al., *Cancer Res.*, 61(21):7875–7 (2001)) The biologically active compound is thought to be the diphosphate, such as PMEApp, which is produced from the phosphonic acid most likely as result of specific mammalian intracellular kinases.

Compounds containing phosphonic acids and their salts are highly charged at physiological pH and therefore frequently exhibit poor oral bioavailability, poor cell penetration and limited tissue distribution (e.g., CNS). In addition, these acids are also commonly associated with several other properties that hinder their use as drugs, including short plasma half-life due to rapid renal clearance, as well as toxicities (e.g., renal, gastrointestinal, etc.) (e.g., *Antimicrob Agents Chemother.* 42(5): 1146–50 (1998)).

For example, PMEA exhibits a very low volume of distribution, presumably due to its high negative charge. In humans, 98% of the dose is excreted renally as a result of the presence of organic anion transporters on the basolateral surface of the kidney tubule cells which help facilitate the renal clearance of PMEA. PMEA therapy is associated with severe renal toxicity possibly due to the exposure and accumulation of PMEA and related phosphorylated species in the kidney. Thus, there is a need for means to reduce the toxicity of PMEA and related analogues.

Cyclic phosphonate esters have also been described for PMEA and related analogues. The numbering for these cyclic esters is shown below:

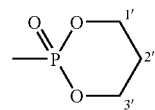

Unsubstituted cyclic 1',3'-propanyl esters of PMEA were prepared but showed no in vivo activity. EP 0 481 214 B1 discloses examples of cyclic prodrugs of PMEA wherein the 1' and 3' positions are unsubstituted. The application and a subsequent publication by the inventors (Starrett et al., *J. Med. Chem.* 37:1857–1864 (1994)) further disclose their findings with the compounds, namely that these compounds showed no oral bioavailability and no biological activity. The compounds were shown to be unstable at low pH, e.g., the cyclic 2',2'-difluoro-1',3'-propane ester is reported to be hydrolytically unstable with rapid generation of the ring-opened monoester.

Cyclic prodrugs with aryl groups at 1' are described for phosphonates that are known to be particularly useful in glucose lowering activity and therefore are useful in treating diabetes. (U.S. Pat. No. 5,658,889, WO 98/39344, WO 98/39343, and WO 98/39342) In addition, U.S. Pat. No. 6,312,662 discloses the use of this strategy for the liver-specific delivery of various drugs and compound classes to the liver for the treatment of patients with liver diseases such as hepatitis B and hepatocellular carcinoma.

Furthermore, diseases of the liver, such as hepatitis and liver cancer, remain poorly treated with current therapies due to dose-limiting extrahepatic side effects or inadequate delivery of chemotherapeutic agents to the target tissue.

SUMMARY OF THE INVENTION

Figure 1:
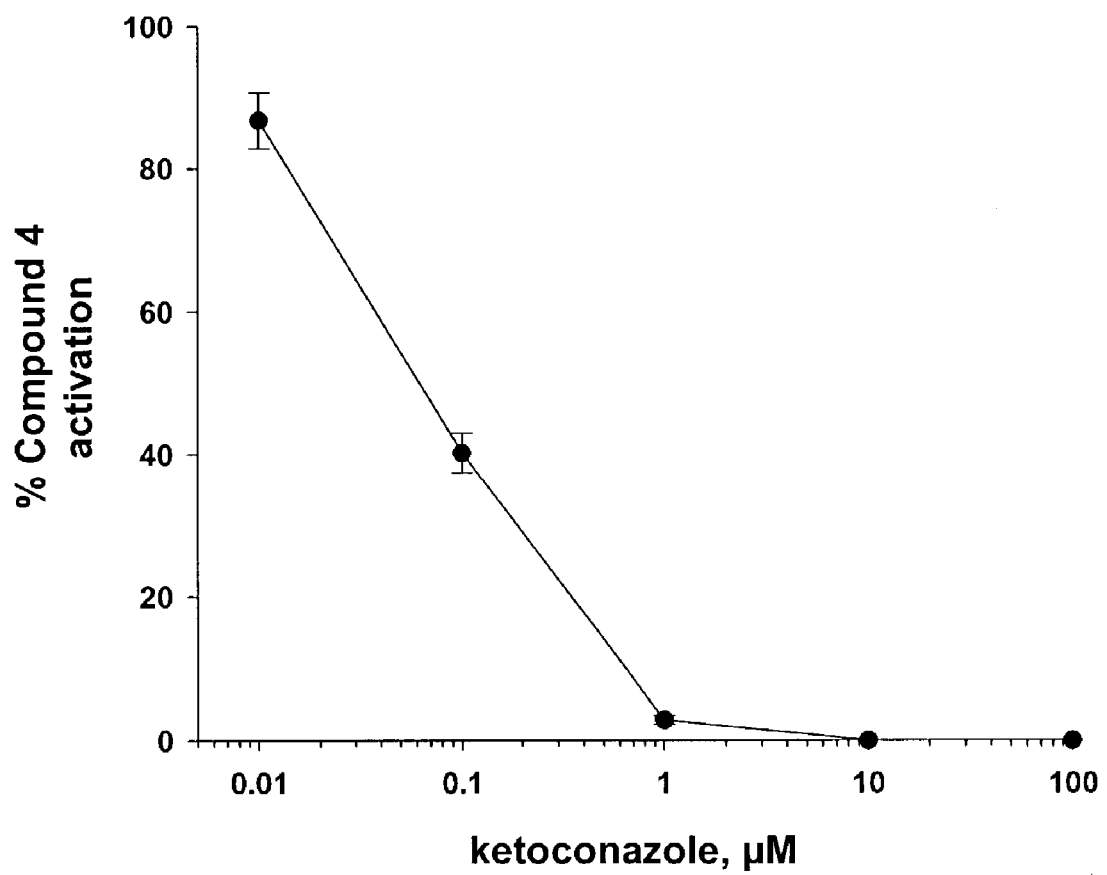
FIG. 1. Depicts the ketoconazole dependent inhibition of Compound 4 activation in Human Liver Microsomes.

The present invention is directed towards novel cyclic 1,3-propanyl-1-aryl phosphonate cyclic esters of PMEA and related analogues having cis relative stereochemistry between groups M & V, their preparation, their synthetic intermediates, and their uses. In one embodiment, the cis cyclic esters have S stereochemistry where V is attached.

In one aspect, the invention is directed towards the use of these cyclic esters to treat viral infections. Another aspect of the invention is the use of these cyclic esters of PMEA and like analogues to treat diseases that benefit from enhanced drug distribution to the liver and like tissues and cells, including hepatitis B and liver cancer. Another aspect of the invention is the use of these compounds to enhance oral delivery and/or prolong the pharmacodynamic half-life of PMEA and like analogues.

In addition, the compounds of the current invention are used to achieve sustained delivery of PMEA and like analogues and/or to increase the therapeutic index of the drug.

In another aspect of the invention, a method of making the cis prodrugs is described. In another aspect, a method of making substantially enantiomerically pure cis cyclic esters having S stereochemistry where V is attached is described.

One aspect of the present invention concerns compounds that are converted in vitro or in vivo to the corresponding $MPO_3^{2-}$, $MP_2O_6^{3-}$ and $MP_3O_9^{4-}$ and are of Formula I:

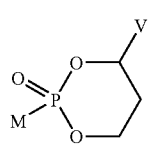

Formula I wherein:

M and V are cis to one another and $MPO_3H_2$ is a phosphonic acid selected from the group consisting of 9-(2-phosphonylmethoxyethyl)adenine, (R)-9-(2-phosphonylmethoxypropyl)adenine, 9-(2-phosphonylmethoxyethyl)guanine, 9-(2-phosphonylmethoxyethyloxy)adenine, 9-(2-phosphonylmethoxyethyl)-2,6-diaminopurine, (S)-1-(3-hydroxy-2-phosphonylmethoxypropyl)cytosine, (S)-9-(3-hydroxy-2-phosphonylmethoxypropyl)adenine, 9-(3-hydroxy-2-phosphonylmethoxypropyl)guanine, and (S)-9-(3-fluoro-2-phosphonylmethoxypropyl)adenine;

V is selected from a group consisting of phenyl, 2-pyridyl, 3-pyridyl, 4-pyridyl, 2-furanyl, 3-furanyl, 2-thienyl, and 3-thienyl, all optionally substituted with 1–3 substituents selected from a group consisting of F, Cl, Br, C1–C3 alkyl, $CF_3$ and $OR^6$;

$R^6$ is selected from the group consisting of C1–3 alkyl, and $CF_3$;

and pharmaceutically acceptable salts thereof.

A method for the preparation of the compounds described in this invention is described and relies on the reaction of PMEA or a PMEA analogue either as the phosphonic acid or in the activated form (e.g., dichloridate) with a 1,3-propane diol in a manner that preferentially favors the production of the cis stereoisomer. In addition, methods and salt forms are described that enable isolation and purification of the desired isomer.

Since these compounds have asymmetric centers, the present invention is directed not only to racemic and diastereomeric mixtures of these compounds, but also to individual stereoisomers. The present invention also includes pharmaceutically acceptable and/or useful salts of the compounds of Formula I, including acid addition salts.

Definitions

In accordance with the present invention and as used herein, the following terms are defined with the following meanings, unless explicitly stated otherwise.

The term "alkyl" refers to saturated aliphatic groups including straight-chain, branched chain and cyclic groups. Suitable alkyl groups include methyl, ethyl, n-propyl, isopropyl, and cyclopropyl.

The term "aryl" refers to aromatic groups which have 5–6 ring atoms. Suitable aryl groups include phenyl, furanyl, pyridyl, and thienyl. Aryl groups may be substituted.

The term "pharmaceutically acceptable salt" includes salts of compounds of Formula I derived from the combination of a compound of this invention and an organic or inorganic acid or base, such that they are acceptable to be safely administered to animals. Suitable acids include acetic acid, adipic acid, benzenesulfonic acid, (+)-7,7-dimethyl-2-oxobicyclo[2.2.1]heptane-1-methanesulfonic acid, citric acid, 1,2-ethanedisulfonic acid, dodecyl sulfonic acid, fumaric acid, glucoheptonic acid, gluconic acid, glucoronic acid, hippuric acid, hydrochloride hemiethanolic acid, HBr, HCl, HI, 2-hydroxyethanesulfonic acid, lactic acid, lactobionic acid, maleic acid, methanesulfonic acid, methylbromide acid, methyl sulfuric acid, 2-naphthalenesulfonic acid, nitric acid, oleic acid, 4,4'-methylenebis[3-hydroxy-2-naphthalenecarboxylic acid], phosphoric acid, polygalacturonic acid, stearic acid, succinic acid, sulfuric acid, sulfosalicylic acid, tannic acid, tartaric acid, terphthalic acid, and p-toluenesulfonic acid.

The term "prodrug" as used herein refers to any compound that when administered to a biological system generates a biologically active compound as a result of spontaneous chemical reaction(s), enzyme catalyzed chemical reaction(s), and/or metabolic chemical reaction(s), or a combination of each. Standard prodrugs are formed using groups attached to functionality, e.g., HO—, HS—, HOOC—, $R_2N$—, associated with the drug, that cleave in vivo. Standard prodrugs include but are not limited to carboxylate esters where the group is alkyl, aryl, aralkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. The groups illustrated are exemplary, not exhaustive, and one skilled in the art could prepare other known varieties of prodrugs. Such prodrugs of the compounds of Formula I, fall within the scope of the present invention. Prodrugs must undergo some form of a chemical transformation to produce the compound that is biologically active or is a precursor of the biologically active compound. In some cases, the prodrug is biologically active, usually less than the drug itself, and serves to improve drug efficacy or safety through improved oral bioavailability, pharmacodynamic half-life, etc. The biologically active compounds include, for example, anticancer agents, and antiviral agents.

The term "cyclic 1',3'-propane ester", "cyclic 1,3-propane ester", "cyclic 1',3'-propanyl ester", and "cyclic 1,3-propanyl ester" refers to the following:

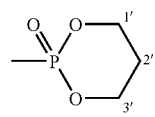

The term "cis" stereochemistry refers to the relationship of the V group and M group positions on the six-membered ring. Formula II below shows a cis stereochemistry.

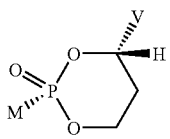

II

The term "N6-substituted" refers to the substitution at the amine attached at the 6-position of a purine ring system. N6- is generally substituted with a dialkylaminomethylene group wherein $R^1$ groups include but are not limited to C1–C4 acyclic alkyl, C5–C6 cyclic alkyl, benzyl, phenethyl, or $R^1$ groups together form piperdine, morpholine, and pyrrolidine.

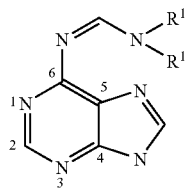

The term "dialkylaminomethyleneimine" refers to the following structure:

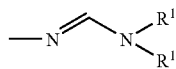

wherein $R^1$ groups include but are not limited to C1–C4 acyclic alkyl, C5–C6 cyclic alkyl, benzyl, phenethyl, or $R^1$ groups together form piperdine, morpholine, and pyrrolidine.

The term "liver" refers to liver and to like tissues and cells that contain the CYP3A4 isozyme or any other P450 isozyme found to oxidize the cyclic prodrugs of the invention. Based on Example D, we have found that compounds of Formula I are selectively oxidized by the cytochrome P450 isoenzyme CYP3A4. According to DeWaziers et al. (*J. Pharm. Exp. Ther.* 253:387–394 (1990)), CYP3A4 is located in humans in the following tissues (determined by immunoblotting and enzyme measurements):

| Tissues | % of liver activity |
|---|---|
| Liver | 100 |
| Duodenum | 50 |
| jejunum | 30 |
| ileum | 10 |
| colon | <5 (only P450 isoenzyme found) |
| stomach | <5 |
| esophagus | <5 |
| kidney | not detectable |

Thus, "liver" more preferably refers to the liver, duodenum, jejunum, ileum, colon, stomach, and esophagus. Most preferably, liver refers to the liver organ.

The term "enhancing" refers to increasing or improving a specific property.

The term "liver specificity" refers to the ratio:

$$\frac{[\text{parent drug or a drug metabolite in liver tissue}]}{[\text{parent drug or a drug metabolite in blood, urine or another non-hepatic tissue}]}$$

as measured in animals treated with the drug or a prodrug. The ratio can be determined by measuring tissue levels of the parent drug, or drug metabolite(s) including the biologically active drug metabolite, or both at a specific time or may represent an AUC (area under curve) based on values measured at three or more time points.

The term "increased or enhanced liver specificity" refers to an increase in the liver specificity ratio in animals treated with the prodrug relative to animals treated with the parent drug.

The term "enhanced oral bioavailability" refers to an increase of at least 50% of the absorption of the dose of the parent drug or prodrug (not of this invention) from the gastrointestinal tract. More preferably it is at least 100%. Measurement of oral bioavailability usually refers to measurements of the prodrug, drug, or drug metabolite in blood, tissues, or urine following oral administration compared to measurements following systemic administration.

The term "drug metabolite" refers to any compound produced in vivo or in vitro from the parent drug, or its prodrugs.

The term "pharmacodynamic half-life" refers to the time after administration of the drug or prodrug to observe a diminution of one half of the measured pharmacological response. Pharmacodynamic half-life is enhanced when the half-life is increased by preferably at least 50%.

The term "pharmacokinetic half-life" refers to the time after administration of the drug or prodrug to observe a diminution of one-half of the drug concentration in plasma or tissues.

The term "therapeutic index" refers to the ratio of the dose of a drug or prodrug that produces a therapeutically beneficial response relative to the dose that produces an undesired response such as death, an elevation of markers that are indicative of toxicity, and/or pharmacological side effects.

The term "sustained delivery" refers to an increase in the period in which there is a prolongation of therapeutically-effective drug levels due to the presence of the prodrug.

The term "bypassing drug resistance" refers to the loss or partial loss of therapeutic effectiveness of a drug (drug resistance) due to changes in the biochemical pathways and cellular activities important for producing and maintaining the biological activity of the drug and the ability of an agent to bypass this resistance through the use of alternative pathways or the failure of the agent to induce changes that tend to resistance.

The term "therapeutically effective amount" refers to an amount that has any beneficial effect in treating a disease or condition.

The term "phosphonate" refers to compounds attached via carbon to $PO_3^{2-}$.

The term "parent drug" refers to PMEA, or its analogues, when $MPO_3H_2$ is PMEA, or its analogues, respectively.

The term "biologically active drug or agent" refers to the chemical entity that produces the biological effect. In this invention, biologically active agents refers to $MPO_3^{2-}$, $MP_2O_6^{3-}$, or $MP_3O_9^{4-}$ where M can be the same M as in the parent drug or a metabolite.

The term "PMEA analogue" refers to compounds that have a nucleotide base connected to a phosphoric acid via a chain of atoms. Suitable PMEA analogues include (R)-9-(2-phosphonylmethoxypropyl)adenine, 9-(2-phosphonylmethoxyethyl)guanine, 9-(2-phosphonylmethoxyethyloxy) adenine, 9-(2-phosphonylmethoxyethyl)-2,6-diaminopurine, (S)-1-(3-hydroxy-2-phosphonylmethoxypropyl)cytosine, (S)-9-(3-hydroxy-2-phosphonylmethoxypropyl)adenine, 9-(3-hydroxy-2-phosphonylmethoxypropyl)guanine, and (S)-9-(3-fluoro-2-phosphonylmethoxypropyl)adenine.

The term "percent enantiomeric excess (% ee)" refers to optical purity. It is obtained by using the following formula:

$$\frac{[R]-[S]}{[R]+[S]} \times 100 = \% R - \% S = \% ee \text{ R isomer}$$

where [R] is the amount of the R isomer and [S] is the amount of the S isomer. This formula provides the % ee when R is the dominant isomer.

The terms "chiral alcohol" or "chiral diol" refers to a 1,3-diol where % ee is $\geqq 50\%$.

The term "amelioration of gastrointestinal toxicity" refers to blocking, suppressing, or lessening toxicity to gastrointestinal tissues and organs relative to the toxicity that would otherwise occur with bis POM PMEA.

The term "amelioration of renal toxicity" refers to blocking, suppressing, or lessening toxicity to renal tissues and organs relative to the toxicity that would otherwise occur with bis POM PMEA.

The term "amelioration of extrahepatic toxicity" refers to blocking, suppressing, or lessening toxicity to tissues and organs outside of the liver relative to the toxicity that would otherwise occur with bis POM PMEA.

The term "resistant to antiviral therapy" refers to not fully responding to or not fully affected by antiviral therapy treatment.

The term "administered simultaneously" refers to the administration of one drug at or near the same time in which another drug is administered. Preferably administration is within 30 minutes of one another.

The term "interferon" refers to a family of species-specific vertebrate proteins that confer non-specific resistance to a broad range of viral infections, affect cell proliferation and modulate immune responses. Suitable interferons include interferon alpha, interferon gamma, Omega interferon, Ominferon, Roferon-A, Albuferon, Alferon, Infergen, Intron A, PEG-intron, Pegasys, interferon fusions, interferon derivatives, and small molecule interferon inducers.

The term "pegylated interferon" refers to an interferon that has been modified by the attachment of polyethylene glycol molecules, in order to increase its half-life by decreasing in vivo clearance, and thereby increasing its duration of action.

The following well known drugs are referred to in the specification and the claims. Abbreviations and common names are also provided.

ara-A; 9-beta-D-Arabinofuranosyladenine (Vidarabine)
AZT; 3'-Azido-2',3'-dideoxythymdine (Zidovudine)
d4T; 2',3'-Deoxy-2',3'-Didehydrothymidine (Stavudine)
ddI; 2',3'-Dideoxyinosine (Didanosine)
ddA; 2',3'-Dideoxyadenosine
ddC; 2',3'-Dideoxycytidine (Zalcitabine)
L-ddC; L-2',3'-dideoxycytidine
L-FddC; L-2',3'-dideoxy-5-fluorocytidine
L-d4C; L-2',3'-Dideoxy-2',3'-didehydrocytidine
L-Fd4C; L-2',3'-Dideoxy-2',3'-didehydro-5-fluorocytidine (ACH 126,443)
3TC; (−)-2',3'-Dideoxy-3'-thiacytidine; (−)-1-((2R,5S)-2-(Hydroxymethyl)-1,3-oxathiolan-5-yl)cystosine (Lamivudine)
1-beta-D-Ribofuranosyl-1,2,4-triazole-3-carboxamide (Ribavirin) (Virazole)
FIAU; 1-(2-Deoxy-2-fluoro-b-D-arabinofuranosyl)-5-iodouridine
FIAC; 1-(2-Deoxy-2-fluoro-b-D-arabinofuranosyl)-5-iodocytosine
L-FMAU; 2'-Fluoro-5-methyl-β-L-arabino-furanosyluracil (Clevudine)
BvaraU; 1-beta-D-Arabinofuranosyl-E-5-(2-bromovinyl)uracil (Sorivudine)
E-5-(2-bromovinyl)-2'-deoxyuridine
TFT; Trifluorothymidine (Trifluorothymidine)
5-Propynyl-1-arabinosyluracil (Zonavir)
CDG; carbocyclic 2'-deoxyguanosine
DAPD; beta-D-2-Hydroxymethyl-5-(2,6-diaminopurin-9-yl)-1,3-doxalane
FDOC; (−)-beta-D-5-Fluoro-1-[2-(hydroxymethyl)-1,3-dioxolane]cytosine
d4C; 2',3'-Dideoxy-2',3'-didehydrocytidine
DXG; dioxolane guanosine
FEAU; 1-(2'-deoxy-2'-fluoro-1-β-D-arabinofuranosyl)-5-ethyluracil
FLG; 2',3'-Dideoxy-3'-fluoroguanosine
FLT; 2',3'-Dideoxy-3'-fluorothymidine
FTC; (−)-cis-5-Fluoro-1-[2-(hydroxymethyl)-1,3-oxathiolan-5-yl]cytosine (Coviracil)
5-yl-carbocyclic 2'-deoxyguanosine (BMS-200475) (Entecavir)
[1-(4'-Hydroxy-1',2'-butadienyl)cytosine] (Cytallene)
Oxetanocin A; 9-((2R,3R,4S)-3,4-Bis(hydroxymethyl)-2-oxetanyl)adenine NK 84–0218
Oxetanocin G; 9-((2R,3R,4S)-3,4-Bis(hydroxymethyl)-2-oxetanyl)guanine
ddAPR; 2,6-diaminopurine-2',3'-dideoxyriboside
Cyclobut A; (+/−)-9-[(1-beta,2-alpha,3-beta)-2,3-Bis(hydroxymethyl)-1-cyclobutyl]adenine
Cyclobut G; (+/−)-9-[(1-beta,2-alpha,3-beta)-2,3-Bis(hydroxymethyl)-1-cyclobutyl]guanine (Lobucavir)
5-fluoro-2'-deoxyuridine (Floxuridine)
dFdC; 2',2'-difluorodeoxycytidine (Gemcitabine)
araC; arabinosylcytosine (Cytarabine)
BUdR; 5-Bromodeoxyuridine (Broxine)
IDU; 5-Iodo-2'-deoxyuridine (Idoxuridine)
CdA; 2-Chloro-2'-deoxyadenosine (Cladribine)
F-ara-A; 2-Fluoroarabinosyladenosine (Fludarabine)
ACV; 9-(2-Hydroxyethoxylmethyl)guanine (Acyclovir)
GCV; 9-((1,3-Dihydroxy-2-propoxy)methyl)guanine (gancyclovir)
9-(4-Hydroxy-3-(hydroxymethyl)but-1-yl)guanine (Penciclovir)
(R)-9-(3,4-Dihydroxybutyl)guanine (Buciclovir)
Phosphonoformic acid (Foscarnet)
PPA; Phosphonoacetic acid
PMEA; 9-(2-Phosphonylmethoxyethyl) adenine (Adefovir)
PMEDAP; 9-(2-Phosphonylmethoxyethyl)-2,6-diaminopurine
HPMPC; (S)-1-(3-Hydroxy-2-phosphonylmethoxypropyl) cytosine (Cidofovir)

HPMPA; (S)-9-(3-Hydroxy-2-phosphonylmethoxypropyl) adenine
FPMPA; 9-(3-Fluoro-2-phosphonylmethoxypropyl) adenine
PMPA; (R)-9-(2-phosphonylmethoxypropyl) adenine
Ara-T; 9-beta-D-Arabinofuranosylthymidine
FMdC; (E)-2'-deoxy-2'(fluoromethylene)cytidine
AICAR; 5-aminoimidazole-4-carboxamido-1-ribofuranosyl
AM365; acylic guanosine nucleoside analogue
L-dT; beta-L-2'-deoxythymidine (NV-O$_2$B)
L-dC; beta-L-2'-deoxycytosine, valine prodrug derivatives of beta-L-2'-deoxycytosine
MCC478; 2-aminophosphonomethoxy ethyl purine analogue
Interferon alpha
Pegylated interferons
Famciclovir, 2-[2-(2-amino-9H-purin-9-yl)ethyl]-1,3-propanediol diacetate
XTL 001; monoclonal antibody combination (Hepe X-B)
Theradigm
Zadaxin, thymosin alpha
HBV DNA vaccine
EHT 899, viral protein
ICN 2001, nucleoside analogue
Fluor L and D nucleosides, nucleoside analogue
Racivir
Robustaflavone, naturally occurring biflavanoid

DETAILED DESCRIPTION OF THE INVENTION

The invention is directed to the discovery that the cis stereochemistry of cyclic 1,3-propanyl-1-aryl esters of PMEA or related analogues are effective prodrugs. It is believed that these cyclic ester prodrugs of PMEA and PMEA analogues require activation through the action of P450 enzymes to generate the biologically active drug in vivo. The high levels of P450 enzymes such as CYP3A4 in the liver enables the activation of the compounds to be largely in the liver and therefore to increase liver levels of the biologically active drug and/or decrease levels of the biologically active drug outside of the liver. Liver specificity is dependent not only on P450 tissue distribution, but also prodrug activation rate and subsequent phosphorylation of PMEA or its analogues relative to pathways that export PMEA out of the hepatocyte and into the blood stream or bile. Poor activation would result in low PMEA levels in the liver (as well as extrahepatic tissues). Good activation but slow conversion to the PMEA diphosphate ("PMEApp") by downstream kinases would limit PMEApp production. Rapid export of PMEA into the blood stream would decrease the liver specificity and limit the improvement of the therapeutic index. (Mulato et al., *J. Pharmacol. Exp. Ther.* 295:10–15 (2001); *Gilead Sciences, Inc. Press Release* (Jun. 22, 2001) Foster City, Calif.).

Compounds of the present invention are metabolized in the liver to produce the phosphonate which can be further metabolized to the biologically active drug. Decreased extrahepatic toxicity can also enable higher doses and, therefore, increased liver levels of the biologically active agent in the liver.

In another aspect of the invention, the cyclic esters of the present invention were found to exhibit good stability in aqueous solutions and good oral bioavailability. Good stability can enable the prodrug to exist in the gastrointestinal environment (pHs 1–9) for a time sufficient to ensure good oral absorption. In addition, oral bioavailability is dependent on GI stability to enzymes. Given that the small intestine, which is the predominant site for drug absorption, expresses relatively high levels of CYP3A4 (50% compared to the liver), compounds of the type described could be associated with poor oral bioavailability due to intestinal prodrug activation and conversion to the corresponding phosphonic acid. As described in this invention, however, the compounds of the present invention show good oral bioavailabilities.

In another aspect of the invention, the cyclic esters of the present invention can also be used to enhance the pharmacodynamic half-life relative to the parent drug or prodrug esters [esterase sensitive] that are sensitive to esterases. Compounds of the invention are slowly cleared by the kidney relative to PMEA and other phosphonic acid analogues and, therefore, provide a depot of drug that is released over time. Thus, the compounds of the present invention can produce a sustained therapeutic effect. In contrast, prodrug esters such as the acyloxyalkyl esters like bis POM are rapidly cleaved in vivo and therefore are dependent on the pharmacokinetics of the phosphonic acid. (Noble, S. and Goa, K. L., *Drugs* 58(3):479–487 (1999)).

In another aspect, methods of preparing the cyclic phosphonate compounds are described.

These aspects are described in greater detail below.

Increased Therapeutic Index of Phosphonic Acid Drugs

The compounds of this invention can significantly increase the therapeutic index ("TI") of PMEA and PMEA analogues. In many cases, the increased TI is a result of the high liver specificity which results in higher liver levels of the biologically active drug and therefore allows for a lower dose to be administered to achieve the same therapeutic benefit. Alternatively, an increased TI can result from decreased exposure of the drug to extrahepatic tissues and therefore a decrease in toxicity at doses that achieve similar or higher liver levels of the biologically active drug.

Renal toxicity is a common toxicity associated with phosphonic acids. The toxicity results from transport, e.g., via the organic anion transporters located on the basolateral membrane of the renal proximal tubule, of the negatively charged drug into e.g., tubular cells which then accumulate the drug to high concentrations unless there is an equally efficient transport of the drug out of the cell via luminal transport mechanisms (e.g., anion-exchange or facilitated diffusion). Many examples have been reported in the literature of nephrotoxic phosphonic acids. Renal toxicity is associated with bis POM PMEA in both animals and humans. The toxicity is associated with rapid conversion of bis POM PMEA to PMEA which is then cleared via the kidneys. In fact, 98% of an i.v. dose of PMEA is renally cleared.

Renal toxicity is associated with serum increases in creatinine and decreases in phosphate and ultimately decreased kidney function. The poor therapeutic index associated with bis POM PMEA therapy is a function of an undesirable tissue distribution profile, more specifically, poor distribution of PMEA to liver relative to kidney. The undesirable distribution profile of PMEA can be attributed to its esterase-sensitive (bis POM) prodrug as these ubiquitous enzymes are highly expressed in plasma and the gastrointestinal tissues resulting in high systemic exposure of PMEA. Bis POM PMEA must be administered at low doses in humans (10 mg/day) to avoid such toxicity, thereby minimizing its potential efficacy (*Gilead Sciences, Inc. Press Release* (Jun. 22, 2001) Foster City, Calif.).

In contrast to bis POM PMEA, compounds of this invention result in enhanced PMEA delivery to liver while minimizing systemic and kidney PMEA exposure. Compound 54 is well-absorbed following oral administration and readily distributes to most tissues as the intact prodrug via passive diffusion. Compound 54 will remain stable in blood and in most tissues until it is activated in the liver by the cytochrome P450 enzyme, CYP3A4. This isoform is abundantly expressed in liver where it accounts for approximately 30% of all P450 activity. Liver specificity is gained because no other tissues express CYP3A4 to high levels. Compound 54 results in increased efficacy in the target organ with significantly reduced peripheral drug exposure and consequential toxicities. Alternatively, Compound 54 is less toxic than bis POM PMEA, due to reduced systemic PMEA exposure, and higher doses are administered resulting in improved efficacy compared to bis POM PMEA. In one study, the levels of PMEA and PMEA associated metabolites were measured in rats administered either compound 4 or bis POM PMEA (Example N and O). These studies showed that liver organ levels of PMEApp were higher in animals treated with compound 4 whereas kidney levels and urine levels of PMEA were lower.

Another common toxicity associated with phosphonic acid drugs is gastrointestinal toxicity due to, for example, accumulation of the phosphonic acid or its metabolites (e.g., phosphorylated phosphonic acids) in the gut epithelial cells. Accumulation of drugs in the gut epithelial cells is dependent on many factors. Compounds that are hydrophobic and low molecular weight rapidly diffuse across the gut epithelial cells and enter the blood stream. Compounds that are rapidly metabolized by enzymes in the gut epithelial cells to a charged and highly polar compound can be trapped inside the cells and accumulate to levels that are cytotoxic. Drug metabolism is dependent on the substrate and enzyme specific activity and on other factors, including residence time, i.e. the time in which the drug is exposed to the gut epithelial cells. Factors that affect residence time include drug molecular weight and polarity since these factors increase the diffusion time. In addition, other proteins such as p-glycoproteins can increase the residence time by preventing the drug from transversing the gut by pumping the drug back into the gastrointestinal tract.

Bis POM PMEA therapy in humans is associated with a significant incidence of GI adverse events (Deeks et al., *J. Infect. Dis.* 176:1517–1523 (1997)).

The gastrointestinal tract contains esterases that rapidly cleave bis POM PMEA to PMEA. Accordingly, radiolabeled PMEA and PMEA metabolites were found trapped in the small intestine following administration of bis POM PMEA to rats (Example N). CYP3A4 is also expressed in the small intestine. In contrast to bis POM PMEA, only low levels of PMEA and PMEA metabolites were associated with the small intestine following oral administration of Compound 4 (Example N).

Increased Oral Bioavailability

Phosphonic acids are highly negatively charged molecules at physiological pH. Accordingly, most phosphonic acids exhibit poor oral bioavailability. For example, PMEA has an oral bioavailability of 11% in rats, <1% in monkeys, and <12% in humans. (Cundy, K. C., *Clin. Pharmacokinet.* 36(2):127–143 (1999)). Certain prodrugs of PMEA have been shown to increase oral bioavailability. For example, the esterase-sensitive prodrug, bis POM PMEA has an oral bioavailability of 38%, 25% and 41% in rats, monkeys and humans, respectively. (Shaw et al., *Drug Metab. and Disp.* 25(3):362–366 (1997)). Other prodrugs of PMEA have shown poor oral bioavailability, including 2' and 2',2' disubstituted 1,3-propanyl cyclic prodrugs, due either to poor conversion to PMEA in vivo or to instability to aqueous solutions and therefore production of charged metabolites or PMEA in the GI tract.

Oral bioavailability of P450 substrates is generally low due to the presence of P450s in the gut. For example, drugs such as Cyclosporine, Midazolam and Felodipine all show low oral bioavailability due to P450 metabolism. (Wacher, V. J. et al., *Adv. Drug Deliv. Rev.* 46:89–102 (2001))

Prodrugs of this invention were shown to enhance the oral bioavailability of PMEA and to show good oral bioavailabilities despite being good substrates for CYP3A4 (Example C). Oral bioavailability was dependent on the aryl group and its substituents, on the diol stereoisomer used to prepare the prodrug and the salt form. For example, V=3-chlorophenyl appeared to exhibit better oral bioavailability relative to V=phenyl. (Example C). Oral bioavailability also improved when the S-diol (V=3-chlorophenyl) was used relative to the R-diol. (Example I).

Prodrug Activation

Prodrugs of this invention are activated by P450s, e.g., CYP3A4 in humans. Activation is highly dependent on the structural features of the prodrug moiety as well as the parent drug. Catalytic efficiencies ($V_{max}/K_m$) for each substrate are determined using liver microsomes, supersomes or recombinant enzymes and monitoring either production of the phosphonic acid or its byproduct or the disappearance of the prodrug. As shown in Example P, catalysis is dependent on the ring stereochemistry with the trans isomer of compound 9-{2-[2,4-trans-(S)-(+)-4-(3-chlorophenyl)-2-oxo-1, 3,2-dioxaphosphorinan-2-yl]methoxyethyl} adenine acting as a weak inhibitor whereas the cis isomer is readily oxidized and converted to PMEA.

Prodrug activation was also monitored in hepatoctyes by monitoring the production of PMEApp. As shown in Example B, V=3-chlorophenyl, 4-pyridyl, and phenyl were identified as the prodrug moieties with the best activity in rat hepatocytes.

Prodrug activation was also dependent on the prodrug stereoisomer. The S-diol was the most readily activated enantiomer in vitro in human liver microsomes at both low and high prodrug concentrations. (Example H).

Prodrug activation is an important parameter in drug pharmacokinetics, including duration and oral bioavailability as well as efficacy, e.g., liver levels of the biologically active drug. Prodrugs that are activated efficiently in vivo can result in higher liver levels of PMEApp and in greater conversion of the prodrug to the active drug. The latter can lead to improved oral bioavailabilties. Prodrug activation in vivo is readily monitored with radiolabeled parent drug. Prodrug, PMEA and PMEA metabolites were monitored following administration of Compound 4 to rats (Example N and O). Unreacted prodrug was measured in the feces but undetected in liver organ or the small intestine.

Prodrug Stability

Prodrug stability is a critical factor influencing bulk drug and product shelf life, oral bioavailability, liver distribution, drug toxicity and pharmacokinetic and pharmacodynamic half-life. Phosphonate prodrugs are often unstable in aqueous solutions especially in non-neutral pH solutions. Acyloxyalkyl esters are associated with instability as are other common phosphonate prodrugs. (Oliyai, et al., *Nucleosides, Nucleotides, Nucleic Acids* 20(4–7): 1295–8 (2001)) Cyclic prodrugs are associated with instability stemming from the ring strain. Substituted cyclic prodrugs are reported to exhibit poor stability in aqueous solutions. (Starrett, et al., *J. Med. Chem.* 37(12):1857–64 (1994)).

Instability of prodrugs often leads to production of a monoanion byproduct which is poorly absorbed due to its negative charge. Low bioavailability has been attributed to prodrug instability in the GI tract, including both bis POM PMEA (Benzaria, et al., *J. Med. Chem.* 39(25):4958–65 (1996); Serafinowska, et al., *J. Med. Chem.* 38(8):1372–9 (1995)) prodrugs of PMEA (Starrett, et al., *J. Med. Chem.* 37(12):1857–64 (1994))). Instability to esterases can lead to rapid prodrug cleavage and at sites not associated with the disease. Esterases are thought to be relatively widely distributed with high levels often observed in blood, kidney, gastrointestinal tissue and liver. Rapid cleavage by an esterase can therefore limit oral bioavailability by producing the charged intermediate in the gut prior to absorption. Esterase activity outside of the liver can limit liver distribution of the drug by producing the charged intermediate in extrahepatic tissues (e.g., kidney) or in the blood where upon the drug is then charged and may be limited in its ability to enter hepatocytes and/or may exhibit increased drug clearance through anionic transporters in the kidney.

Prodrugs of this invention exhibited excellent stability in aqueous solutions as well as in rat and human plasma (Examples F and G). The stability of compounds 57 and 54 compared favorably to that of bis POM PMEA (*J. Med. Chem.* 39:4958–4965 (1996)).

Sustained Delivery

Drugs that undergo rapid elimination in vivo often require multiple administrations of the drug to achieve therapeutically effective blood levels over a significant period of time. Other methods are also available including sustained release formulations and devices. Prodrugs that breakdown over time can also provide a method for achieving sustained drug levels. In general, this property has not been possible with the known phosphonate prodrugs since either they undergo rapid hydrolysis in vivo (e.g., acyloxyalkyl esters) or very slow conversion (e.g., di-aryl prodrugs).

The cyclic phosphonate prodrugs of the invention are capable of providing sustained drug release by providing a steady release of the drug over time. Studies in rats and dogs (Examples R and S) indicate that Compound 4 has a preferable pharmacokinetic profile by circulating longer as the intact prodrug, while systemic PMEA exposure was minimized, compared to bis POM PMEA.

Sustained delivery of the drugs is achievable by selecting the prodrugs of Formula I that are hydrolyzed in vivo at a rate capable of maintaining therapeutically effective drug levels over a period of time. Accordingly, prodrugs of this invention can also improve the pharmacodynamic half-life of the drug. The cleavage rate of the drug may depend on a variety of factors, including the rate of the P450 oxidation, which is dependent on both the substituents on the prodrug moiety, the stereochemistry of these substituents and the drug itself. Moreover, sustained drug production will depend on the rate of elimination of the intermediate generated after oxidation and the rate and availability of the prodrug to the liver, which is the major site of oxidation. Identification of the prodrug with the desired properties is readily achieved by screening the prodrugs in an assay that monitors the rate of drug production in the presence of the major P450 enzyme involved in the metabolism, in the presence of liver microsomes or in the presence of hepatocytes. Standard PK assays (e.g. microsome metabolism, prodrug levels in plasma) indicate that compounds of this invention can be selected for parameters which will improve their ability to achieve "sustained delivery."

Specific Prodrugs of the Invention

The biologically active agent is detected in the liver following administration of drugs of Formula I. Prodrugs of this type undergo oxidation to produce the phosphonic acid, e.g., PMEA, and the aryl vinyl ketone byproduct as shown below:

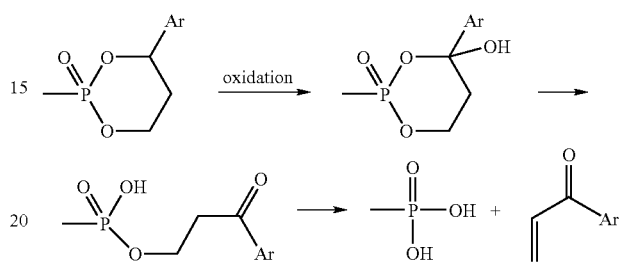

Although the esters in the invention are not limited by the above mechanisms, in general, each ester contains a group or atom susceptible to microsomal oxidation, which in turn generates an intermediate that breaks down to the parent compound in aqueous solution via β-elimination of the phosphonate diacid. It is believed that the hydrogen geminal to the Ar (aryl) group is susceptible to microsomal oxidation.

Use in Treating Liver Cancer

PMEA has been shown to exhibit anticancer activity (Hatse, S., *Verh K. Acad. Geneeskd Belg.* 62(5):373–384 (2000)). Prodrugs of the invention are envisioned to be useful for treating cancers wherein the tumor cells express P450s, especially CYP3A4. For example, prodrugs of this invention are useful in treating hepatocelluar carcinoma or other liver-associated cancers. In some cases, the prodrugs are combined with agents that induce the expression of P450s, especially CYP3A4 in order to enhance activity and/or specificity.

Treatment of Metastatic Cancer:

Prodrugs of this invention may be used in combination with another oncolytic agent. They may be administered separately from the other oncolytic agent or simultaneously with the other oncolytic agent. This combination may help prevent further growth of the hepatocellular carcinoma tumor and/or the combination may help both the hepatocelluar carcinoma tumor (primarily with compounds of this invention) and extrahepatic metastases, especially metastases that have decreased CYP3A4 expression (with the other oncolytic agent).

Administration of the prodrug may occur at or near the time in which the other oncolytic agent is administered or at a different time.

Treatment of Viral Infections:

PMEA is a known drug with potent activity against hepatitis B virus. Oral administration of PMEA is characterized by low oral bioavailability (<10%) whereas the bis acyloxyalkyl prodrug, bis POM PMEA, exhibits good oral bioavailability and good antiviral activity in a variety of animal models as well as in HBV-infected humans. In humans, doses of bis POM PMEA that achieve the largest viral titer reductions and greatest improvements in liver histology and other parameters of liver function (e.g., 30–60 mg/day) are associated with kidney toxicity whereas lower doses (e.g., 10 mg/day) are reported to show less antiviral activity but no kidney toxicity after one year of therapy.

Prodrugs of this invention achieve higher levels of the biologically active form of PMEA, i.e. PMEApp, in the liver relative to animals treated with bis POM PMEA at equal PMEA molar doses (Example N). At these doses, the prodrugs of this invention also result in significantly lower levels of PMEA in the plasma, kidney and urine. Accordingly, prodrugs of this invention are expected to achieve greater viral titer reductions with less risk of renal toxicity.

Increased viral titer reduction is expected to benefit HBV-infected patients through increased seroconversion and decreased risk of liver damage and chronic liver disease (e.g., cirrhosis and hepatocellular carcinoma). In addition, increased viral titer reduction is associated with decreased generation of viral mutants which are associated with drug resistance.

Another preferred aspect of the invention is the combination of the PMEA prodrugs of this invention with other antiviral agents in order to achieve even greater decreases of viral titer and associated therapeutic benefits. HBV viral DNA has been detected in extrahepatic tissues, including kidney. Extrahepatic HBV may provide virus particles that can infect hepatocytes. Since prodrugs of this invention target the liver, therapies that combine these prodrugs with other anti-HBV drugs is a preferred aspect of this invention, since the drug combination inhibits viral replication in the liver as well as at other sites throughout the body. Moreover, a preferred aspect of this invention is the combination of prodrugs of this invention with other well known agents that result in viral titer reduction (e.g., HBV antibody therapies) and improved viral-directed immune responses, e.g., interferons or pegylated interferons. The combination can also benefit HBV-infected patients through a reduction in the effective dose and therefore decreased side effects associated with the therapy. The drug combination can be administered to the HBV patient at the same time or at different times.

Antiviral drugs useful in the combination include Vidarabine; Zidovudine; Stavudine; Didanosine; ddA; Zalcitabine; L-ddC; L-FddC; L-d4C; Lamivudine; Ribavirin; FIAU; FIAC; BHCG; BvaraU; E-5-(2-bromovinyl)-2'-deoxyuridine; TFT; Zonavir; CDG; DAPD; FDOC; d4C; d4T; DXG; FEAU; FLG; FLT; Clevudine; Coviracil; Entecavir; Cytallene; Oxetanocin A; Oxetanocin G;NK 84–0218; ddAPR; Cyclobut A; Cyclobut G; Floxuridine; dFdC; araC; 5-bromodeoxyuridine; IDU; CdA; F-ara-A; ACV; GCV; Penciclovir; Buciclovir; Foscarnet; PPA; PMEA; PMEDAP; HPMPC; HPMPA; FPMPA; PMPA; araT; FMdC; AICAR; AM365; L-dT; L-dC, beta-L-2'-deoxycytosine, valine prodrug derivatives of beta-L-2'-deoxycytosine; ACH 126,443; ddI; ddA; ddC; MCC478; Interferon alpha; Pegylated interferons; famciclovir; XTL001; HBV DNA vaccine; ICN 2001; Fluor L and D nucleosides; Racivir; Robustaflavone; 9-(arabinofuranosyl)-2,6-diaminopurine; 9-(2'-deoxyribofuranosyl)-2,6-diaminopurine; 9-(2'-deoxy-2'-fluororibofuranosyl)-2,6-diaminopurine; 9-(arabinofuranosyl)guanine; 9-(2'-deoxyribofuranosyl)guanine; 9-(2'-deoxy-2'-fluororibofuranosyl)guanine; interferons-all analogues; human monoclonal antibodies; and non-interferon enhancers, such as Theradigm, thymosin alpha-1 and EHT899.

Prodrugs of this invention may be used in combination with another antiviral agent. Administration of the prodrug may occur at or near the time in which the other antiviral agent is administered or at a different time.

Prodrugs of this invention may be used to treat viral infections of the liver in an animal that is resistant to antiviral therapy when the resistance is a result of mutations in HBV polymerase.

Use of Prodrugs with CYP Inhibitors to Reduce Toxicity and/or Increase Oral Bioavailability In some cases, enhanced CYP activity may lead to unwanted drug metabolism. For example, enhanced activity of CYPs not involved in prodrug activation can result in increased drug metabolism and therefore decreased efficacy. In addition, increased CYP activity in other tissues, e.g., CYP3A4 in the gastrointestinal tract, could result in decreased prodrug absorption and liver drug levels. Inhibitors of CYP activity are known that might be useful in minimizing unwanted drug metabolism. For example, grapefruit juice is known to inactivate gastrointestinal CYP3A4 and to result in enhanced absorption of numerous drugs metabolized by CYP3A4. CYP3A4 inhibitors known to enhance oral bioavailability of drugs include ketoconazole and erythromycin. (Wacher, V. J. et al., *Adv. Drug Deliv. Rev.* 46:89–102 (2001); U.S. Pat. No. 5,665,386; U.S. Pat. No. 5,716,928; U.S. Pat. No. 5,962,522; U.S. Pat. No. 6,004,927; U.S. Pat. No. 6,028,054; U.S. Pat. No. 6,121,234; U.S. Pat. No. 6,180,666). CYP inhibitors are also known for many of the CYP subfamilies that can be useful for attenuating unwanted drug metabolism while maintaining CYP activity important for prodrug cleavage. For example, the CYP3A4 inhibitor TAO was used to modulate cyclophosphamide metabolism in vivo in a manner that decreased the formation of toxic metabolites that do not contribute to its antitumor activity.

Compounds of the Invention

The compounds of the invention are substituted 6-membered cyclic 1,3-propane diester prodrugs of PMEA and analogues as represented by Formula I:

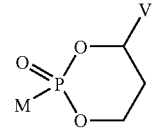

Formula I wherein:
M and V are cis to one another and $MPO_3H_2$ is phosphonic acid selected from a group consisting of 9-(2-phosphonylmethoxyethyl)adenine, (R)-9-(2-phosphonylmethoxypropyl) adenine, 9-(2-phosphonylmethoxyethyl)guanine, 9-(2-phosphonylmethoxyethyloxy)adenine, 9-(2-phosphonylmethoxyethyl)-2,6-diaminopurine, (S)-1-(3-hydroxy-2-phosphonylmethoxypropyl)cytosine, (S)-9-(3-hydroxy-2-phosphonylmethoxypropyl)adenine, 9-(3-hydroxy-2-phosphonylmethoxypropyl)guanine, and (S)-9-(3-fluoro-2-phosphonylmethoxypropyl)adenine;

V is selected from a group consisting of phenyl, 2-pyridyl, 3-pyridyl, 4-pyridyl, 2-furanyl, 3-furanyl, 2-thienyl, and 3-thienyl, all optionally substituted with 1–3 substituents selected from a group consisting of F, Cl, Br, C1–C3 alkyl, $CF_3$ and $OR^6$;

$R^6$ is selected from the group consisting of C1–C3 alkyl, and $CF_3$;

and pharmaceutically acceptable salts thereof.

Another aspect of the invention are the compounds of Formula II:

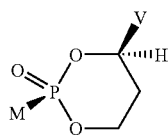

Formula II wherein:

MPO$_3$H$_2$ is a phosphonic acid selected from the group consisting of 9-(2-phosphonylmethoxyethyl)adenine, (R)-9-(2-phosphonylmethoxypropyl)adenine, 9-(2-phosphonylmethoxyethyl)guanine, 9-(2-phosphonylmethoxyethyloxy)adenine, 9-(2-phosphonylmethoxyethyl)-2,6-diaminopurine, (S)-1-(3-hydroxy-2-phosphonylmethoxypropyl)cytosine, (S)-9-(3-hydroxy-2-phosphonylmethoxypropyl)adenine, 9-(3-hydroxy-2-phosphonylmethoxypropyl)guanine, and (S)-9-(3-fluoro-2-phosphonylmethoxypropyl)adenine;

V is selected from a group consisting of phenyl, 2-pyridyl, 3-pyridyl, 4-pyridyl, 2-furanyl, 3-furanyl, 2-thienyl, and 3-thienyl, all optionally substituted with 1–3 substituents selected from a group consisting of F, Cl, Br, C1–C3 alkyl, CF$_3$ and OR$^6$;

R$^6$ is selected from group consisting of C1–C3 alkyl, and CF$_3$;

and pharmaceutically acceptable salts thereof.

Another aspect of the invention are the compounds of Formula III:

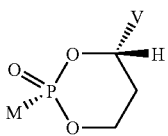

Formula III wherein:

MPO$_3$H$_2$ is a phosphonic acid selected from the group consisting of 9-(2-phosphonylmethoxyethyl)adenine, (R)-9-(2-phosphonylmethoxypropyl)adenine, 9-(2-phosphonylmethoxyethyl)guanine, 9-(2-phosphonylmethoxyethyloxy)adenine, 9-(2-phosphonylmethoxyethyl)-2,6-diaminopurine, (S)-1-(3-hydroxy-2-phosphonylmethoxypropyl)cytosine, (S)-9-(3-hydroxy-2-phosphonylmethoxypropyl)adenine, 9-(3-hydroxy-2-phosphonylmethoxypropyl)guanine, and (S)-9-(3-fluoro-2-phosphonylmethoxypropyl)adenine;

V is selected from a group consisting of phenyl, 2-pyridyl, 3-pyridyl, 4-pyridyl, 2-furanyl, 3-furanyl, 2-thienyl, and 3-thienyl, all optionally substituted with 1–3 substituents selected from a group consisting of F, Cl, Br, C1–C3 alkyl, CF$_3$ and OR$^6$;

R$^6$ is selected from the group consisting of C1–C3 alkyl, and CF$_3$;

and pharmaceutically acceptable salts thereof.

Another aspect of the invention are the compounds of Formula IV:

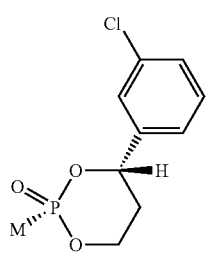

Formula IV wherein:

MPO$_3$H$_2$ is 9-(2-phosphonylmethoxyethyl)adenine;

and pharmaceutically acceptable salts thereof

In another aspect, the invention is directed to compounds of Formulae I, II, III or IV, where MPO$_3$H$_2$ is a phosphonic acid selected from the group consisting of 9-(2-phosphonylmethyloxyethyl) adenine, and (R)-9-(2-phosphonymethoxypropyl) adenine.

In another aspect, the invention is directed to compounds where V is phenyl, 3-pyridyl, and 4-pyridyl, all optionally substituted with 1–2 substituents selected from F, Br, Cl, CH$_3$, OCH$_3$, and CF$_3$.

In another aspect, the invention is directed to compounds where V is 4-pyridyl, 2-bromophenyl, and 3-chlorophenyl.

In another aspect, the invention is directed to compounds of Formula I, II, III, or IV that are salts formed with acetic acid, HBr, HCl, citric acid, maleic acid, sulfuric acid, and tartaric acid.

Another aspect is directed to salts formed with methanesulfonic acid or succinic acid.

Another aspect is directed to salts formed with methanesulfonic acid.

In one aspect, oral bioavailability is at least 5%. In another aspect, oral bioavailability is at least 10%.

P450 oxidation can be sensitive to stereochemistry which might either be at phosphorus or at the carbon bearing the aromatic group (V). The compounds of the present invention have two isomeric forms around the phosphorus. In one aspect, the stereochemistry enables both oxidation and the elimination reaction.

P450 oxidation can also be sensitive to stereochemistry at C1' where V is attached. In one aspect, the compounds of the present invention have S stereochemistry where V is attached.

In one aspect the M groups include 9-(2-phosphonylmethoxyethyl)adenine, (R)-9-(2-phosphonylmethoxypropyl)adenine, 9-(2-phosphonylmethoxyethyl)guanine, 9-(2-phosphonylmethoxyethyloxy)adenine, 9-(2-phosphonylmethoxyethyl)-2,6-diaminopurine, (S)-1-(3-hydroxy-2-phosphonylmethoxypropyl)cytosine, (S)-9-(3-hydroxy-2-phosphonylmethoxypropyl)adenine, 9-(3-hydroxy-2-phosphonylmethoxypropyl)guanine, and (S)-9-(3-fluoro-2-phosphonylmethoxypropyl)adenine. More preferred are 9-(2-phosphonylmethoxyethyl)adenine, and (R)-9-(2-phosphonylmethoxypropyl)adenine.

In one aspect, antiviral agents for use in the combination therapy with the compounds of Formula I include: Vidarabine; Zidovudine; Stavudine; Didanosine; ddA; Zalcitabine; L-ddC; L-FddC; L-d4C; Lamivudine; Ribavirin; FIAU; FIAC; BHCG; BvaraU; E-5-(2-bromovinyl)-2'-deoxyuridine; TFT; Zonavir; CDG; DAPD; FDOC; d4C; d4T; DXG;

FEAU; FLG; FLT; Clevudine; Coviracil; Entecavir; Cytallene; Oxetanocin A; Oxetanocin G;NK 84–0218; ddAPR; Cyclobut A; Cyclobut G; Floxuridine; dFdC; araC; 5-bromodeoxyuridine; IDU; CdA; F-ara-A; ACV; GCV; Penciclovir; Buciclovir; Foscarnet; PPA; PMEA; PMEDAP; HPMPC; HPMPA; FPMPA; PMPA; araT; FMdC; AICAR; AM365; L-dT; L-dC, beta-L-2'-deoxycytosine, valine prodrug derivatives of beta-L-2'-deoxycytosine; ACH 126,443; ddI; ddA; ddC; MCC478; Interferon alpha; Pegylated interferons; famciclovir; valine prodrug derivatives of beta-L-2'-deoxycytosine; XTL001; HBV DNA vaccine; ICN 2001; Fluor L and D nucleosides; Racivir; Robustaflavone; 9-(arabinofuranosyl)-2,6-diaminopurine; 9-(2'-deoxyribofuranosyl)-2,6-diaminopurine; 9-(2'-deoxy-2'-fluororibofuranosyl)-2,6-diaminopurine; 9-(arabinofuranosyl)guanine; 9-(2'-deoxyribofuranosyl)guanine; 9-(2'-deoxy 2'-fluororibofuranosyl)guanine; interferons-all analogues; human monoclonal antibodies; and non-interferon enhancers, such as Theradigm, thymosin alpha-1 and EHT899.

In another aspect, antiviral agents include: lamivudine, entecavir, coviracil, DAPD, clevudine, AM365, L-dT, L-dC, ACH 126,443, MCC478, lobucavir, foscarnet, PPA, interferon alpha, pegylated interferon alfa, fameiclovir, ara-A, AZT, d4T, ddI, ddA, ddC, L-ddC, L-FddC, L-d4C, Lamivudine, Ribavirin, FIAU, FIAC, BHCG, BvaraU, E-5-(2-bromovinyl)-2'-deoxyuridine, TFT, zonavir, CDG, FDOC, d4C, DXG, FEAU, FLG, FLT, FTC, 5-yl-carbocyclic 2'deoxyguanosine, Oxetanocin A, Oxetanocin G, ddAPR, Cyclobut A, Cyclobut G, dFdC, IDU, araT, ddAPR, Foscarnet; PMEDAP, HPMPC, HPMPA, FPMPA, PMPA, ACV, GCV, Penciclovir, 9-(arabinofuranosyl)-2,6-diaminopurine, 9-(2'-deoxyribofuranosyl)-2,6-diaminopurine, 9-(2'-deoxy-2'-fluororibofuranosyl)-2,6-diaminopurine, 9-(arabinofuranosyl)guanine, 9-(2'-deoxyribofuranosyl)guanine, and 9-(2'-deoxy 2'-fluororibofuranosyl)guanine.

In another aspect, antiviral agents include: lamivudine, entecavir, coviracil, DAPD, clevudine, AM365, L-dT, L-dC, ACH 126,443, MCC478, lobucavir, foscarnet, PPA, interferon alpha, and pegylated interferon alfa.

In another aspect, antiviral agents include interferons-all analogues, human monoclonal antibodies, and non-interferon enhancers, such as Theradigm, thymosin alpha-1 and EHT899.

In one aspect, oncolytic agents for use in the combination therapy with the compounds of Formula I include: agents that alkylate DNA, including alkylating agents such as busulfan, carboplatin, temozolomide, thiotepa, cisplatin, miriplatin, and nitrogen mustards such as melphalan, ifosfamide, cyclophosphamide, chlorambucil, and nechlorethamine.

Agents that are from the antibiotic class of oncolytic drugs, including doxorubicin, duanorubicin, actinomycin D, epirubicin, idarubicin, plicamycin, pentostatin, mitoxantrone, valrubicin, and dactinomycin.

Agents that are from the antimetabolite class of oncolytic drugs, including cytarabine, fludarabine, gemcitabine, floxuridine, fluorouracil, cladribine, mercaptopurine, thioguanine, capecitabine, methotrexate, and mitomycin.

Other well known oncolytic agents include dacarbazine, mitoxantrone, piroxantrone, bleomycin, epipodophyllotoxins, such as etoposide and teniposide, vinca alkaloids, including vincrisitne, and vinblastine, taxanes, including paclitaxel, docetaxel, the tecan class, including camptothecin, irinotecan, 9-aminocamptothecin, topotecan, and lurotecan.

In another aspect, oncolytic agents include: agents that alkylate DNA, including alkylating agents such as busulfan, carboplatin, temozolomide, thiotepa, cisplatin, miriplatin, and nitrogen mustards such as melphalan, ifosfamide, cyclophosphamide, and chlorambucil.

Agents that are from the antibiotic class of oncolytic drugs, including doxorubicin, duanorubicin, epirubicin, idarubicin, plicamycin, valrubicin, and dactinomycin.

Agents that are from the antimetabolite class of oncolytic drugs, including gemcitabine, floxuridine, fluorouracil, mercaptopurine, thioguanine, capecitabine, methotrexate, and mitomycin.

Other oncolytic agents including etoposide, paclitaxel, docetaxel, irinotecan, topotecan, and lurotecan.

In another aspect, oncolytic agents include: doxorubicin, gemcitabine, irinotecan, and cisplatin.

Synthesis of Compounds of Formula I

Acyclic nucleoside phosphonate antivirals such as (S)-1-(3-hydroxy-2-phosphonyl-methoxy propyl) cytosine (HPMPC, cidofovir); 9-(2-phosphonyl methoxyethyl) adenine (PMEA, adefovir); (R)-9-(2-phosphonylmethoxy propyl) adenine (PMPA, Tenofovir) and their analogues are well described in literature. (Naesens and De Clercq, *Nucleosides Nucleotides* 16:983 (1997); Naesens et al., *Antiviral Chem Chemother,* 8:23, (1997); Bronson, et al., *Nucleotide Analogues as Antiviral Agents*, ACS symposium series 401, Martin, J. C., Ed., American Chemical Society (1989)).

Synthesis of the compounds encompassed by the present invention includes the following steps: (I) synthesis of prodrugs of acyclic nucleoside phosphonates; (II) synthesis of 1-(aryl)propane-1,3-diol.

1. Synthesis of Prodrugs of Acyclic Nucleoside Phosphonates:

Prodrugs can be introduced at different stages of synthesis of acyclic nucleoside phosphonates. Most often they are made at a later stage, because of their lability. Advantageously, when chemical stability is not an issue during subsequent reaction conditions, the prodrug can be introduced at an earlier stage of synthesis. The synthesis of prodrugs of acyclic nucleoside phosphonates is further organized into: 1) synthesis of prodrugs via parent phosphonic acids, 2) synthesis of prodrugs via parent drug esters by trans-esterification, and 3) synthesis of prodrugs starting from cyclic phosphonate moiety.

1.1. Synthesis of Prodrugs via Parent Phosphonic Acids:

Phosphonate prodrugs are synthesized by reaction of the dichlorophosphonate generated in situ and an alcohol. For example, the reaction of dichlorophosphonate of $MPO_3H_2$ 1 with substituted 1,3-diols in the presence of a base (such as pyridine, triethylamine, etc) yields compounds of Formula I–III (Khamnei, et al., *J. Med. Chem.* 39:4109 (1996)).

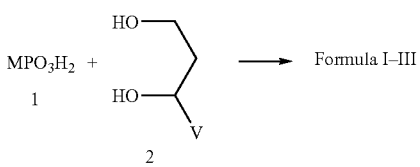

Such reactive dichlorophosphonate intermediates can be prepared from the corresponding phosphonic acids and chlorinating agents, e.g. thionyl chloride (Starrett, et al., *J. Med. Chem.* 1857 (1994)), oxalyl chloride (Stowell, et al, *Tetrahedron Lett.* 31:3261 (1990)), and phosphorus pentachloride (Quast, et al., *Synthesis* 490 (1974)). Alternatively, these dichlorophosphonates can also be generated from disilyl phosphonate esters (Bhongle, et al., *Synth. Commun.* 17:1071 (1987)) and dialkyl phosphonate esters (Still, et al., *Tetrahedron Lett.* 24:4405 (1983); Patois, et al., *Bull. Soc. Chim. Fr.* 130:485 (1993)).

Alternatively, these prodrugs are prepared from phosphonic acids by coupling with diols under Mitsunobu reaction conditions (Mitsunobu, *Synthesis* 1 (1981); Campbell, *J. Org. Chem.* 52:6331 (1992)), and other acid coupling reagents including, but not limited to, carbodiimides (Alexander, et al., *Collect. Czech. Chem. Commun.* 59:1853 (1994); Casara, et al., *Bioorg. Med. Chem. Lett.* 2:145 (1992); Ohashi, et al., *Tetrahedron Lett.* 29:1189 (1988)), and benzotriazolyloxytris-(dimethylamino) phosphonium salts (Campagne, et al, *Tetrahedron Lett.* 34, 6743 (1993)).

Phosphonic acids also undergo cyclic prodrug formation with cyclic acetals or cyclic. ortho esters of 1-substituted propane-1,3-diols to result in prodrugs as in the case of carboxylic acid esters (Brechbuhler, et al., *Helv. Chim. Acta.* 48:1746 (1965)). Alternatively, more reactive cyclic sulfites or sulfates are also suitable as coupling precursors when reacted with phosphonic acid salts. These precursors can be made from the corresponding diols as described in the literature.

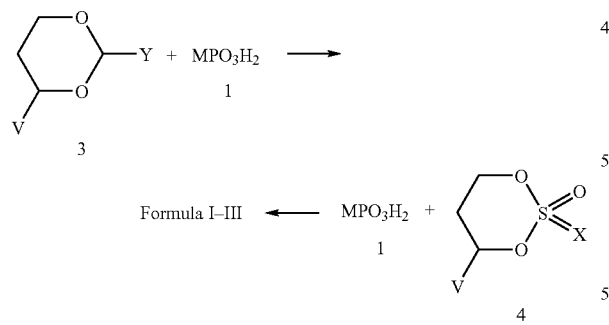

Y = —NMe$_2$, —OMe;
X = O or null

Optically pure prodrugs and corresponding salts are also made starting from optically pure diols which are synthesized as described in the following section 2. These prodrug syntheses are accomplished in three steps from parent phosphonic acids.

In the first step, chlorination of PME, PMP, HPMP analogues, is achieved using oxalyl chloride and N,N-diethylformamide to give N-protected-dichloridate. A variety of other chlorinating agents such as thionyl chloride, phosphorus pentachloride in presence of N,N-dialkyl formamides are also used for the purpose. N,N-dialkylformamide used in the chlorination step not only forms a Vilsmeyer chlorinating agent, but also protects the NH$_2$ group. The protected chloridate intermediate results in favorable solubility properties necessary to improve the overall yield and diastereomeric ratio of the product. Use of other protecting groups, such as acyl, alkoxycarbonyl, aryloxycarbonyl, aralkyloxycarbonyl, Fmoc, etc., may also enhance the recovery and diastereomeric ratio of the desired product.

Coupling of chloridate intermediate and chiral alcohol in the presence of a base (e.g., triethylamine) in dichloromethane at lower temperature results in a protected intermediate. Deprotection of the protected intermediate under mild acidic conditions, in presence of ethanol-acetic acid followed by acidification (e.g., methanesulfonic acid) gives rise to prodrug as a crystalline salt with high chemical purity. A second crystallization of this material to further purify from trans isomer in solvents such as ethanol gives prodrug in >96% diastereomeric purity. The use of other acids, including and not limited to, mineral acids, such as, sulfuric, nitric, hydrochloric, phosphoric, sulfonic acids, such as, alkyl and aryl sulfonic acids, and carboxylic acids, such as, tartaric, citric, maleic, malic, malonic, lactic, oxalic acids and the like, may lead to better recovery and isomeric ratio of the product.

1.2. Synthesis of Prodrugs via Parent Drug Esters by Trans-Esterification:

Phosphonate esters, such as 5 are also utilized in preparation of prodrugs by trans esterification reaction with 1-substituted propane diol under suitable conditions. Mixed anhydride of parent phosphonic acids generated in situ under appropriate conditions react with diols to give prodrugs as in the case of carboxylic acid esters (Inanaga, et al., *Bull. Chem. Soc. Jpn.* 52:1989 (1979)). The resulting derivatives are unmasked to give the required prodrugs. Aryl esters of phosphonates are also known to undergo transesterification with alkoxy intermediates (Moriarty, et al., *Tetrahedron Lett.* 38:2597 (1997); Tawfik, et al., *Synthesis* 968 (1993)). Generation of the prodrugs under such mild conditions may be advantageous in improving diastereomeric ratio.

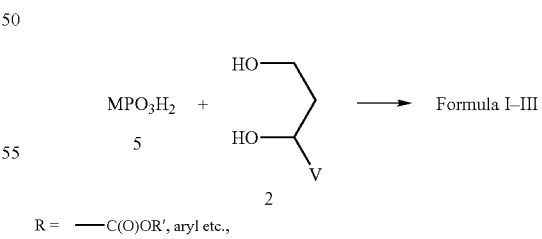

R = —C(O)OR', aryl etc., 1.3. Synthesis of Prodrugs Starting from Cyclic Phosphonate Moiety:

Prodrug moiety can also be introduced at an earlier stage in the synthesis. Advantageously, such syntheses allow definition of the stereochemistry of prodrugs earlier in the synthesis. Phosphonate intermediate 6 containing a leaving group X may be utilized in the case of phosphonomethylenoxyethyl substituted drugs 8 (Chu, et al., *J. Het. Chem.* 23:289 (1986)).

The cyclic phosphonate prodrug moiety 6 may be synthesized via diol and phosphonic acid fragment as described in the earlier sections or by formylation of a cyclic phosphite followed by conversion of a hydroxyl group to a leaving group (Phillion, et al., *Tetrahedron Lett.* 27:1477 (1986)). Such stereodefined intermediates can be coupled under mild conditions to appropriately masked hydroxyethylsubstituted bases 7 under mild conditions to prepare prodrugs of PME, PMP or HPMP derivatives.

Such convergent synthesis can also be achieved via intermediate 10, which upon coupling with an appropriately masked base 9 results in the required prodrug 8. Intermediate 10 containing cyclic prodrug moiety may be synthesized via Arbuzov reaction of cyclic Arbuzov chlorophosphonate (Holy, et al., *Antiviral Res.* 13:295 (1990)) with corresponding chloromethyl ether derivatives.

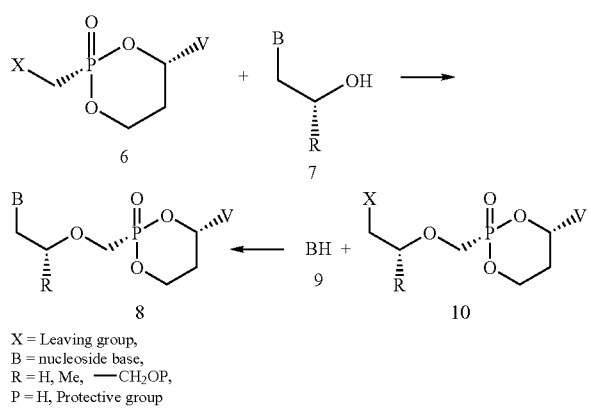

X = Leaving group,
B = nucleoside base,
R = H, Me, —CH$_2$OP,
P = H, Protective group Prodrug stereochemistry (cis- and trans-) is defined by chemical shift of benzylic methine proton in proton NMR spectra. The cis-isomer benzylic methine proton is consistently more deshielded and downfield (with a difference of 0.2 ppm) than corresponding trans-isomer. The difference is enhanced in polar NMR solvents such as DMSO-d6. The isomers can also be differentiated by phosphorus NMR chemical shifts.

2. Synthesis of 1-(Aryl)-Propane-1,3-Diols:

A variety of synthetic methods are known to prepare 1,3-diols. These suitable methods are divided into two types as following: 1) synthesis of racemic 1-(aryl)-propane-1,3-diol; 2) synthesis of chiral 1-(aryl)-propane-1,3-diol.

2.1. Synthesis of Racemic 1-(Aryl)-Propane-1,3-Diols:

1,3-Dihydroxy compounds can be synthesized by several well known methods in literature. Substituted aromatic aldehydes are utilized to synthesize racemic 1-(aryl)-propane-1,3-diol via addition of lithium enolate of alkyl acetate followed by ester reduction (path A) (Turner, *J. Org. Chem.* 55:4744 (1990)). Alternatively, aryl Grignard additions to 1-hydroxy propan-3-al also give 1-aryl-substituted propan-1,3-diols (path B). This method will enable conversion of various substituted aryl halides to 1-arylsubstituted-1,3-propane diols (Coppi, et al, *J. Org. Chem.* 53:911 (1988)).

Aryl halides can also be used to synthesize 1-substituted propane diols by Heck coupling of 1,3-diox-4-ene followed by reduction and hydrolysis (Sakamoto, et al, *Tetrahedron Lett.* 33:6845 (1992)). Pyridyl, quinoline, isoquinoline propan-3-ol derivatives can be oxygenated to 1-substituted-1,3-diol by N-oxide formation followed by rearrangement in acetic anhydride conditions (path C) (Yamamoto, et al., *Tetrahedron* 37:1871 (1981)). A variety of aromatic aldehydes can also be converted to 1-substituted-1,3-diols by vinyl Grignard addition followed by hydroboration reaction (path D).

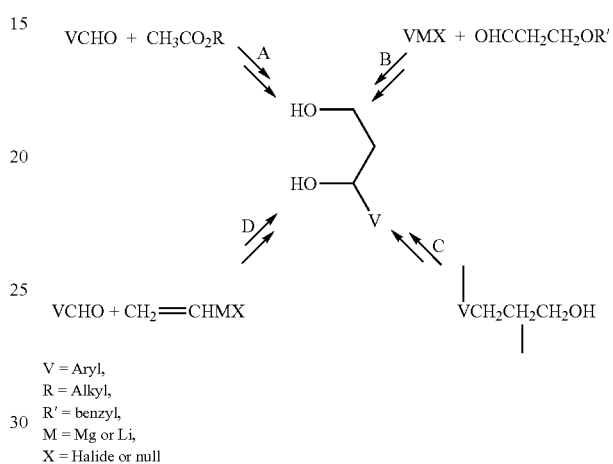

V = Aryl,
R = Alkyl,
R' = benzyl,
M = Mg or Li,
X = Halide or null 2.2. Synthesis of Chiral 1-(aryl)-Propane-1,3-Diols:

A variety of known methods for chiral resolution of secondary alcohols via chemical or enzymatic agents may be utilized for preparation of diol enantiomers (Harada, et al., *Tetrahedron Lett.* 28:4843 (1987)). Transition metal catalyzed hydrogenation of substituted 3-aryl-3-oxo propionic acids or esters is an efficient method to prepare R or S isomers of optically pure beta hydroxy acids or esters (*Comprehensive Asymmetric Catalysis*, Jacobsen, E. N., Pfaltz, A., Yamamoto, H. (Eds), Springer, (1999); *Asymmetric Catalysis in Organic Synthesis*, Noyori, R., John Wiley, (1994)). These beta hydroxy acid or ester products can be further reduced to give required chiral 1-(aryl)-propane-1, 3-diols. (path A). The β-keto acid or ester substrates for high pressure hydrogenation or hydrogen transfer reactions may be prepared by a variety of methods such as condensation of acetophenone with dimethylcarbonate in the presence of a base (Chu, et al., *J. Het. Chem.* 22:1033 (1985)), by ester condensation (Turner, et al., *J. Org. Chem.* 54:4229 (1989)) or from aryl halides (Kobayashi, et al., *Tetrahedron Lett.* 27:4745 (1986)). Alternatively, enantiomerically pure 1,3-diols can be obtained by chiral borane reduction of β-hydroxyethyl aryl ketone derivatives or β-keto acid derivatives (path B) (Ramachandran, et al., *Tetrahedron Lett.* 38:761 (1997)). In another method, commercially available cinnamyl alcohols may be converted to epoxy alcohols under catalytic asymmetric epoxidation conditions. These epoxy alcohols are reduced by Red-A1 to result in enantiomerically pure 1,3-diols (path C) (Gao, et al., *J. Org. Chem.* 53:4081 (1980)). Aldol condensation is another well described method for synthesis of the chiral 1,3-oxygenated functionality starting from aromatic aldehydes. (path D) (Mukaiyama, *Org. React.* 28:203 (1982)).

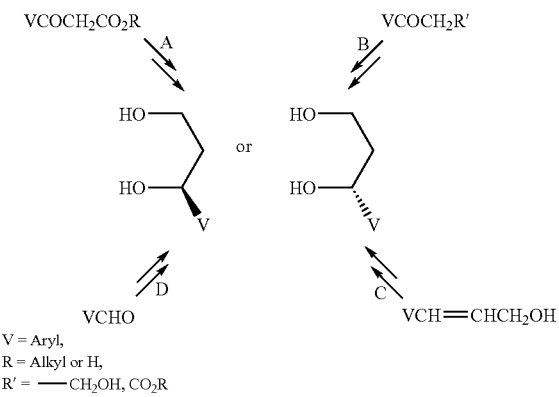

V = Aryl,
R = Alkyl or H,
R' = ——CH$_2$OH, CO$_2$R

Formulations

Compounds of the invention are administered orally in a total daily dose of about 0.01 mg/kg/dose to about 30 mg/kg/dose, preferably from about 0.05 mg/kg/dose to about 10 mg/kg/dose. The most preferred dose range is from 0.1 to 3 mg/kg. The use of time-release preparations to control the rate of release of the active ingredient may be preferred. The dose may be administered in as many divided doses as is convenient.

Compounds of this invention when used in combination with other antiviral agents or oncolytic agents may be administered as a daily dose or an appropriate fraction of the daily dose (e.g. bid). Administration of the prodrug may occur at or near the time in which the other antiviral or oncolytic agent is administered or at a different time.

For the purposes of this invention, the compounds may be administered by a variety of means including orally, parenterally, by inhalation spray, topically, or rectally in formulations containing pharmaceutically acceptable carriers, adjuvants and vehicles. The term parenteral as used here includes subcutaneous, intravenous, intramuscular, and intraarterial injections with a variety of infusion techniques. Intraarterial and intravenous injection as used herein includes administration through catheters. Oral administration is generally preferred.

Pharmaceutically acceptable salts include acetate, adipate, besylate, bromide, camsylate, chloride, citrate, edisylate, estolate, fumarate, gluceptate, gluconate, glucoranate, hippurate, hyclate, hydrobromide, hydrochloride, iodide, isethionate, lactate, lactobionate, maleate, mesylate, methylbromide, methylsulfate, napsylate, nitrate, oleate, pamoate, phosphate, polygalacturonate, stearate, succinate, sulfate, sulfosalyicylate, tannate, tartrate, terphthalate, tosylate, and triethiodide.

Oxalate salts are not pharmaceutically acceptable, but oxalate salts can be used as intermediates. As intermediates, oxalate salts often improve yields.

Pharmaceutical compositions containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain 20 to 2000 μmol (approximately 10 to 1000 mg) of active material compounded with an appropriate and convenient amount of carrier material which may vary from about 5 to about 95% of the total compositions. It is preferred that the pharmaceutical composition be prepared which provides easily measurable amounts for administration. For example, an aqueous solution intended for intravenous infusion should contain from about 0.05 to about 50 μmol (approximately 0.025 to 25 mg) of the active ingredient per milliliter of solution in order that infusion of a suitable volume at a rate of about 30 mL/hr can occur.

As noted above, formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropyl methylcellulose in varying proportions to provide the desired release profile. Tablets may optionally be provided with an enteric coating, to provide release in parts of the gut other than the stomach. This is particularly advantageous with the compounds of Formula 1 when such compounds are susceptible to acid hydrolysis.

Formulations suitable for topical administration in the mouth include lozenges comprising the active ingredient in a flavored base, usually sucrose and acacia or tragacanth; pastilles comprising the active ingredient in an inert base such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Injection solutions and suspensions may be prepared from sterile powders, granules and tablets of the kind previously described.

Preferred unit dosage formulations are those containing a daily dose or unit, daily sub-dose, or an appropriate fraction thereof, of a drug.

It will be understood, however, that the specific dose level for any particular patient will depend on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those skilled in the art.

EXAMPLES

The compounds used in this invention and their preparation can be understood further by the examples, which illustrate some of the processes by which these compounds are prepared. These examples should not however be construed as specifically limiting the invention and variations of the compounds, now known or later developed, are considered to fall within the scope of the present invention as hereinafter claimed.

Compounds of Formula I–III are prepared according to the literature procedures with modifications and additions well understood by those skilled in the art. The TLC conditions given are utilizing plates of Analtech UNIPLATE, silica gel GHLF, scored 10×20 cm, 250 micron.

Synthesis of Racemic 1-(aryl)propane-1,3-diols:

Example 1

Preparation of 1-(2'-Furanyl) Propane-1,3-Diol via Grignard Addition and Hydroboration To a solution of 2-furaldehyde (3 g, 31.2 mmol) in THF (60 mL) was added 1M vinyl magnesium bromide in THF (34 mL) at 0° C. After stirring for an hour, a solution of 1M $BH_3$ THF complex in THF was added. The reaction was quenched with 3N NaOH (20 mL) and 30% hydrogen peroxide (10 mL) at 0° C. The organic fraction was separated and concentrated. The crude product was chromatographed by eluting with 5% methanol-dichloromethane to give 1-(2'-furyl)propane-1,3-diol (1 g, 22%).

Example 2

Preparation of 1-(2'-Pyridyl) Propane-4,3-Diol via Benzylic Oxidation

Step A: (*J. Org. Chem.* 22:589 (1957))

To a solution of 3-(2'-pyridyl)propane-1-ol (10 g, 72.9 mmol) in acetic acid (75 mL) was added 30% hydrogen peroxide slowly. The reaction mixture was heated to 80° C. for 16 h. The reaction was concentrated under vacuum and the residue was dissolved in acetic anhydride (100 mL) and heated at 110° C. overnight. Acetic anhydride was evaporated upon completion of the reaction. Chromatography of the mixture by eluting with methanol-methylene chloride (1:9) resulted in 10.5 g (60%) of pure diacetate.

Step B:

To a solution of diacetate (5 g, 21.1 mmol) in methanol-water (3:1, 40 mL) was added potassium carbonate (14.6 g, 105.5 mmol). After stirring for 3 h at room temperature, the reaction mixture was concentrated. The residue was chromatographed by eluting with methanol-methylene chloride (1:9) to give 2.2 g (68%) of crystalline diol.

Example 3

Preparation of 1-(Aryl)-Propane-1,3-Diol from Propane-1,3-Diol via Grignard Addition Step A: (*J. Org. Chem.* 53:911 (1988))

To a solution of oxalyl chloride (5.7 mL, 97 mmol) in dichloromethane (200 mL) at −78° C. was added dimethyl sulfoxide (9.2 mL, 130 mmol). The reaction mixture was stirred at −78° C. for 20 min before addition of 3-(benzyloxy)propan-1-ol (11 g, 65 mmol) in dichloromethane (25 mL). After an hour at −78° C., reaction was quenched with triethylamine (19 mL, 260 mmol) and warmed to room temperature. Work-up and column chromatography by elution with dichloromethane resulted in 8 g (75%) of 3-(benzyloxy)propan-1-al.

Step B:

To a solution of 3-(benzyloxy)propan-1-al (1 g, 6.1 mmol) in THF at 0° C. was added a 1M solution of 4-fluorophenylmagnesium bromide in THF (6.7 mL, 6.7 mmol). The reaction was warmed to room temperature and stirred for 1 h. Work-up and column chromatography by elution with dichloromethane resulted in 0.7 g (44%) of alcohol.

Step C:

To a solution of benzyl ether (500 mg) in ethyl acetate (10 mL) was added 10% $Pd(OH)_2$-C (100 mg). The reaction was stirred under hydrogen gas for 16 h. The reaction mixture was filtered through celite and concentrated. Chromatography of the residue by elution with ethyl acetate-dichloromethane (1:1) resulted in 340 mg (79%) of product.

Example 4

General Procedure for Preparation of 1-Aryl Substituted Propane-1,3-Diol From Aryl Aldehyde Step A: (*J. Org. Chem.* 55:4744 (1990))

To a −78° C. solution of diisopropylamine (2 mmol) in THF (0.7 ml/mmol diisopropylamine) was slowly added n-butyllithium (2 mmol, 2.5M solution in hexanes). The reaction was then stirred for 15 min at −78° C. before a solution of ethyl acetate (2 mmol) in THF (0.14 ml/mmol ethyl acetate) was slowly introduced. After stirring an additional 30 min at −78° C., a THF solution containing the aryl aldehyde (1.0 mmol in 0.28 ml THF) was added. The reaction was then stirred at −78° C. for 30 min, warmed to room temperature and stirred an additional 2 h. After aqueous work up (0.5 M HCl), the organic layer was concentrated to a crude oil (beta-hydroxyester).

Step B:

The crude hydroxyester was dissolved in ether (2.8 ml/mmol), cooled to ice bath temperature, and lithium aluminum hydride (3 mmol) was added batch wise. The reaction was stirred allowing the cooling bath to melt and the reaction to reach room temperature. After stirring overnight at room temperature, the reaction was cooled back to ice bath temperature and quenched with ethyl acetate. Aqueous work up (0.5M HCl) afforded the crude diol, which was purified either by chromatography or distillation.

Synthesis of Chiral 1-(aryl)-propane-1,3-diols:

Example 5

General Procedure for Resolution of Racemic 1,3-diols

Racemic diols synthesized as in examples 1–4 may be resolved to result in chiral form as described in the following procedure.

Step A:

To a solution of diol (1.0 mmole) in THF (1.0 ml) was added hexamethyldisilazide (2.1 mmole) followed by a catalytic amount of trimethylsilyltriflate (2–3 drops). After stirring at room temperature for 1 h, the reaction was diluted with hexane (4 ml) and subjected to work up with ice-cold water. The resulting disilylether was either purified by chromatography or, if sufficiently pure, used crude in the next reaction.

Step B:

To a solution of disilylether (1.0 mmole) and (−)-menthone (1.1 mmole) in dichloromethane (2.0 ml) at 40° C., was slowly added trimethylsilyltriflate (0.11 mmole). The reaction was then kept at −50 to −60° C. for 48 h, at which time pyridine was added to quench the reaction. After warming to room temperature, the crude mixture was diluted with hexane (4.0 ml) and subjected to aqueous work up. The two ketals were separated by chromatography.

Step C:

The separated ketals were hydrolyzed by adding a catalytic amount of concentrated hydrochloric acid to a methanol (4.0 ml/mmole) solution of each. After stirring overnight at room temperature, the methanol was removed under vacuum and the residue was subjected to aqueous work up. The resolved diols were further purified by either chromatography or distillation.

Example 6

Synthesis of Chiral 3-(3'-Chlorophenyl)-1,3-Dihydoxypropane via Sharpless Asymmetric Epoxidation Step A:

To a dispersion of m-chloro-cinnamic acid (25 g, 137 mmol) in ethanol (275 mL) was added conc. sulphuric acid (8 mL) at room temperature. The reaction was refluxed overnight and concentrated. Ice-cold water was added to the crude and precipitated white solid was filtered and washed with cold water. Precipitate was dried under vacuum overnight to give 25 g (87%) of ester. (Rf=0.50 in dichloromethane on silica)

Step B:

To a solution of m-chlorocinnamic acid ethyl ester (23 g, 109.5 mmol) in dichloromethane at −78° C. was added 1M DIBAL-H in dichloromethane (229 mL, 229 mmol) dropwise over 1 h. The reaction was stirred at −78° C. for an additional 3 h. Ethylacetate was added to quench excess DIBAL-H and saturated aq. potassium sodium tartrate was added and stirred reaction at room temperature for 3 h. Organic layer was separated and salts were washed with ethyl acetate. Combined organic portions were concentrated and distilled at 120° C./0.1 mm to give 14 g (76%) of pure allylic alcohol. (Rf=0.38 in 1:1 ethylacetate:hexane on silica)

Step C:

To a solution of m-chlorocinnamyl alcohol (5 g, 29.76 mmol) in dichloromethane (220 mL) was added activated 4A molecular sieves powder (2.5 g) and the mixture was cooled to −20° C. (+)-Diethyl tartrate (0.61 mL, 3.57 mmol) was added at −20° C. and stirred for 15 min before adding titanium tetraisopropoxide (0.87, 2.97 mmol). The reaction was stirred for additional 30 min and 5–6M t-butylhydroperoxide in heptane (10 mL, 60 mmol) was added dropwise while maintaining the internal temperature at −20 to −25° C. The mixture was stirred for additional 3 h at −20° C. and 10% sodium hydroxide in saturated aq sodium chloride (7.5 mL) followed by ether (25 mL) was added. The reaction was warmed to 10° C. and stirred for 15 min before adding anhydrous magnesium sulphate (10 g) and celite (1.5 g). The mixture was further stirred for additional 15 min, filtered and concentrated at 25° C. to give crude epoxy alcohol. (Rf=0.40 in 1:1 ethylacetate:hexane on silica).

Step D:

To a solution of crude m-chloroepoxycinnamyl alcohol obtained from earlier reaction in dimethoxyethane (300 mL) was added a 65% Red-A1 solution in toluene (18.63 mL, 60 mmol) dropwise under nitrogen at 0° C. After stirring at room temperature for three hours, the solution was diluted with ethyl acetate (400 mL) and quenched with aq saturated sodium sulphate solution (50 mL). After stirring at room temperature for 30 min, the resulting white precipitate formed was filtered and washed with ethyl acetate. The filtrate was dried and concentrated. The crude product was distilled at 125–130° C./0.1 mm to give 3.75 g (67%) of pure (R)-3-(3'-chlorophenyl)-1,3-dihydoxypropane. (Rf=0.40 in 1:1 ethylacetate:dichloromethane) Optical purities were defined as diacetates (prepared by treatment of diols with acetic anhydride, triethylamine, cat.DMAP in dichloromethane) by HPLC ((S,S) Whelko-0, 2.5 cm×4.0 mm ID purchased from Regis).

(R)-3-(3'-chlorophenyl)-1,3-dihydoxypropane: 91% ee (+)Diisopropyltartrate provided >96% ee of (R)-3-(3'-chlorophenyl)-1,3-dihydoxypropane.

(S)-3-(3'-Chlorophenyl)-1,3-dihydoxypropane was also prepared under identical conditions via asymmetric epoxidation and reduction protocol utilizing (−)-tartrate in similar yields.

(S)-3-(3'-Chlorophenyl)-1,3-dihydoxypropane: 79% ee

Example 7

Synthesis of Chiral 3-(3'-Chlorophenyl)-1,3-Dihydoxypropane via Hydrogen Transfer Reaction Step A: Preparation of Methyl 3-(3'-Chlorophenyl)-3-Oxo-Propionate:

A 22 L, 3-neck round bottom flask was equipped with a mechanical stirrer, thermowell/thermometer and nitrogen inlet (bubbler in-line). The flask was flushed with nitrogen and charged sequentially with THF (6 L), potassium t-butoxide (1451 g), and THF (0.5 L). The resulting mixture was stirred at ambient temperature for 15 minutes and a 20° C. water bath was applied. A 3 L round bottom flask was charged with 3'-chloroacetophenone (1000 g) and diethylcarbonate (1165 g), and the resulting yellow solution was added slowly to the stirred potassium t-butoxide solution, maintaining the temperature between 16 and 31° C. After the addition was complete (1 h, 10 min.), the cooling bath was removed and the solution was stirred for 1 h, 30 min. TLC indicated that the reaction was complete. A 5 gallon stationary separatory funnel was charged with ice water (4 L) and concentrated hydrochloric acid (1.3 L of 12 M solution). The dark red reaction solution was quenched into the aqueous acid and the mixture was stirred for 15 minutes. The layers were separated and the aqueous phase (lower) was extracted again with toluene (4 L). The combined organic extracts were washed with saturated brine (2×3 L, 10 minute stirring time each), dried (MgSO$_4$), filtered and concentrated under reduced pressure to provide 1480 g of a brown oil. The oil was placed under high vacuum (10 torr) overnight to give 1427 g. The material was vacuum distilled (short path column, fraction cutter receiver) and the fraction at 108–128° C./1–0.5 torr was collected to provide 1273.9 g of a yellow oil (92.6%). (Rf=0.36 in 20% ethyl acetate/hexanes).

Step B: Preparation of Methyl (S)-3-(3'-Chlorophenyl)-3-Hydroxypropionate:

A 12 L, 3-neck round bottom flask was equipped with a mechanical stirrer, thermometer, addition funnel (500 mL) and nitrogen inlet (bubbler in-line). The flask was flushed with nitrogen and charged with formic acid (292 mL, 350 g). Triethylamine (422 mL, 306 g) was charged to the addition funnel, then added slowly with stirring, maintaining the temperature <45° C. After the addition was complete (1 h, 30 min.), the solution was stirred with the ice bath applied for 20 min., then at ambient temperature for an additional 1 h. The flask was charged sequentially with methyl 3-(3'-chlorophenyl)-3-oxo-propionate (1260 g), DMF (2.77 L including rinsing volume) and (S,S)-Ts-DPEN-Ru-Cl-(p-cymene) (3.77 g). The flask was equipped with a heating mantle and the addition funnel was replaced with a condenser (5° C. circulating coolant for condenser). The stirred reaction solution was slowly heated to 60° C. (90 min. to attain 60° C.) and the contents were maintained at 60° C. for 4.25 h. HPLC indicated 3% starting material remained. The solution was stirred at 60° C. for an additional 8 h, then gradually cooled to ambient temperature overnight. HPLC indicated 0.5% starting material. A 5 gallon stationary separatory funnel was charged with water (10 L) and MTBE (1 L). The reaction solution was poured into the aqueous mixture and the reaction flask was rinsed into the separatory funnel with an additional 1 L of MTBE. The contents were stirred for several minutes and the layers were separated. The aqueous phase was extracted with additional MTBE (2×1 L), and the combined organic extracts were washed with brine (1 L), and concentrated under reduced pressure to provide 1334 g of a red oil (105%). The oil was used without further purification for the next step.

The crude hydroxyester (10 mg, 0.046 mmol) was dissolved in dichloromethane (1 mL). Acetic anhydride (22 μL, 0.23 mmol) and 4-(dimethylamino)pyridine (22 mg, 0.18 mmol) were added and the solution was stirred at ambient temperature for 15 min. The solution was diluted with dichloromethane (10 mL) and washed with 1 M hydrochloric acid (3×3 mL). The organic phase was dried (MgSO$_4$), filtered and concentrated under reduced pressure. The residual oil was dissolved in methanol and analyzed by chiral HPLC (Zorbax Rx-C18, 250×4.6 mm; mobile phase: 65/35 (v/v) water/acetonitrile, isocratic; flow rate=1.5 mL/min; inj. volume=15 μL; UV detection at 220 nm. Retention times: Product=9.3 min, starting material=17.2 min.). The hydroxyester was derivatized to the acetate for analysis by chiral HPLC and shown to give 91% ee. (HPLC conditions: Column: Pirkle covalent (S,S) Whelk-O 10/100 krom FEC, 250×4.6 mm; mobile phase: 70/30 (v/v) methanol/water, isocratic; flow rate: 1.5 mL/min; inj. volume=10 μL; UV detection at 220 nm. Retention times: S-hydroxyester (acetate)=9.6 min, R-hydroxyester (acetate)=7.3 min.)

Step C: Preparation of (S)-3-(3'-Chlorophenyl)-3-hydroxypropanoic Acid:

To the crude hydroxyester in a 10 L rotary evaporator flask was added sodium hydroxide solution (2.5 L of 2 M solution). The resulting solution was stirred on the rotary evaporator at ambient pressure and temperature for 2 h. HPLC indicated 5% starting material still remained (HPLC conditions: Column: Zorbax Rx-C18, 250×4.6 mm; mobile phase: 65/35 (v/v) water/acetonitrile, isocratic; flow rate=1.5 mL/min; inj. volume=15 μL; UV detection at 220 nm. Retention times: Product=3.8 min, starting material=18.9 min.). The pH of the solution was 11 (wide range pH paper). Additional 2 M NaOH solution was added to adjust the pH to 14 (approx. 100 mL), and the solution was stirred for an additional 30 min. HPLC indicated the reaction was complete. The solution was transferred to a 5 gallon stationary separatory funnel and extracted with MTBE (2 L). The layers were separated and the organic extract was discarded. The aqueous phase was transferred back to the separatory funnel and acidified with 12 M HCl solution (600 mL). The mixture was extracted with MTBE (1×2 L, 2×1 L). The combined acidic organic extracts were dried (MgSO$_4$), filtered and concentrated under reduced pressure to give 1262 g of a brown, oily semi-solid. The residue was slurried with ethyl acetate (1 L) and transferred to a 12 L, 3-neck round bottom flask equipped with a mechanical stirrer, heating mantle, condenser and thermometer. The stirred mixture was heated to dissolve all solids (28° C.) and the dark solution was cooled to 10° C. (a precipitate formed at 11° C.). The mixture was slowly diluted with hexanes (4 L over 1 h) and the resulting mixture was stirred at <10° C. for 2 h. The mixture was filtered and the collected solid was washed with cold 4/1 hexanes/ethyl acetate (1 L), and dried to constant weight (−30 in. Hg, 50° C., 4 h). Recovery=837 g of a beige solid (70.4%). mp=94.5–95.5° C.

A 50 mg sample of hydroxyacid was reduced to the diol with borane-THF (see Step D). The resulting crude diol was diacetylated (as described in Step B)) and analyzed by chiral HPLC Retention times: S-diol (diacetate)=12.4 min, R-diol (diacetate)=8.8 min.) ee=98%

A second crop of hydroxyacid was isolated. The filtrate from above was concentrated under reduced pressure to give 260 g of a brown sludge. The material was dissolved in ethyl acetate (250 mL) and the stirred dark solution was slowly diluted with hexanes (1000 mL) and the resulting mixture was stirred at ambient temperature overnight. The mixture was filtered and the collected solid was washed with 5/1 hexanes/ethyl acetate (200 mL), and dried to constant weight (−30 in. Hg, 50° C., 16 h). Recovery=134 g of a beige solid (11.2%). ee=97%

Step D: Preparation of (S)-(−)-1-(3'-Chlorophenyl)-1,3-Propanediol:

A 22 L, 3-neck round bottom flask was equipped with a mechanical stirrer, thermowell/thermometer and nitrogen inlet (outlet to bubbler). The flask was charged with 2M borane-THF (3697 g, 4.2 L) and the stirred solution was cooled to 5° C. A solution of (S)-3-(3-chlorophenyl)-3-hydroxypropanoic acid (830 g) in THF (1245 mL) was prepared with stirring (slightly endothermic). The reaction flask was equipped with an addition funnel (1 L) and the hydroxyacid solution was slowly added to the stirred borane solution, maintaining the temperature <16° C. After the addition was complete (3 h), the mixture was stirred at ice bath temperature for 1.5 h. The reaction was quenched by careful addition of water (2.5 L). After the addition was complete (30 min), 3M NaOH solution (3.3 L) was added (temperature increased to 35° C.) and the resulting mixture was stirred for an additional 20 minutes (temperature=30° C.). The reaction mixture was transferred to a 5 gallon stationary separatory funnel and the layers were separated. The aqueous phase was extracted with MTBE (2.5 L) and the combined organic extracts (THF and MTBE) were washed with 20 wt % NaCl solution (2 L) and stirred with MgSO$_4$ (830 g) for 30 minutes. The mixture was filtered through Celite and concentrated under reduced pressure to provide 735 g of a thick, brown oil.

The oil was purified by vacuum distillation and the fraction at 135–140° C./0.2 mmHg was collected to provide 712.2 g of a colorless oil (92.2%).

The diol was diacetylated and analyzed by chiral HPLC (e.e.=98%) (see Step B). Retention times: S-diol (diacetate) =12.4 min, R-diol (diacetate)=8.9 min. $[\alpha]_D$=−51.374 (5 mg/mL in CHCl$_3$)

Example 8

Synthesis of Chiral 3-(3'-chlorophenyl)-4,3-dihydroxypropane via (−)-β-chlorodiisopinocampheylborane (DIPCI) Reduction Step A: Preparation of 3-(3'-Chlorophenyl)-3-oxo-propanoic Acid:

A 12 L, 3-neck round bottom flask was equipped with a mechanical stirrer and addition funnel (2 L). The flask was flushed with nitrogen and charged with diisopropylamine (636 mL) and THF (1.80 L). A thermocouple probe was immersed in the reaction solution and the stirred contents were cooled to −20° C. n-Butyllithium (1.81 L of a 2.5 M solution in hexanes) was charged to the addition funnel and added slowly with stirring, maintaining the temperature between −20 and −28° C. After the addition was complete (30 min), the addition funnel was rinsed with hexanes (30 mL) and the stirred solution was cooled to 62° C. Trimethylsilyl acetate (300 g) was added slowly with stirring, maintaining the temperature <−60° C. After the addition was complete (30 min), the solution was stirred at −60° C. for 15 min. 3-Chlorobenzoyl chloride (295 mL) was added slowly with stirring, maintaining the temperature <−60° C. After the addition was complete (65 min), the cooling bath was removed and the reaction solution was stirred for 1.25 h, with gradual warming to 0° C. The reaction flask was cooled with an ice bath, then water (1.8 L) was added to the stirred solution. The reaction mixture was stirred for 10 minutes, then diluted with t-butyl methyl ether (1.0 L). The lower aqueous phase was separated and transferred to a 12 L, 3-neck round bottom flask equipped with a mechanical stirrer. t-Butyl methyl ether was added (1.8 L) and the stirred mixture was cooled to <10° C. (ice bath). Concentrated HCl solution (300 mL of 12 M solution) was added and the mixture was vigorously stirred. The layers were separated and aqueous phase was further acidified with conc. HCl (30 mL) and extracted again with t-butyl methyl ether (1.0 L). The combined MTBE extracts were washed with brine (1 L), dried (MgSO$_4$, 70 g), filtered and concentrated under reduced pressure to give 827 g of a yellow solid. The crude solid was slurried in hexanes (2.2 L) and transferred to a 5 L, 3-neck round bottom flask equipped with a mechanical stirrer. The mixture was stirred at <10° C. (ice bath) for 1 h, then filtered, washed with hexanes (4×100 mL) and dried to constant weight (−30 in. Hg, ambient temperature, 14 h). Recovery=309 g of a pale yellow powder (68.6%).

Step B: Preparation of (S)-3-(3'-Chlorophenyl)-3-Hydroxypropanoic Acid:

A 12 L, 3-neck round bottom flask was equipped with a mechanical stirrer and addition funnel (1 L). The flask was flushed with nitrogen and charged with 3-(3'-chlorophenyl)-3-oxo-propanoic acid (275.5 g) and dichloromethane (2.2 L). A thermocouple probe was immersed in the reaction slurry and the stirred contents were cooled to −20° C. Triethylamine (211 mL) was added over 5 minutes to the stirred slurry and all solids dissolved. A dichloromethane solution of (−)-B-chlorodiisopinocampheylborane (1.60 M, 1.04 L) was charged to the addition funnel, then added slowly with stirring, maintaining the temperature between −20 and −25° C. After the addition was complete (35 min), the solution was warmed to ice bath temperature (2–3° C.) and stirred for 4 h. An in-process NMR analysis indicated the starting material was <4%. Water (1.2 L) was added to the cloudy orange reaction mixture, followed by 3 M NaOH solution (1.44 L). The mixture was vigorously stirred for 5 min, then transferred to a separatory funnel. The layers were separated and the basic aqueous phase was washed with ethyl acetate (1.0 L). The aqueous phase was acidified with conc. HCl (300 mL) and extracted with ethyl acetate (2×1.3 L). The two acidic ethyl acetate extracts were combined, washed with brine (600 mL), dried (MgSO$_4$, 130 g), filtered and concentrated under reduced pressure to provide 328 g of a yellow oil (the oil crystallized on standing). The solid was slurried in ethyl acetate (180 mL) and transferred to a 2 L, 3-neck round bottom flask, equipped with a mechanical stirrer. The stirred mixture was cooled to <10° C. (ice bath), then diluted with hexanes (800 mL). The resulting mixture was stirred at ice bath temperature for 4 h, then filtered. The collected solid was washed with 4:1 hexanes: ethyl acetate (3×50 mL) and dried to constant weight (−30 in. Hg, ambient temperature, 12 h). Recovery=207.5 g of a white powder (74.5%).

Step C: Preparation of (S)-(−)-1-(3'-Chlorophenyl)-1,3-Propanediol:

A 12 L, 3-neck round bottom flask was equipped with a mechanical stirrer, addition funnel (2 L) and thermometer. The flask was flushed with nitrogen and charged with (S)-3-(3'-chlorophenyl)-3-hydroxypropanoic acid (206.7 g) and THF (850 mL), and the stirred solution was cooled to 5° C. (ice bath). A 1M borane in THF solution (2.14 L) was charged to the addition funnel, then added slowly with stirring maintaining the temperature <10° C. After the addition was complete (1 h), the cooling bath was removed and the solution was stirred at ambient temperature for 1 h. The reaction solution was slowly and cautiously quenched with water (600 mL), followed by 3 M NaOH solution (850 mL). The mixture was stirred for 10 min, then transferred to a separatory funnel. The layers were separated and the aqueous phase was back extracted with ethyl acetate (600 mL). The combined organic phase was washed with brine (500 mL), dried (MgSO$_4$, 322 g), filtered and concentrated under reduced pressure to provide 189.0 g of a pale yellow oil (101%). The oil was purified by vacuum distillation and the fraction at 125–155° C./0.15 mmHg was collected to provide 180.9 g of a colorless oil (94.0%).

The diol (5.0 mg, 0.026 mmol) was dissolved in dichloromethane (2.0 mL). Acetic anhydride (15 µL, 0.15 mmol) and 4-(dimethylamino)pyridine (13 mg, 0.10 mmol) were added and the solution was stirred at ambient temperature for 15 min. The reaction solution was quenched with 1 M HCl solution (3 mL) and the lower organic phase was separated, passed through a plug of $MgSO_4$, and concentrated with a stream of nitrogen. The residue was dissolved in methanol (1 mL) and analyzed by chiral HPLC (see, Example 7; Step B). ee>98%.

Example 9

The Preparation of 1,3-Diols via Catalytic Asymmetric Hydrogenation

Step A:

Beta-ketoester starting material was synthesized as described in Example 7, step A.

Step B:

A solution containing beta-ketoester (1 mmole) in either methanol or ethanol (5–10 ml/mmole ketoester) was degassed through several pump/vent ($N_2$) cycles at room temperature. The degassed solution was moved into a glove bag and under an atmosphere of $N_2$ was poured into a stainless steel bomb containing a stir bar and 1.0 mole % Ru-BINAP catalyst. The bomb was sealed, removed from the glove bag and purged with $H_2$ prior to stirring 18–24 h at room temperature and 150 psi $H_2$. After venting the hydrogen pressure, the bomb was opened and the reaction mixture was removed and concentrated. The crude beta-hydroxyester was used for hydrolysis.

Step C:

Crude beta-hydroxy ester was hydrolyzed as described in Example 7, step C.

Step D:

Optically active beta-hydroxy acid was reduced as described in Example 7, step D.

Synthesis of Prodrug via Coupling of Phosphonic Acids and 1-(aryl)propane 1,3-diols:

Example 10

General Procedure for Synthesis of Prodrugs by Thionyl Chloride Reaction

A suspension of 1 mmol of phosphonic acid in 5 mL of thionyl chloride was heated at reflux temperature for 4 h. The reaction mixture was cooled and evaporated to dryness. To the resulting residue was added a solution of 1 mmol of diol and 2.5 mmol pyridine in 3 mL of methylene chloride. After stirring at 25° C. for 4 h the reaction was subjected to work up and chromatography.

Example 11

General Procedure for Synthesis of Prodrugs via DCC Coupling

To a solution of PMEA (410 mg, 1.5 mmol) in DMF (15 mL) and pyridine (3 mL) was added 1,3-dicyclohexylcarbodiimide (DCC) (925 mg, 4.5 mmol) followed by 1(3-chlorophenyl)propane-1,3-diol from Step B (295 mg, 1.57 mmol). The reaction mixture was heated overnight at 100° C. The mixture was concentrated under reduced pressure and azeotroped with toluene (2×10 mL). Crude compound was chromatographed on a silica gel column (3:97 to 10:90 methanol-dichloromethane) to result in pure cyclic prodrug (310 mg).

Synthesis of Prodrugs via Oxalyl Chloride Mediated Coupling

Example 12

Preparation 9-{2-[2,4-cis-(S)-(+)-4-(3'-Chlorophenyl)-2-oxo-4,3,2-dioxaphosphorinan-2-yl]methoxyethyl}Adenine MethaneSulfonate (18)

Example 12.1

Formation of Dichloridate (11)

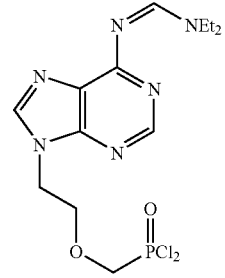

11

A 2L, 3-neck round bottom flask was equipped with a mechanical stirrer, condenser, addition funnel (125 mL) and heating mantle. The flask was flushed with nitrogen and charged with PMEA (50.0 g), dichloromethane (650 mL) and N,N-diethylformamide (22.5 mL). Oxalyl chloride (58.0 mL) was charged to the addition funnel, and added slowly to the stirred reaction mixture. After the addition was complete (15 minutes), the addition funnel was removed and the vigorously stirred mixture was heated at reflux for 2 hours. The solution remained a slurry during this process. The reaction mixture was cooled slightly, and additional oxalyl chloride (1.0 mL) and N,N-diethylformamide (0.4 ml) were added. The addition of N,N-diethylformamide produced vigorous gas evolution. The resulting mixture was heated at reflux until all solids were dissolved (additional 2.5 hours, total reaction time was approximately 4.5 hours). HPLC analysis of the reaction solution indicated the product 11 at 83 Area %. The reaction was monitored for formation of the dichloridate. A sample of the reaction mixture (approximately 50 µL) was removed and quenched in anhydrous methanol (1L) containing 1 drop of triethylamine. The resulting methyl phosphonate(s) were analyzed by HPLC.

HPLC Conditions:

YMC-Pack R & D, R-33–5 S-5 120A, 250×4.6 mm; mobile phase: Solvent A=20 mM potassium phosphate, pH 6.2; Solvent B=acetonitrile; gradient: 10–60%B/15 min., 60–10% B/2 min., 10% B/3 min.; 1.4 mL/min.; inj. vol.=10 μL; UV detection at 270 nm.

Retention Times:

Dimethylphosphonate 12=8.5 min., monomethyl phosphonate 13=5.8 min.

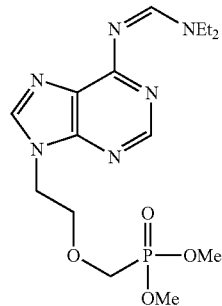

12

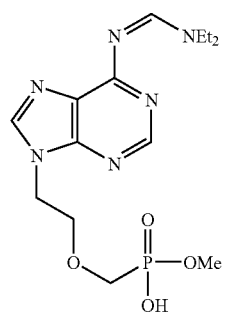

13

The reaction solution was cooled slightly and the condenser was replaced with a distillation head with thermometer, condenser and collection flask (250 mL). The reaction solution was heated to reflux and 250 mL of distillate was collected. The pot solution was diluted with dichloromethane (250 mL) and an additional 250 mL of distillate was collected. The distillation head was removed and the reaction flask was placed under nitrogen. The solution was diluted with dichloromethane (100 mL) and cooled to ice bath temperature. HPLC analysis of the reaction solution indicated the product at 89 area %.

HPLC Conditions:

YMC-Pack R & D, R-33–5 S-5 120A, 250×4.6 mm; mobile phase: Solvent A=20 mM potassium phosphate, pH 6.2; Solvent B=acetonitrile; gradient: 10–60% B/15 min., 60–10% B/2 min., 10% B/3 min.; 1.4 mL/min.; inj. vol.=10 μL; UV detection at 270 nm.

Retention Times: Product 11=8.5 min., starting material=5.9 min

Pyridine (18 mL) was added slowly to the stirred solution. After the addition was complete (5 minutes), the resulting pale orange solution was stored at ice bath temperature until used (30 minutes).

Example 12.2

Coupling Reaction

A 2L, 3-neck round bottom flask was equipped with a mechanical stirrer, and addition funnel (1L). The flask was flushed with nitrogen and charged with (S)-(−)-(3'-chlorophenyl)-1,3-propanediol (34.1 g), as a solution in dichloromethane (500 mL) and triethylamine (125 ml). A thermocouple probe was immersed in the reaction solution and the stirred contents were cooled to −71° C. (dry ice/isopropanol). The dichloridate solution 11 was charged to the addition funnel, then added slowly with stirring, maintaining the temperature <−67° C. After the addition was complete (1.25 h), the cooling bath was removed and the stirred mixture was warmed to 0° C. over 30 min. The reaction mixture was washed with water (550 mL) and the layers were separated. The dichloromethane phase was diluted with ethyl acetate (500 mL) and washed with 5% NaCl solution (600 mL). The organic phase was dried (MgSO$_4$, 50 g), filtered through diatomaceous earth (Celite 521), and concentrated under reduced pressure to provide 108 g of a dark red sludge. The samples were dissolved in methanol.

HPLC Conditions:

YMC-Pack R & D, R-33–5 S-5 120A, 250×4.6 mm; mobile phase: Solvent A=20 mM potassium phosphate, pH 6.2; Solvent B=acetonitrile; gradient: 10–60% B/15 min., 60–10% B/2 min., 10% B/3 min.; 1.4 mL/min.; inj. vol.=10 μL; UV detection at 270 nm.

Retention Times: cis 14=12.5 min., trans 15=13.0 min.

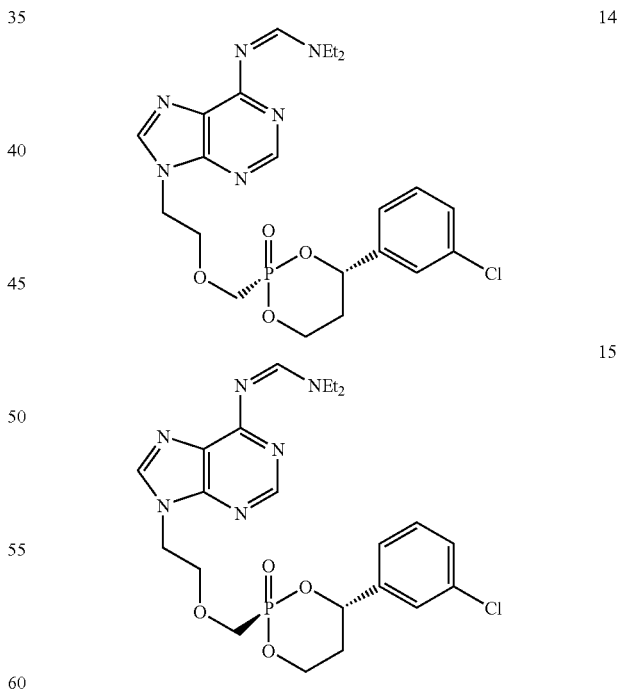

The material was dissolved in ethanol (500 mL) and transferred to a 2 L round bottom flask equipped with magnetic stirring, condenser and heating mantle. Acetic acid (55 mL) was added and the red solution was heated at reflux for 8 hours. HPLC indicated the reaction was complete. The samples were dissolved in methanol.

HPLC Conditions:

YMC-Pack R & D, R-33–5 S-5 120A, 250×4.6 mm; mobile phase: Solvent A=20 mM potassium phosphate, pH 6.2; Solvent B=acetonitrile; gradient: 10–60% B/15 min., 60–10% B/2 min., 10% B/3 min.; 1.4 mL/min.; inj. vol.=10 μL; UV detection at 270 nm.

Retention Tmes: cis 16=9.5 min., trans 17=9.8 min.

μL; UV detection at 260 nm; sample preparation=2.0 mg/mL in water. Retention times: cis-(R)-9-(2-Hydroxyethyl)adenine=24.6 min., trans-(R)-9-(2-diethylphosphonylmethoxyethyl)adenine=27.5 min., cis-(S)-9-(2-Phosphonylmethoxyethyl)adenine=18.0 min.

$^1$H NMR (D$_2$O) was used to confirm structure of components.

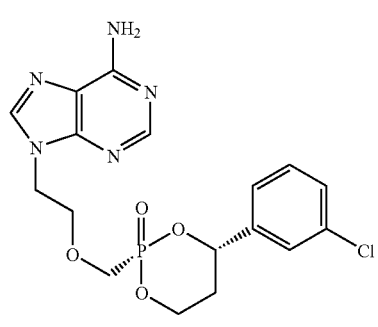

Example 12.3

Crystallization of 9-{2-[2,4-cis-(S)-(+)-4-(3'-Chlorophenyl)-2-oxo-1,3,2-dioxaphosphorinan-2-yl]metboxyethyl}adenine Methanesulfonate (18)

Methanesulfonic acid (21.5 mL) was added and a precipitate formed after 15 min. The mixture was diluted with ethanol (400 mL) and heated until all solids dissolved (pot temperature=70° C.). The solution was cooled with stirring and a precipitate formed at 46° C. The resulting mixture was stirred for 2 h, with cooling to ambient temperature, then at ice bath temperature for 2.5 h. The mixture was filtered and the collected solid was washed with ethanol (2×15 mL) and dried to constant weight (–30 in. Hg, 55° C., 14 h). Recovery=49.4 g of a white powder 18 (51.9%). The solid contained 6.5 area % of the trans diastereomer.

Chiral HPLC: Pirkle covalent (S,S) Whelk-O 1 10/100 krom FEC 250×4.6 mm; mobile phase=55:45, methanol: 0.1% HOAc in water; isocratic; 1.0 mL/min.; inj. vol.=10

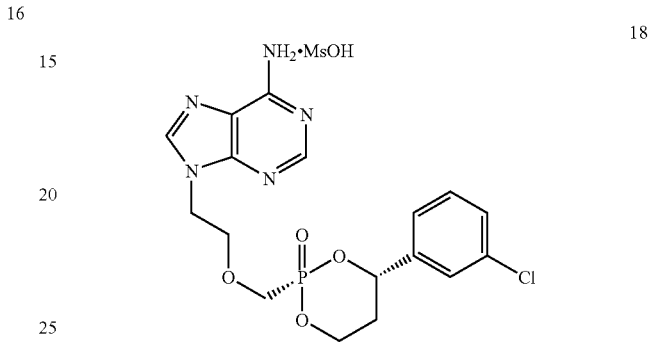

Example 12.4

Recrystallization of 9-{2-[2,4-cis-(S)-(+)-4-(3'-Chlorophenyl)-2-oxo-1,3,2-dioxapbosphorinan-2-yl]methoxyethyl}adenine Methanesulfonate (18)

A 3L, 3-neck round bottom flask was equipped with a mechanical stirrer, condenser, heating mantle and thermometer. The flask was charged with 2 batches of crude mesylate salt 18 and ethanol (1.4 L). The stirred mixture was heated at reflux (pot temperature was 78° C.) until all solids dissolved (approximately 10 minutes). The stirred mixture was gradually cooled to ambient temperature over 1.5 hours (a precipitate formed at 56° C.). The mixture was stirred at ambient temperature for an additional 2 hrs., then filtered. The collected solid was washed with ethanol (2×15 mL) and dried to constant weight (–30 in Hg, 65° C., 60 hrs.).

Color: off white granular solid

Purity=97% (HPLC)

Optical purity (Chiral HPLC)>99.5%.

M.P.(° C.): 186.5–188

Specific Rotation (MeOH, 25° C., 589 nm): +16.429

Composition: C, 41.58; H, 4.56; N, 13.37 [Theoretical: C, 41.50; H, 4.53; N, 13.35]

$^1$H NMR (D$_2$O): δ=1.30–1.60 (m, 1H), 1.80–1.95 (m, 1H), 2.60 (s, 3H), 3.70–3.90 (m,4H),4.10–4.50 (m, 2H), 4.60 (s, 3H), 5.15–5.40 (m, 1H), 6.70–6.80 (m, 2H), 7.00–7.10 (m, 2H), 8.00 (s, 1H), 8.10 (s, 1H).

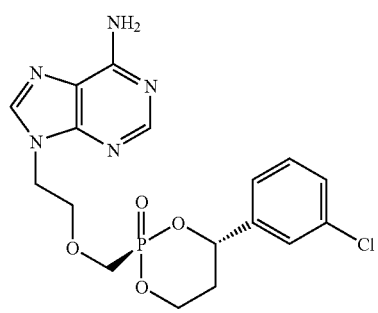

| Compound # | V | Melting Point (° C.) | TLC data | Elemental Analysis | Coupling Method | cis:trans ration[e] |
|---|---|---|---|---|---|---|
| 1 | phenyl | | Rf = 0.55; MeOH:CH₂Cl₂ (4:1) | Calcd: % C 50.68; % H 5.38; % N 17.38. Found: % C 50.52; % H 5.22; % N 17.19. Mol Formula: C17H20N5O4P + 0.75H2O. | a, b | 0.8:1.0 |
| 2 | 4-pyridyl | | Rf = 0.21; CH₂Cl₂/MeOH/NH4OH (90:9:1) | Calcd: % C 49.23; % H 4.91; % N 21.53. Found: % C 49.01; % H 5.01; % N 19.37. Mol formula: C16H19N6O4P. | a, b | 2.0:1.0 |
| 3 | 3,5-dichlorophenyl | | Rf = 0.40; CH₂Cl₂/MeOH (9:1) | Calcd: % C 43.42; % H 4.14; % N 14.89. Found: % C 43.53; % H 3.90; % N 14.62. Mol Formula C17H18Cl2N5O4P + 0.66H2O | a | 2.0:1.0 |
| 4 | 3-chlorophenyl | | Rf = 0.39; CH₂Cl₂/MeOH (9:1) | Calcd: % C 48.18; % H 4.52; % N 16.53; % Cl 8.37. Found: % C 48.23; % H 4.52; % N 16.62; % Cl 8.54. Mol Formula: C17H19ClN5O4P | b, c | 1.0:0 |
| 5 | 4-bromo-3-fluorophenyl | | Rf = 0.38; CH₂Cl₂/MeOH (9:1) | Calcd: % C 40.49; % H 4.00; % N 13.89. Found: % C 40.60; % H 3.89; % N 13.30. Mol Formula: C17H18BrFN5O4P + H2O | a | 2.0:1.0 |
| 6 | 2-bromophenyl | | Rf = 0.37; CH₂Cl₂/MeOH (9:1) | Calcd: % C 41.84; % H 4.38; % N 14.35. Found: % C 41.94; % H 4.09; % N 13.75. Mol Formula: C17H19BrN5O4P + 1.1H2O | a | 1.0:0 |
| 7 | 3-bromophenyl | | Rf = 0.39; CH₂Cl₂/MeOH (9:1) | Calcd: % C 42.15; % H 4.33; % N 14.46. Found: % C 42.23; % H 4.03; % N 14.11. Mol Formula: C17H19BrN5O4P + .9H2O | a, c | 1.5:1.0 |

-continued

| Compound # | V | Melting Point (° C.) | TLC data | Elemental Analysis | Coupling Method | cis:trans ration[e] |
|---|---|---|---|---|---|---|
| 8 | 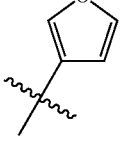 | 174–177 | Rf = 0.30; CH$_2$Cl$_2$/MeOH (9:1) | Calcd: % C 47.50; % H 4.78; % N 18.46. Found: % C 47.25; % H 4.51; % N 18.20. Mol Formula: C15H18N5O4P | a | 1.0:2.0 |
| 9 | 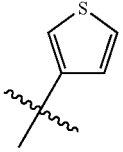 | 152–155 | Rf = 0.31; CH$_2$Cl$_2$/MeOH (9:1) | Calcd: % C 44.38; % H 5.50; % N 16.33. Found: % C 44.47; % H 5.27; % N 16.22. Mol Formula: C15H18N5O4PS + 0.3 TEA-HCl + 1H2O | a | 1.2:1.0 |
| 10 | 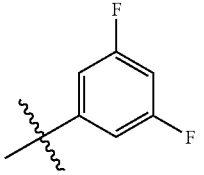 | | Rf = 0.34; CH$_2$Cl$_2$:MeOH (10:1) | Calcd: % C 45.50; % H 4.13; % N 15.25. Found: % C 45.67; % H 3.97; % N 15.07. Mol Formula: C17H18F2N5O4P + 0.4CH$_2$Cl$_2$ | a | 1.4:1.0 |
| 11 | 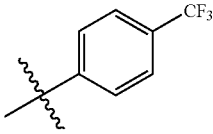 | | Rf = 0.66 CH$_2$Cl$_2$/MeOH (10:1) | Calcd: % C 44.46; % H 4.03; % N 14.01. Found: % C 44.22; % H 4.12; % N 13.91. Mol Formula: C18H19F3N5O4P + 0.5CH$_2$Cl$_2$ | a | 2.0:1.0 |
| 12 | 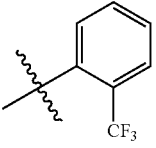 | | Rf = 0.53; CH$_2$Cl$_2$/MeOH (15:1) | Calcd: % C 43.95; % H 4.01; % N 13.78. Found: % C 43.91; % H 4.25; % N 13.89. Mol Formula: C18H19F3N5O4P + 0.6CH$_2$Cl$_2$ | a | 1.4:1.0 |
| 13 | 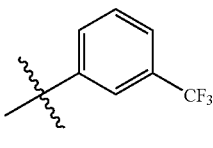 | | Rf = 0.15; CH$_2$Cl$_2$/MeOH (15:1) | HPLC: RT = 13.91 and 14.32 min, eluted with (MeOH/0.1% TFA in H2O (40:60)), 270 nm, flow rate = 0.750 ml/min, 250 × 4.6 mm ODS-AQ column | a | 2.0:1.0 |
| 14 | 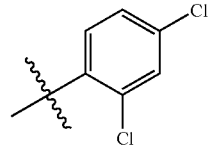 | | Rf = 0.42; CH$_2$Cl$_2$/MeOH (15:1) | Calcd: % C 42.46; % H 3.85; % N 14.23. Found: % C 42.54; % H 4.07; % N 13.93. Mol Formula: C17H18Cl2N5O4P + 0.4CH$_2$Cl$_2$ | a | 1.0:1.0 |
| 15 | 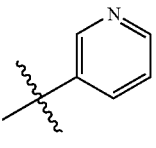 | 117–119 | Rf = 0.35; MeOH/EtOAc (1:1) | | b | 1.0:1.2 |
| 16 | 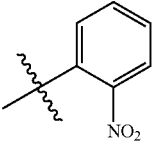 | | Rf = 0.48; CH$_2$Cl$_2$/MeOH (9:1) | Calcd: % C 43.32; % H 4.58; % N 17.52. Found: % C 43.64; % H 4.45; % N 17.25. Mol Formula: C17H19N6O6P + 0.3CH$_2$Cl$_2$ + 1.1H2O | b | 1.0:1.8 |

-continued

| Compound # | V | Melting Point (° C.) | TLC data | Elemental Analysis | Coupling Method | cis:trans ration[e] |
|---|---|---|---|---|---|---|
| 17 | 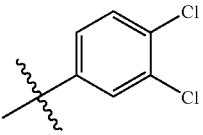 |  | Rf = 0.28 (CH$_2$Cl$_2$/MeOH (9:1)) | Calcd: % C 43.47; % H 3.90; % N 14.74. Found: % C 43.39; % H 3.59; % N 14.82. Mol Formula: C17H18Cl2N5O4P + 0.2CH$_2$Cl$_2$ | b | 1.7:1.0 |
| 18 | 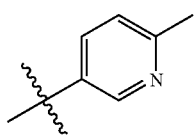 | 84–86 | Rf = 0.3; CH$_2$Cl$_2$/MeOH (9:1) |  | b | 1.0:1.2 |
| 19 | 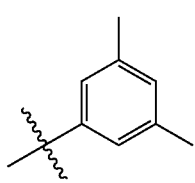 | 155–165 | Rf = 0.14 CH$_2$Cl$_2$/MeOH (25:1) |  | b | 1.5:1.0 |
| 20 | 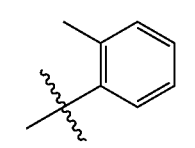 |  | Rf = 0.51; CH$_2$Cl$_2$/MeOH (20:1)) | Calcd: % C 50.53; % H 5.25; % N 16.01. Found: % C 50.77; % H 5.09; % N 16.08. Mol Formula: C18H22N5O4P4 + 0.4CH$_2$Cl$_2$ | b | 1.4:1.0 |
| 21 | 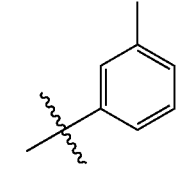 |  | Rf = 0.49 (CH$_2$Cl$_2$/MeOH (14:1)) |  | b | 1.4:1.0 |
| 22 | 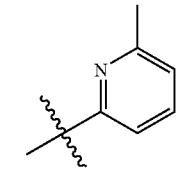 | 80–82 | Rf = .40; CH$_2$Cl$_2$/MeOH (9:1) |  | b | 1.0:1.0 |
| 23 | 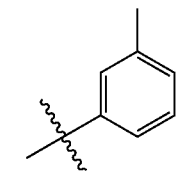 |  | Rf = 0.47 CH$_2$Cl$_2$/MeOH (14:1) | Calcd: % C 51.42; % H 5.73; % N 16.66. Found: % C 51.74; % H 5.75; % N 16.31. Mol Formula: C18H22N5O4P + 0.95H2O | b | 1.0:2.0 |
| 24 | 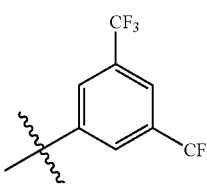 |  | Rf = 0.58; CH$_2$Cl$_2$/MeOH (9:1) | Calcd: % C 42.08; % H 3.40; % N 12.71. Found: % C 41.97; % H 3.58; % N 12.34. Mol Formula: C19H18F6N5O4P + 0.3CH$_2$Cl$_2$ | b | 1.0:1.0 |
| 25 | 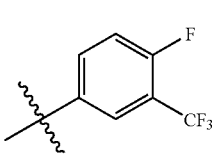 | 105–106 | Rf = 0.56; CH$_2$Cl$_2$/MeOH (9:1) | Calcd: % C 45.48; % H 3.82; % N 14.73. Found: % C 45.81; % H 3.56; % N 14.71. Mol Formula: C18H18F4O4P. | b | 1.0:1.0 |

-continued

| Compound # | V | Melting Point (° C.) | TLC data | Elemental Analysis | Coupling Method | cis:trans ration[e] |
|---|---|---|---|---|---|---|
| 26 | 4-Br, 2-F phenyl | 171–172 | Rf = 0.59 (CH$_2$Cl$_2$/MeOH (9:1)) | Calcd: % C 41.08; % H 3.89; % N 14.09. Found: % C 40.88; % H 3.92; % N 13.93. Mol formula: C17H18BrFN5O4P + 0.6H2O | b | 1.5:1.0 |
| 27 | 4-OMe, 2-Br phenyl | 104–105 | Rf = 0.54; CH$_2$Cl$_2$/MeOH (9:1) | Calcd: % C 43.39; % H 4.25; % N 14.06. Found: % C 43.15; % H 4.35; % N 13.76. Mol Formula: C18H21BrN5O5P | b | 1.0:1.2 |
| 28 | 4-OMe, 3-Br phenyl | 131–132 | Rf = 0.45; CH$_2$Cl$_2$/MeOH (9:1) |  | b |  |
| 29 | 3,5-diBr phenyl | 110–111 | Rf = 0.41; CH$_2$Cl$_2$/MeOH (9:1) | Calcd: % C 37.32; % H 3.32; % N 12.80. Found: % C 37.43; % H 3.21; % N 12.42. Mol Formula: C17H18Br2N5O4P | b | 1.5:1.0 |
| 30 | 4-F, 3-Cl phenyl | 190–192 | Rf = 0.45; CH$_2$Cl$_2$/MeOH (9:1) | Calcd: % C 46.22; % H 4.11; % N 15.85. Found: % C 46.57; % H 4.01; % N 15.46. Mol Formula: C17H18ClFN5O4P | b | 1.0:1.0 |
| 31 | 4-F, 2-Cl phenyl | 208–210 | Rf = 0.62; CH$_2$Cl$_2$/MeOH (9:1) | Calcd: % C 46.22; % H 4.11; % N 15.85. Found: % C 45.94; % H 4.10; % N 15.48. Mol Formula: C17H18ClFN5O4P | b |  |
| 32 | 5-Br pyridyl | 115–118 | Rf = 0.4; CH$_2$Cl$_2$/MeOH (9:1) |  | b | 1.1:1.0 |
| 33 | 4-OMe, 3-F phenyl |  | Rf = 0.48 (CH$_2$Cl$_2$/MeOH (9:1)) | Calcd: % C 47.49; % H 4.70; % N 15.13. Found: % C 47.71; % H 5.05; % N 14.84. Mol Formula: C18H21FN5O5P + 0.3CH2Cl2 | b | 1.0:1.2 |
| 34 | 3-OMe, 4-F phenyl | 90–91 | Rf = 0.61; CH$_2$Cl$_2$/MeOH (9:1) | Calcd: % C 48.83; % H 4.92; % N 15.82. Found: % C 49.15; % H 4.85; % N 14.73. Mol Formula: C18H21FN5O5P + 0.5EtOAc + 0.2H2O | b |  |

-continued

| Compound # | V | Melting Point (° C.) | TLC data | Elemental Analysis | Coupling Method | cis:trans ration[e] |
|---|---|---|---|---|---|---|
| 35 | (5-Br, 2-F phenyl) | 113–115 | Rf = 0.47; CH₂Cl₂/MeOH (9:1) | Calcd: % C 42.54; % H 3.97; % N 13.78. Found: % C 42.41; % H 3.59; % N 15.82. Mol Formula: C17H18BrFN5O4P + 0.25EtOAc | b | |
| 36 | (6-OMe pyridin-3-yl) | 130–132 | Rf = 0.25; CH₂Cl₂/MeOH (9:1) | Calcd: % C 47.05; % H 5.53; % N 18.60. Found: % C 47.23; % H 5.48; % N 18.31. Mol Formula: C17H21N6O5P + 0.5H2O + 0.7 CH3OH | b | 1.0:1.7 |
| 37 | (6-Cl pyridin-3-yl) | 140–142 | Rf = 0.25; CH₂Cl₂/MeOH (9:1) | Calcd: % C 42.54; % H 4.68; % N 18.80. Found: % C 42.64; % H 4.28; % N 18.26. Mol Formula: C16H18N6O4PCl + 1.5H2O | b | 1.0:1.0 |
| 38 | (3,4-dimethylphenyl) | 172–174 | Rf = 0.41; CH₂Cl₂/MeOH (9:1) | Calcd: % C 53.75; % H 5.89; % N 16.49. Found: % C 53.43; % H 5.88; % N 16.91. Mol Formula: C19H24N5O4P + 0.4H2O | b | 2.0:1.0 |
| 39 | (3-F phenyl) | 168–170 | Rf = 0.44; CH₂Cl₂/MeOH (9:1) | Calcd: % C 50.13; % H 4.70; % N 17.19. Found: % C 49.76; % H 4.51; % N 16.82. Mol Formula: C17H19FN5O4P | b | 1.6:1.0 |
| 40 | (2,3-diCl phenyl) | | Rf = 0.63; CH₂Cl₂/MeOH (9:1) | Calcd: % C 43.37; % H 4.15%; % N 14.87. Found % C 43.06; % H 4.05; % N 14.62. Mol Formula C17H18Cl2N5O4P + 0.7H2O | b | |
| 41 | (2-OMe, 5-Br phenyl) | 110–112 | Rf = 0.52; CH₂Cl₂/MeOH (9:1) | Calcd: % C 43.39; % H 4.25; % N 14.06. Found: % C 43.55; % H 4.25; % N 13.76. Mol Formula: C18H21BrN5O5P | b | |
| 42 | (3-OEt phenyl) | | Rf = 0.62; CH₂Cl₂/MeOH (9:1) | Calcd: % C 51.58; % H 5.70; % N 15.83. Found: % C 51.31; % H 5.60; % N 15.69. Mol Formula: C19H24N5O5P + 0.5H2O | b | 1.3:1.0 |

| Compound # | V | Melting Point (° C.) | TLC data | Elemental Analysis | Coupling Method | cis:trans ration[e] |
|---|---|---|---|---|---|---|
| 43 | 2,6-difluorophenyl | | Rf = 0.48; CH₂Cl₂/MeOH (9:1) | Calcd: % C 48.73; % H 4.58; % N 15.61. Found: % C 48.72; % H 4.67; % N 15.79. Mol Formula: C17H18F2N5O4P + 0.4C3H6O | b | |
| 44 | 2,4-difluorophenyl | | Rf = 0.48; CH₂Cl₂/MeOH (9:1) | Calcd: % C 48.56; % H 4.51; % N 15.82. Found: % C 48.67; % H 4.16; % N 15.76. Mol Formula: C17H18F2N5O4P + 0.3C3H6O | b | |
| 45 | 2,3-difluorophenyl | 208–210 | Rf = 0.53; CH₂Cl₂/MeOH (9:1) | Calcd: % C 48.01; % H 4.27; % N 16.47. Found: % C 48.15; % H 4.04; % N 16.07. Mol Formula: C17H18F2N5O4P | b | |
| 46 | 3,4-difluorophenyl | 168–170 | Rf = 0.42; CH₂Cl₂/MeOH (9:1) | Calcd: % C 48.01; % H 4.27; % N 16.47. Found: % C 47.68; % H 4.18; % N 16.08. Mol Formula: C17H18F2N5O4P | b | 1.3:1.0 |
| 47 | 2,5-difluorophenyl | 109–110 | Rf = 0.53; CH₂Cl₂/MeOH (9:1) | Calcd: % C 47.60; % H 4.32; % N 16.33. Found: % C 47.68; % H 4.32; % N 15.93. Mol Formula: C17H18F2N5O4P + 0.2H2O | b | |
| 48 | 2-fluorophenyl | 189–190 | Rf = 0.46; CH₂Cl₂/MeOH (9:1) | Calcd: % C 50.13; % H 4.70; % N 17.19. Found: % C 50.46; % H 4.69; % N 17.08. Mol Formula: C17H19FN5O4P | b | |
| 49 | 2-fluoro-4-chlorophenyl | 183–185 | Rf = 0.51; CH₂Cl₂/MeOH (9:1) | Calcd: % C 46.22; % H 4.11; % N 15.85. Found: % C 46.11; % H 4.05; % N 15.57. Mol Formula: C17H18ClFN5O4P | b | |
| 50 | 4-bromo-2-ethoxyphenyl | 155–158 | Rf = 0.36; CH₂Cl₂/MeOH (9:1) | Calcd: % C 44.55; % H 4.53; % N 13.67. Found: % C 44.85; % H 4.57; % N 13.55. Mol Formula: C19H23BrN5O5P | b | |
| 51 | 2,6-dichlorophenyl | 195–197 | Rf = 0.35; CH₂Cl₂/MeOH (9:1) | Calcd: % C 42.96; % H 3.88; % N 14.48. Found: % C 42.72; % H 3.77; % N 14.52. Mol Formula: C17H18Cl2N5O4P + 0.3CH2Cl2 | b | 1.0:2.0 |

-continued

| Compound # | V | Melting Point (° C.) | TLC data | Elemental Analysis | Coupling Method | cis:trans ration[e] |
|---|---|---|---|---|---|---|
| 52 | ![F, Cl phenyl] | 184–185 | Rf = 0.41; CH₂Cl₂/MeOH (9:1) | Calcd: % C 46.22; % H 4.11; % N 15.85. Found: % C 46.47; % H 4.11; % N 15.46. Mol Formula: C17H18ClFN5O4P | b | 1.0:2.0 |
| 53 | ![Cl phenyl] | 194–195 | Rf = 0.38; CH₂Cl₂/MeOH (9:1) | | b | |

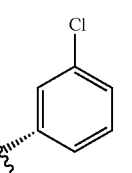

| | | | | | | |
|---|---|---|---|---|---|---|
| 54 | ![Cl phenyl] | | Rf = 0.39; CH₂Cl₂/MeOH (9:1) | Calcd: % C 48.18; % H 4.52; % N 16.53. Found: % C 48.11; % H 4.46; % N 16.26. Mol Formula: C17H19N5O4P | c | all cis, S-isomer |
| 55 | ![Cl phenyl] D-malic acid salt of | | | Appearance: White Crystals | c | all cis, S-isomer |
| 56 | ![Cl phenyl] Methanesulphonic Acid Salt of 54 | 185.5–187 | | Calcd: % C 41.58 % H 4.46; % N 13.47. Found: % C 41.68; % H 4.32; % N 13.33. Mol Formula: C17H19ClN5O4P.CH4 O3 S | c | all cis, S-isomer |

-continued

| Compound # | V | Melting Point (° C.) | TLC data | Elemental Analysis | Coupling Method | cis:trans ration[e] |
|---|---|---|---|---|---|---|
| 57 | 3-Cl-phenyl (attached to adenine-PMEA cyclic phosphonate core) | | Rf = 0.39; CH$_2$Cl$_2$/MeOH (9:1) | Calcd: % C 48.18; % H 4.52; % N 16.53. Found: % C 47.97 % H 4.56; % N 16.28. Mol Formula: C17H19N5O4P | c | all cis, R-isomer |
| 58 | 3-Cl-phenyl · Methanesulphonic Acid | 187–189 | | Calcd: % C 41.58; % H 4.40; % N 13.47. Found: % C 41.58 % H 4.51; % N 13.38. Mol Formula: C17H19ClN5O4P·CH4O3S | c | all cis, R-isomer | a: Thionyl chloride mediated coupling as described in Example 10;
b. DCC mediated coupling as described in Example 11;
c. Oxalyl chloride mediated coupling as described in Example 12;
[e]cis:trans ratio is approximate and based on methine proton NMR integration Preferred compounds of the invention are listed in Table I. Table I contains the structural formulas of the V group, nomenclature, and physical data for the preferred compounds.

Examples of use of the method of the invention include the following. It will be understood that these examples are exemplary and that the method of the invention is not limited solely to these examples.

For the purposes of clarity and brevity, chemical compounds are referred to by compound numbers (from the Table above) in the biological examples below.

BIOLOGICAL EXAMPLES

Example A

In Vitro Activation of PMEA Prodrug Analogues by Rat Liver Microsomes

PMEA prodrug analogues were tested for activation to PMEA in reactions catalyzed by the microsomal fraction of rat liver.

Methods:

Prodrugs (25 and 250 μM) were tested for activation by liver microsomes isolated from rats induced with dexamethasone to enhance CYP3A4 activity (Human Biologics Inc., Phoenix Ariz.). Reactions were conducted in 0.1 M KH$_2$PO$_4$, pH 7.4, in the presence of 2 mM NADPH and liver microsomes (1 mg/mL). Reaction mixtures were incubated for 5 minutes in an Eppendorf Thermomixer 5436 (37° C., speed 6). Reactions were terminated by the addition of 1.5 volumes of methanol. The resulting extracts were clarified by centrifugation at 14,000 rpm in an Eppendorf microfuge (20 minutes). The supernatants (200 μL) were evaporated under vacuum and heat to dryness before resuspending in 80 μL of buffer A (see below) for PMEA analysis. Spiked standards of 9-[2-(phosphonomethoxy)ethyl]adenine, (PMEA, lot 980397, Metabasis Therapeutics) were prepared in the same reaction mixture and processed in an identical fashion. After resuspension, samples were analyzed by reverse phase HPLC (Altima C-18 column) with use of an ion-pairing buffer (Buffer A) consisting of 10 mM ammonium phosphate, 2.5 mM octyltriethylammonium phosphate, pH 5.5. Samples were loaded in Buffer A and eluted with a methanol gradient from 40% to 80% over 20 minutes. Detection was at 265 nm. The retention time for PMEA was approximately 14.7 minutes.

Results:

| Compound | Activation Rate, Dex. Rat Liver Microsomes, 25 µM (nmol/min/mg) | Activation Rate, Dex. Rat Liver Microsomes, 250 µM (nmol/min/mg) |
|---|---|---|
| 3 | 2.2 | 1.9 |
| 4 | 6.2 | 10.9 |
| 5 | 1.3 | 1.5 |
| 8 | 4 | 0.3 |
| 18 | <0.5 | 0.6 |

Conclusion:

The majority of the prodrugs tested activated to form the compound of interest, PMEA. Activation rates ranged from <0.5 to 6.2 mmoles/min/mg microsomal protein at the lower drug concentration tested (25 µM). Compound 4 had the highest rate of conversion to PMEA in this system.

Example B

PMEApp Accumulation in Hepatocytes Following Incubation with PMEA Prodrug Analogues PMEA prodrugs that showed a sufficiently high level of activation in rat liver microsomes (Example A) were evaluated for their ability to generate PMEApp, a known HBV polymerase inhibitor, in freshly isolated rat hepatocytes. PMEA prodrugs were tested.

Methods:

Hepatocytes were prepared from fed Sprague-Dawley rats (250–300 g) according to the procedure of Berry and Friend (Berry, M. N. Friend, D. S., *J. Cell Biol.* 43:506–520 (1969)) as modified by Groen (Groen, A. K. et al., *Eur. J. Biochem* 122:87–93 (1982)). Hepatocytes (60 mg/ml wet weight, >85% trypan blue viability) were incubated in 2 ml of krebs-bicarbonate buffer containing 20 mM glucose, and 1 mg/ml BSA for 4 hours in the presence of 250 µM PMEA prodrugs (from 25 mM stock solutions of prodrugs in methanol). At appropriate time points throughout the incubation (0, 1, 2, 4 hours), 400-µl aliquots of the cell suspension were taken and centrifuged through a silicon/mineral oil layer into 10% perchloric acid to extract intracellular nucleotides. The acidic cell extracts were neutralized with 0.3 volumes of 3M KOH/3M $KH_2CO_3$ before evaluating PMEApp levels by ion exchange HPLC (Hewlett Packard 1050) using a Whatman Partisphere SAX (5 µm, 4.6×125 mm) column. Samples were loaded onto the column in 0.3M-ammonium phosphate buffer pH 3.5 and eluted from the column with a gradient to 0.8 M ammonium phosphate pH 3.5. The retention time of PMEApp was 18.6 minutes.

Results:

Following the incubation of PMEA prodrugs with primary rat hepatocytes, PMEApp formation was observed over the course of 0–4 hours. The AUC (area under the curve) values for PMEApp levels (0–4 h) are shown below. Compound 4, Compound 2, and Compound 1 produced the highest levels of PMEApp.

| Compound | Rat Hepatocytes, PMEApp formation, 250 µM, AUC 0–4 h (nmol/g * h) |
|---|---|
| 1 | 149.1 |
| 2 | 106.8 |
| 3 | 64.4 |
| 4 | 109.3 |
| 7 | 70.3 |

Conclusion:

Compounds of this invention show an ability to generate PMEApp in freshly isolated rat hepatocytes.

Example C

PMEApp Accumulation in Liver Organ Following Oral Administration of PMEA Prodrug Analogues to Normal Fasted Rats PMEA prodrugs were tested in vivo to identify prodrugs with suitable oral bioavailability and favorable intrahepatic activation rates.

Methods:

Following oral administration of 30-mg/kg prodrug (PMEA equivalents) to normal, fasted rats, liver organ samples were freeze-clamped at 8 hr. Liver organ concentrations of PMEApp were determined following perchloric acid extraction, neutralization by reverse phase HPLC (Hewlett Packard 1050) using a Whatman Partisphere SAX (5 µm, 4.6×125 mm) column. Samples were loaded onto the column in 0.3 M ammonium phosphate buffer pH 3.5 and eluted from the column with 0.8 M ammonium phosphate pH 3.5. The retention time of PMEApp was 18.6 minutes.

Results:

| Compound | Rats, PMEApp levels in liver organ @ 8 hr., 30 mg/kg, p.o. (nmol/g) |
|---|---|
| 4 | 6.6 |
| 5 | 2.6 |
| 6 | 7.1 |
| 7 | 2.2 |
| 10 | 2.2 |
| 1 | 0.6 |

Conclusion:

PMEApp was readily detected in liver organ following oral administration of the PMEA prodrugs tested.

Example B

In Vitro Activation of Compound 4 by Human Liver Microsomes; CYP3A4 Selectivity of the Reaction The kinetics of activation of Compound 4 by the microsomal fraction of human liver were determined. P450 isoform specificity of the reaction was determined by evaluating the effects of the known CYP3A4-selective inhibitor, ketoconazole.

Methods:

Human liver microsomes were purchased from In Vitro Technologies (IVT). Lot 1011 was prepared from a pool of 10 male donors with documented CYP3A4 activity (testosterone 6β-hydroxylation rate of 5.7 nmol/mg/min; IVT). Compound 4 (lot 990301) was synthesized at Metabasis Therapeutics and solubilized in methanol. Ketoconazole was purchased from Research Biochemicals International (lot SJG-597A) and solubilized in methanol. Following a 2-minute preincubation at 37° C., reaction mixtures containing 100 mM KH2PO4, 2 mg/mL human liver microsomes, and 0, 30, 60, 100, 200 and 400 µM Compound 4 were started by addition of NADPH to 2 mM. The reaction was carried out for 10 minutes in an Eppendorf Thermomixer 5436 at 37° C., speed 6. Inhibition studies were performed in the same fashion with 100 µM Compound 4 and ketoconazole concentrations of 0, 0.01, 0.1, 1, 10 and 100 µM. Reactions were terminated by the addition of 1.5 volumes of methanol and extracts were pelleted at 14,000 rpm in an Eppendorf microfuge for 20 minutes. The supernatants (200 µl) were evaporated under vacuum and heat to dryness before resuspending in 80 µL buffer A (see below). Spiked standards of 9-[2-(phosophonomethoxy)ethyl]adenine, (PMEA, lot 980397, Metabasis Therapeutics) were prepared in the reaction mixture, and quenched and processed in an identical fashion. The ion-pairing buffer (Buffer A) consisted of 10 mM ammonium phosphate and 2.5 mM octyltriethylammonium phosphate, pH 5.5. After resuspension, samples were analyzed for PMEA by reverse phase HPLC. Samples were loaded onto an Altima C-18 nucleotide column in Buffer A and eluted with methanol at a gradient from 40% to 80% over 20 minutes with detection at 265 nm. The retention time for PMEA using this method was approximately 14.7 minutes.

Results:

Compound 4 was activated to PMEA in human liver microsomes in a time- and protein concentration-dependent manner. A $K_m$ of 11 µM and a $V_{max}$ of 1.6 mmol/min/mg were determined for the activation of Compound 4 in this system. At a concentration of 1 µM, ketoconazole was found to inhibit 97% of Compound 4 conversion to PMEA (FIG. 1).

Conclusion:

The results thus indicate that Compound 4 turnover in human liver microsomes is catalyzed primarily by CYP3A4 and that the prodrug is a good substrate for this isozyme.

Comparative studies were performed with the single enantiomers of Compound 4 (Compound 57 and Compound 54) to select the enantiomer with the most optimal profile in terms of physico-chemical properties, activation in human liver microsomes, and in vivo accumulation of liver PME-App following oral or intravenous administration to rats.

Example C

Solubility of Compound 4 Enantiomers

The solubility of enantiomers Compound 57 and Compound 54 was assessed in water.

Methods:

Five mg of each enantiomer was weighed out in quadruplicate and the appropriate volume of water added to each sample to achieve a final concentration of 50 mg/mL. The samples were vortexed vigorously and sonicated at room temperature for 15 min. After standing at room temperature for 1 hr, the samples were centrifuged on a table-top microfuge (Eppendorf) at top speed for 2 min at room temperature. The supernatants were then passed through a 0.45 µM filter, and the filtrates diluted and analyzed by HPLC against known standards to assess drug concentration. HPLC analysis was conducted on an HP1090 system with use of a Beckman Ultrasphere column (4.6×150 mm, 5 µM) at 40° C. The column was eluted at 1.5 mL/min with a linear gradient from 20 mM potassium phosphate buffer pH 6.2 to 80% acetonitrile over 15 minutes. The column effluent was monitored at 260 nm.

Results:

The R and S enantiomers of Compound 4, i.e., Compound 57 and Compound 54, were roughly of equivalent and high solubility in water.

Solubility in Water of Compound 57 and Compound 54

| Compound | Solubility (water) |
| --- | --- |
| 57 | 14 mg/ml |
| 54 | 16 mg/ml |

Conclusion:

The results indicate that the solubility is not affected by the enantiomeric form.

Example D

Solubility of Compound 4 Enantiomers in Phosphate Buffer

The stability of enantiomers Compound 57 and Compound 54 was assessed in phosphate buffer at pH 3, 7, and 9 (RT).

Methods:

The stability of the enantiomers was determined at room temperature in 100 mM potassium phosphate buffer at pH 3, 7, and 9. Solutions (200 µg/mL) of the enantiomers were prepared at each pH and stability analyzed by monitoring prodrug concentration by HPLC at regular intervals for 75 hours. HPLC conditions were identical to those described in Example E.

Results:

The stability of the enantiomers was identical; they exhibited high stability at acidic (3) and neutral (7) pH. Prodrug decomposition (hydrolysis) occurred only under basic conditions (pH 9).

Stability of Compound 57 and Compound 54 in Buffer (pH 3, 7, 9)

| Compound | Buffer (pH 3) Stability (RT) | Buffer (pH 7) Stability (RT) | Buffer (pH 9) Stability (RT) |
| --- | --- | --- | --- |
| 57 | T90% > 75 h | T90% > 75 h | T½ = 11.6 h |
| 54 | T90% > 75 h | T90% > 75 h | T½ = 11.6 h |

Conclusion:

The results indicate that the stability is not affected by the enantiomeric form.

Example E

Stability in Rat and Human Plasma

The stability of enantiomers Compound 57 and Compound 54 was assessed in rat and human plasma at 37° C.

Methods:

The stability of the enantiomers was determined in duplicate samples in heparinized rat and human plasma at 37° C. At t=0, the blank plasma samples (~1 mL) were spiked separately with each enantiomer to a final drug concentration of 50 µg/mL and incubated at 37° C. At preselected times, an aliquot of 100 µL of the plasma samples was mixed with the quench cocktail (150 µL) consisting of 98%v/v acetonitrile and 2% v/v acetic acid. Extracts were vortexed and centrifuged to remove the precipitate. The supernatant was analyzed for drug by the HPLC method described above in Example E.

Results:

The stability of the Compound 4 enantiomers in heparinized rat or human plasma at 37° C. was found to be similar.

Stability of Compound 57 and Compound 54 in Rat and Human Plasma

| Compound | Human Plasma Stability (37° C.) | Rat Plasma Stability (37° C.) |
|---|---|---|
| 57 | $T_{1/2}$ = 8.2 h | $T_{1/2}$ = 4.9 h |
| 54 | $T_{1/2}$ = 8.6 h | $T_{1/2}$ = 3.9 h |

Conclusion:

The stability of these compounds compares favorably to that of bis POM PMEA, known to decompose rapidly in human serum with a half-life of <5 minutes (*J. Med. Chem.* 39:4958–4965 (1996)).

Example F

In Vitro Activation in Human Liver Microsomes

The two enantiomers were compared for activation in human liver microsomes.

Methods:

Human liver microsomes were purchased from In Vitro Technologies (IVT1032). The comparative study was performed at 2 mg/mL human liver microsomes, 100 mM $KH_2PO_4$, 10 mM glutathione, 25 µM or 250 µM compound, and 2 mM NADPH for 0–7.5 minutes in an Eppendorf Thermomixer 5436 at 37° C., speed 6. The reactions were initiated by addition of NADPH following a 2-minute pre-incubation. Reactions were quenched with 60% methanol at 0, 2.5, 5, and 7.5 minutes. L-Glutamyl-L-(S-(3-oxo-3-(3-chlorophenyl)propyl)cysteinylglycine, a glutathione adduct of the by-product of prodrug activation, 3-Cl-phenyl vinyl ketone, was quantified following extraction of the reaction with 1.5 volumes of methanol. The extracted samples were centrifuged at 14,000 rpm in an Eppendorf microfuge and the supernatant analyzed by HPLC for L-Glutamyl-L-(S-(3-oxo-3-(3-chlorophenyl)propyl)cysteinylglycine content. Spiked L-Glutamyl-L-(S-(3-oxo-3-(3-chlorophenyl)propyl)cysteinylglycine (lot 20000127) standards (1–30 µM) were prepared in 2 mg/ml microsomes under reaction conditions and then quenched and processed in an identical fashion to unknown samples. For HPLC analysis, the loading mobile phase buffer (Buffer A) consisted of a 9:1 ratio (v/v) of 20 mM potassium phosphate, pH 6.2 and acetonitrile. Extract (100 uL) was injected onto a Beckman Ultrasphere ODS column (4.6×250 mM, part#235329). The column was eluted with a gradient to 60% acetonitrile. The elution of L-Glutamyl-L-(S-(3-oxo-3-(3-chlorophenyl)propyl)cysteinylglycine (retention time 10.4 minutes) was monitored at 245 nm.

Results:

Activation of Compound 4 Enantiomers in Human Liver Microsomes

| Compound | Activation (25 µM) (pmol/mg/min) | Activation (250 µM) (pmol/mg/min) |
|---|---|---|
| 4 (racemate) | 38 | 283 |
| 57 | 16 | 159 |
| 54 | 62 | 383 |

Conclusion:

Formation of product, L-Glutamyl-L-(S-(3-oxo-3-(3-chlorophenyl)propyl) cysteinylglycine was linear with respect to protein concentration and time for these measurements. The S-enantiomer, Compound 54 was the most readily activated enantiomer in vitro in human liver microsomes at both low (25 µM) and high (250 µM) prodrug concentrations.

Example G

Assessment of PMEApp Accumulation in Rat Liver Organ with Compound 57 and Compound 54

A comparison of hepatic PMEApp accumulation following i.v. and oral administration of Compound 54 (S enantiomer of Compound 4) and Compound 57 (R enantiomer of Compound 4) was performed to identify the enantiomer with the highest oral bioavailability.

Methods:

Following i.v. or oral administration of 30 mg/kg (in terms of PMEA equivalents) of either enantiomer to normal, fasted rats, liver organ samples were freeze-clamped at 20 min, 1, 3, 5, 8, 12, and 24 hr post dose. Following perchloric acid extraction and neutralization, liver organ samples were analyzed by anion exchange HPLC (Hewlett Packard 1050) using a Whatman Partisphere SAX column (5 µm, 4.6×125 mm). The column was developed with a gradient from 0.3M ammonium phosphate buffer pH 3.5 to 0.8M ammonium phosphate pH 3.5. Detection was at 254 nm. The retention time of PMEApp was 18.6 minutes.

Results:

Conversion to PMEApp in Rat Liver Organ (30 mg/kg PMEA Equivalents)

| Compound | Route | AUC PMEApp 0–24 h | OBAV |
|---|---|---|---|
| 57 | i.v. | 435.1 nmol * h/g | |
| 57 | p.o. | 93.0 nmol * h/g | 21% |
| 54 | i.v. | 684.6 nmol * h/g | |
| 54 | p.o. | 213.2 nmol * h/g | 31% |

Figure 2A:
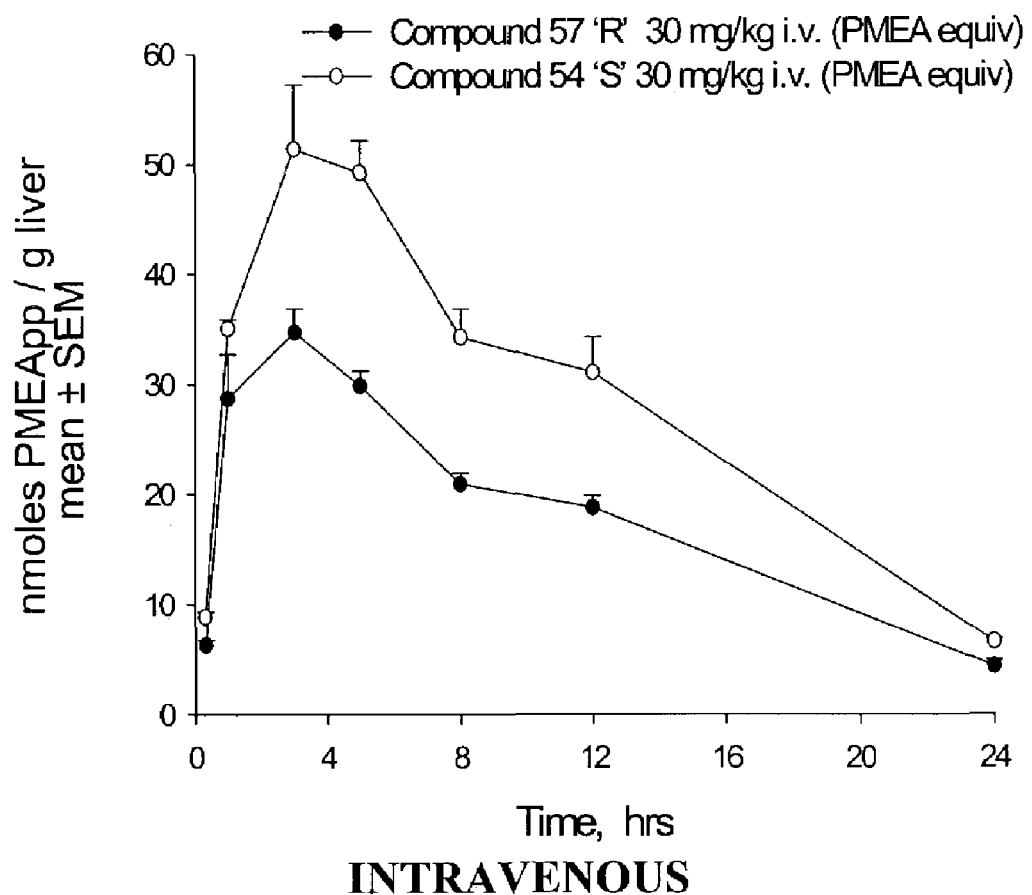
FIG. 2a. Depicts the Liver PMEApp levels following i.v. administration.
Figure 2B:
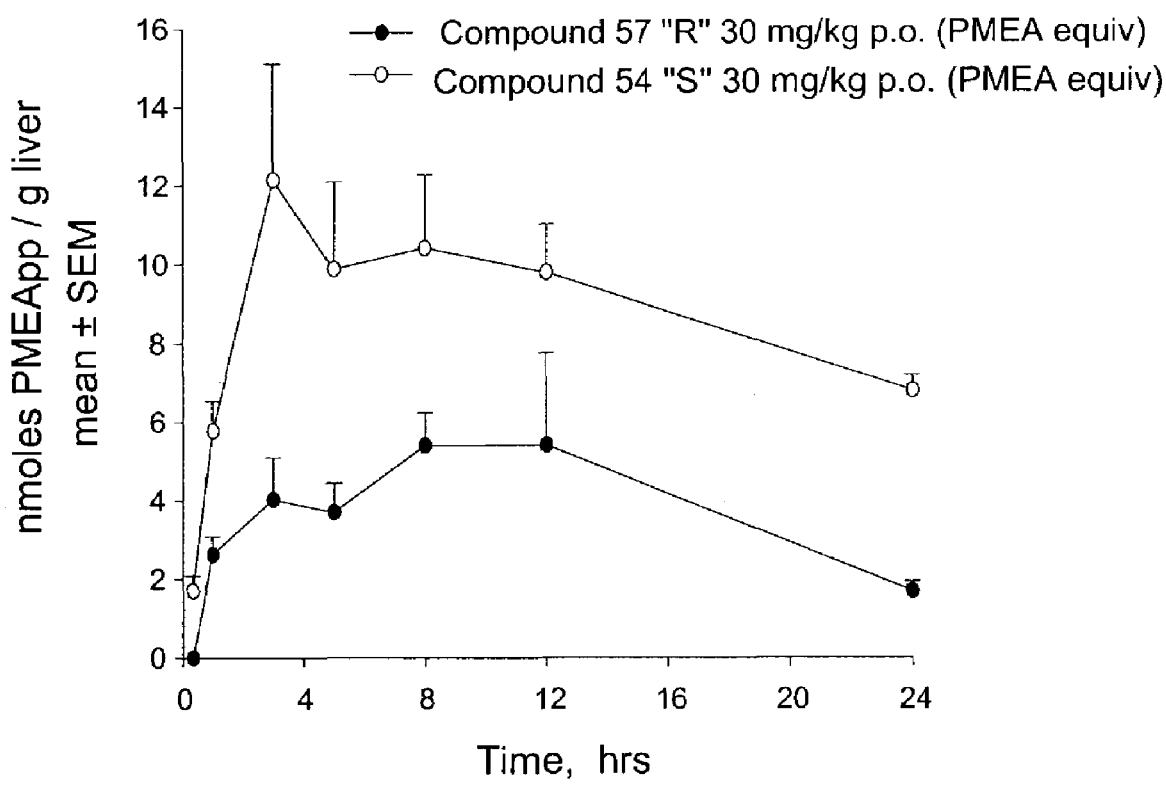
FIG. 2b. Depicts the Liver PMEApp levels following oral administration.

Conclusion:

Compound 54 demonstrated 1.57-fold higher and 2.29-fold higher PMEApp accumulation (AUC) in liver organ following intravenous administration and oral administration, respectively, compared to Compound 57 (FIGS. 2A and 2B). Compound 54 had higher oral bioavailability than Compound 57 based on the AUC of liver organ PMEApp.

Example H

Selection of Compound 54 Salt Form

Selection of an appropriate Compound 54 salt form was required to aid in selective crystallization of the cis-diastereomer following prodrug coupling.

Methods:

Ten Compound 54 salt forms (L-tartartric, succinic, maleic, L-malic, D-malic, citric, hydrochloric, phosphoric, nitric, methane-sulfonic acids) were evaluated to identify the best salt form to selectively crystallize out the cis-diastereomer from cis:trans mixtures following the prodrug coupling procedure. Solubility and stability of the mesylate salt of Compound 54 were analyzed in water.

Results:

The methane-sulfonic acid form, designated as Compound 56 was identified as the best salt form to selectively crystallize the cis-diastereomer from the initial 75 (cis): 25 (trans) mixture. A single crystallization with mesylate salt improved the ratio to 93 (cis):7 (trans) mixture, compared to 82 (cis):18 (trans) for the succinic acid salt or no improvement for the remainder of salt forms. In water, Compound 56 was highly soluble (>300 mg/ml) and dosing solutions (30 and 300 mg/ml) were found to be stable over 5 days at room temperature (<10% decomposition).

Conclusion:

The methanesulfonic acid salt was the best salt tested to selectively crystallize the cis-diastereomer.

Example I

Determination of Compound 56 Kinetic Parameters in Liver Microsomes from Various Species The kinetic parameters of activation of Compound 56, a prodrug of PMEA, were compared in liver microsomes from male and female mouse (CD-1), rat (Sprague-Dawley), dog (beagle), monkey (cynomolgus), woodchuck, and human pools.

Methods:

The P450-catalyzed activation of Compound 56 to PMEA was monitored by a glutathione by-product capture HPLC assay as described in Example H. Kinetic parameters of $K_m$ and $V_{max}$ were calculated using SigmaPlot Enzyme Kinetics Module v.1.1. The intrinsic clearance ($V_{max}/K_m$), a measure of catalytic efficiency, was also evaluated. Protein concentrations were determined by a commercially-available Bradford method.

Results:

Kinetic studies show the activation of Compound 56 in various species, including mouse, rat, dog, monkey, human, and woodchuck. For example, the $(V_{max}/K_m)[\mu L/min/mg]$ values were 74.8+/−7.7 (male) and 77.5+/−13.0 (female) in monkey; 10.8+/−1.2 (male) and 23.2+/−1.0 (female) in human; and 31.5+/−0.8 (male) in woodchuck.

Conclusion:

Kinetic parameters of activation of the prodrug Compound 56 to its parent compound PMEA in microsomal preparations vary by species; it is highest in monkey. High activation of the prodrug by monkey microsomes justifies the use of this species in toxicological studies. Kinetic parameters in woodchuck were similar to human supporting the potential use of woodchuck for preclinical efficacy studies.

Example J

Assessment Of the Oral Bioavailability of Compound 56 in Normal Male Rats

The oral bioavailability (OBAV) of the highly water-soluble mesylate salt of the S enantiomer of the cis form of Compound 4, i.e., Compound 56, was evaluated in the normal male rat.

Methods:

Compound 56 was solubilized in water for intravenous and oral administration. The OBAV was assessed by calculating the ratio of the AUC values of the liver organ concentration-time profile of PMEApp following oral and i.v. administration of 30 mg/kg (in terms of PMEA equivalents) of Compound 56 to groups of four rats. Liver organ samples were taken at 20 min and 1, 3, 5, 8, 12, and 24 hrs following dosing. Liver organ concentrations of PMEApp were determined as indicated in Example I.

Figure 3:
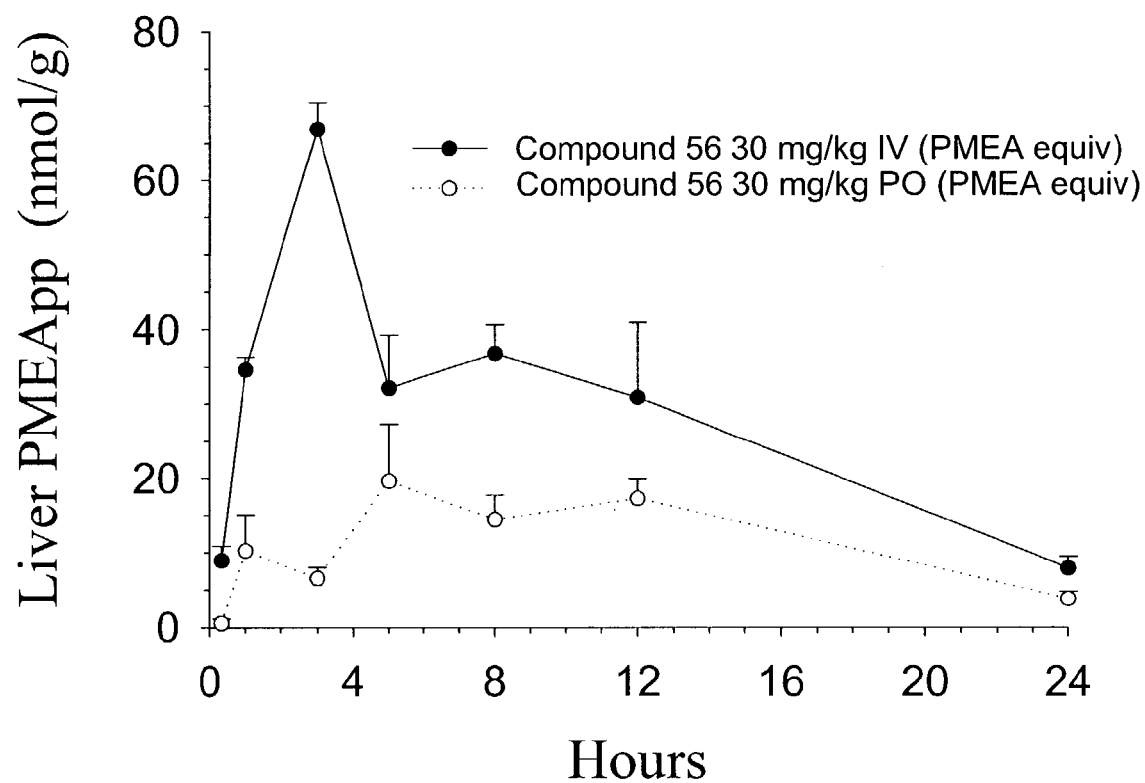
FIG. 3. Depicts the Oral Bioavailability of Compound 56 through the use of a liver concentration-time profile of PMEApp.

Results:

The liver organ concentration-time profile of PMEApp is shown in FIG. 3. The OBAV was estimated to be 42% per the above definition. This value is at minimum equivalent than the OBAV determined for the free base (31%) in Example I.

Conclusion:

Compound 56 showed good bioavailability.

Example K

PMEApp Accumulation in Hepatocytes following Incubation with Compound 56 and PMEA Compound 56 and PMEA, the parent antiviral drug, were evaluated for their ability to generate PMEApp, a known HBV polymerase inhibitor, in freshly isolated rat hepatocytes.

Methods:

Hepatocytes were prepared from fed Sprague-Dawley rats (250–300 g) according to the procedure of Berry and Friend (Berry, M. N. Friend, D. S. *J. Cell Biol.* 43:506–520 (1969)) as modified by Groen (Groen, A. K. et al., *Eur. J. Biochem* 122:87–93 (1982)). Hepatocytes (20 mg/ml wet weight, >85% trypan blue viability) were incubated in 2 ml of krebs-bicarbonate buffer containing 20 mM glucose, and 1 mg/ml BSA for 4 hours in the presence of 25 µM PMEA prodrugs (from 25 mM stock solutions of prodrugs in methanol). At appropriate time points throughout the incubation (0, 1, 2, 4 hours), 1600-µl aliquots of the cell suspension were taken and centrifuged to pellet hepatocytes. Hepatocyte pellets were immediately sonicated in 300 µl of ice-cold acetonitrile followed by the addition of 200 µl of water. Hepatocyte extracts were centrifuged for 20 minutes in an Eppendorf centrifuge at 4° C. and supernatants from the extracts were transferred to a fresh tube. Hepatocyte extract supernatants were evaporated to dryness under vacuum and then resuspended in 200 µl of water. PMEApp concentrations were quantified by LC-MS/MS (negative-ion mode) based on authentic PMEApp standards spiked into hepatocyte extracts. Ten microliter samples were loaded onto a Phenomenex Luna 5 µL C8 column (50×2 mm) in 20 mM N-N-dimethylhexylamine, 10 mM propionic acid and eluted with a gradient of methanol from 20–64% over 5.5 minutes. An API 2000 triple quadrupole mass spectrometer fitted with a pneumatically-assisted electrospray interface was used to quantify the negative ion ($PO_3^-$) using a Multiple Reaction Monitoring (MRM) technique.

Figure 4:
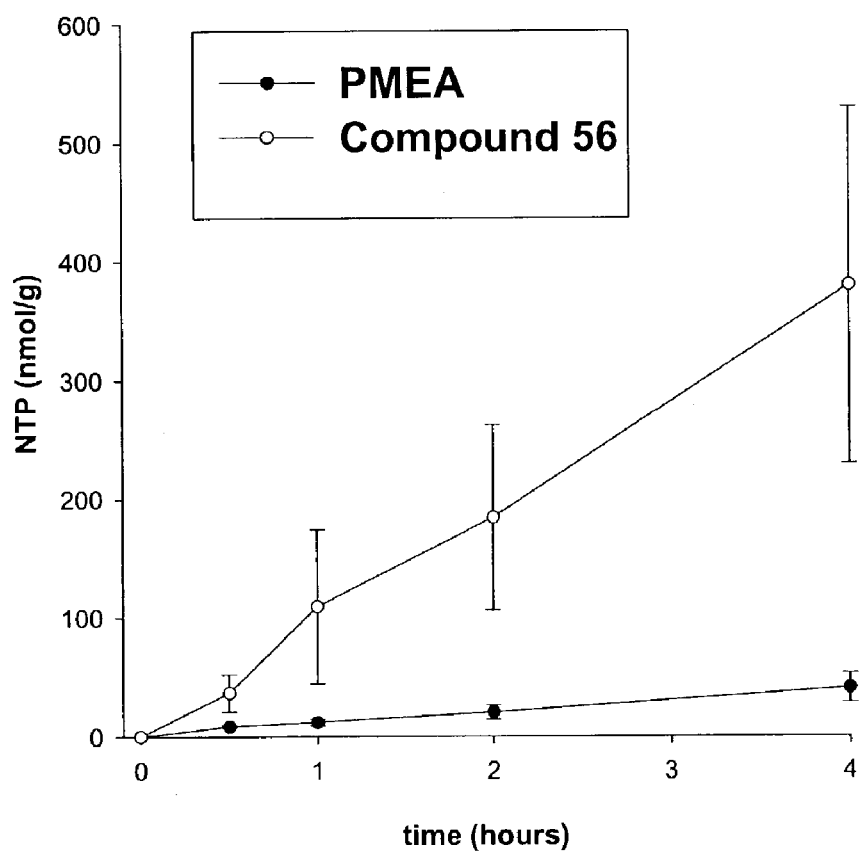
FIG. 4. Depicts the PMEApp accumulation in rat hepatocytes with Compound 56 and PMEA.

Results:

The $AUC_{0-4h}$ (area under the curve) values for PMEApp levels were 756 mmoles*h/g following incubation with Compound 56 compared to 84 mmoles*h/g following incubation with PMEA (FIG. 4).

Conclusion:

These results suggest that Compound 56 generates PMEApp more efficiently than PMEA in isolated rat hepatocytes.

Example L

Tissue Distribution of PMEA Following Oral Administration of Compound 4 and BisPOM PMEA The liver specificity of Compound 4 [adenine-2, 8-$^3$H], was compared relative to bis POM PMEA [adenine-8-$^3$H] in kidney and small intestine, the organs in which PMEA toxicities have been reported.

Methods:

Compound 4 [adenine-2, 8-$^3$H] or bis POM PMEA [adenine-8-$^3$H] was administered at 30 mg/kg PMEA equivalents to fasted rats by oral gavage. Total tritium counts were analyzed in solubilized samples of liver organ, kidney, plasma, urine, red blood cells, small intestine, as well as small intestine contents and feces obtained at various time points over 24 hours. Liver organ specificity was assessed by comparison of the temporal profiles of total tritium in liver organ versus kidney, small intestine, plasma, and red blood cells. Metabolite profiles in perchloric acid extracts of liver organ, kidney, small intestine, feces and urine were analyzed by HPLC.

Figure 5A:
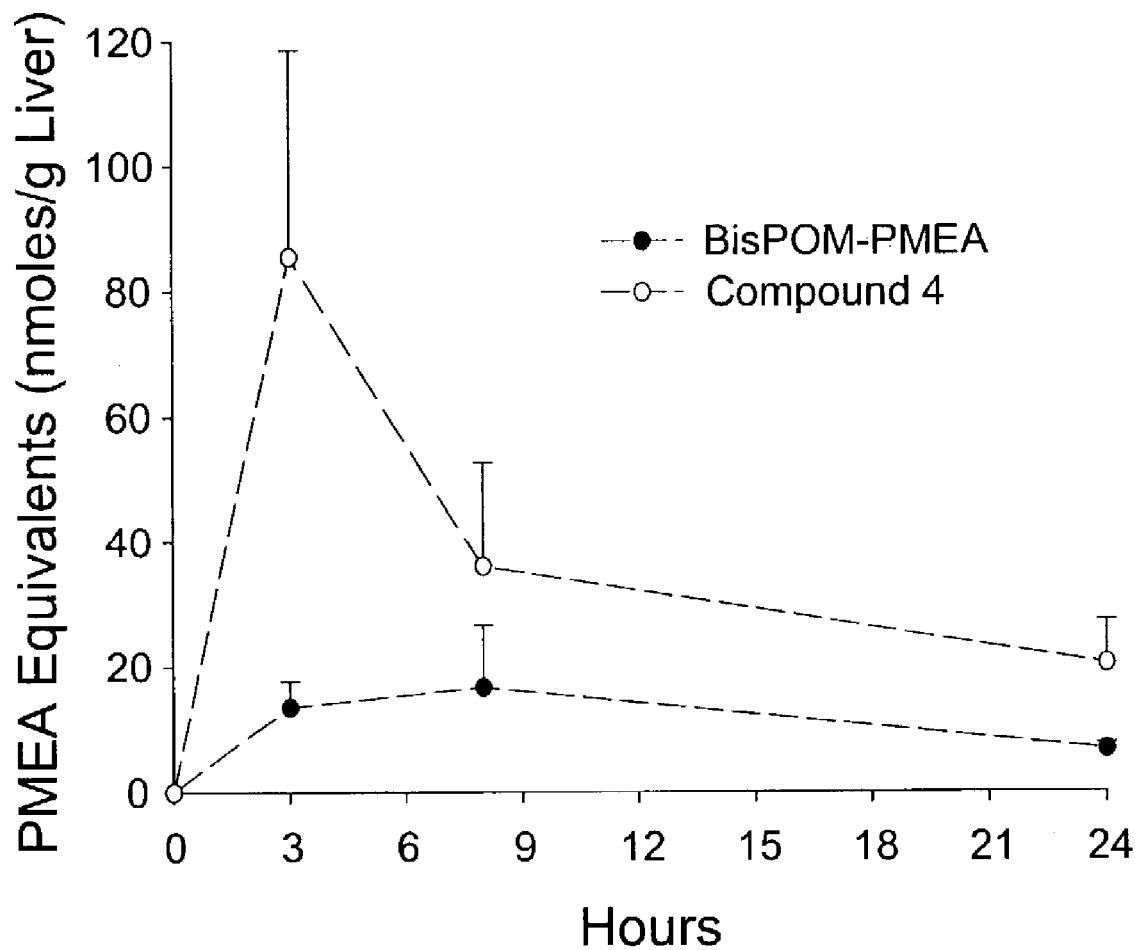
FIG. 5a. Depicts Liver tissue distribution of Compound 4 and bis POM PMEA.
Figure 5B:
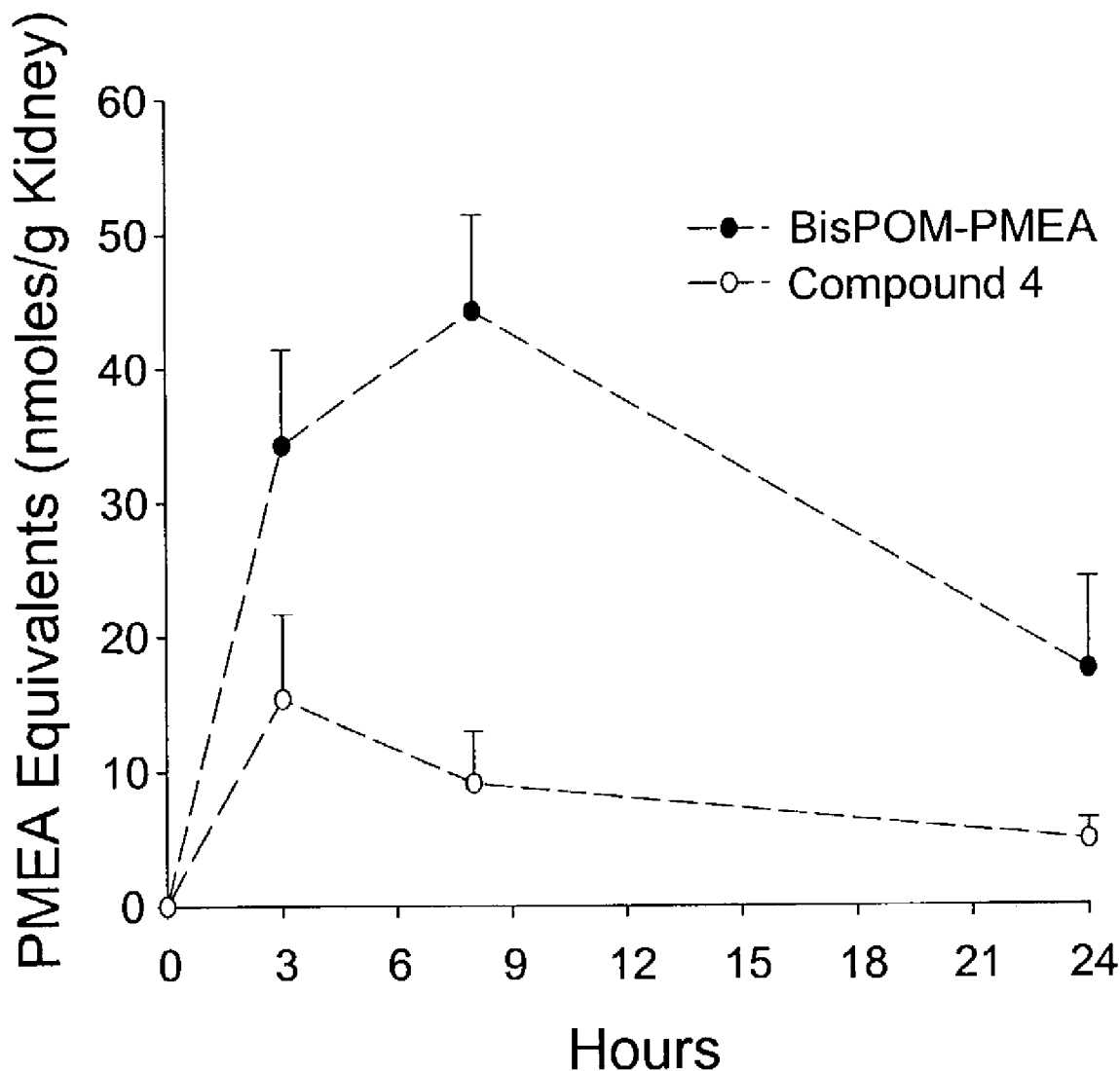
FIG. 5b. Depicts Kidney Tissue distribution of Compound 4 and bis POM PMEA.
Figure 5C:
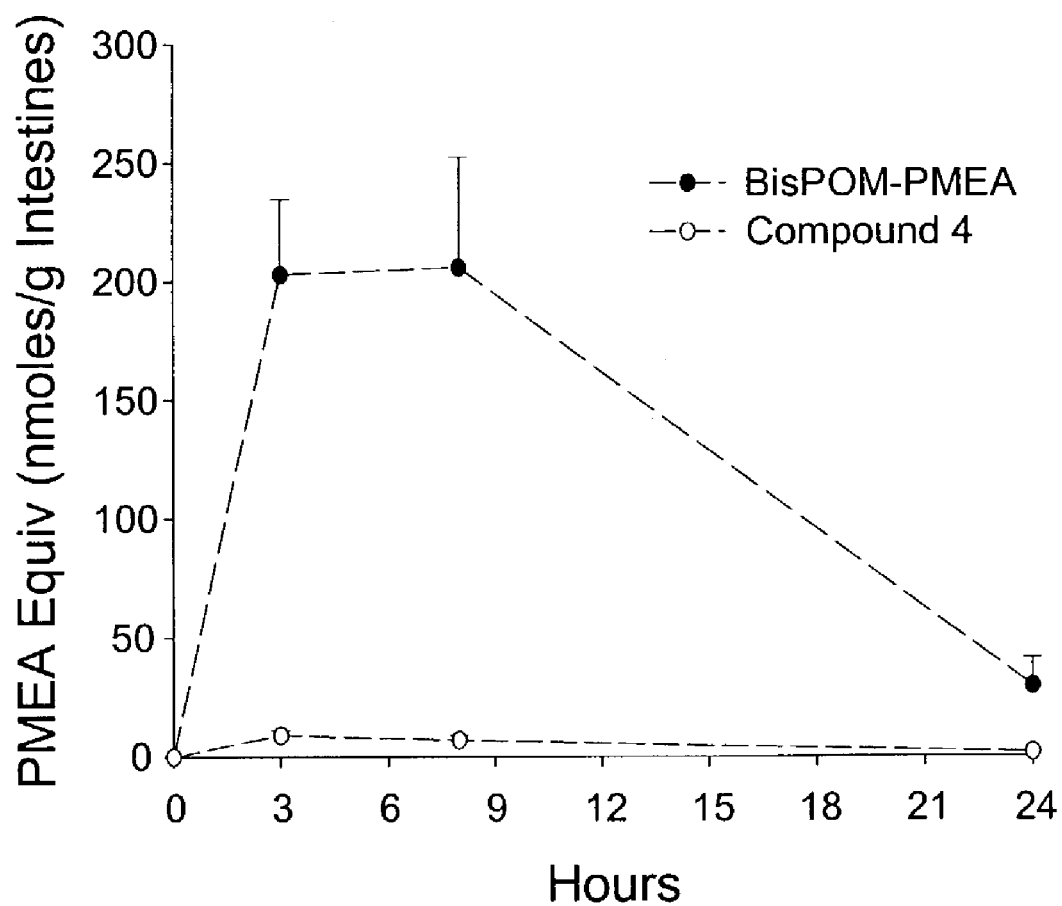
FIG. 5c. Depicts Small Intestine tissue distribution of Compound 4 and bis POM PMEA.

Results:

Compound 4 generated a 3.1-fold higher AUC of PMEA equivalents in liver organ relative to bis POM PMEA while decreasing the exposure of PMEA equivalents in kidney (3.8-fold) and small intestine (25-fold) (FIGS. 5A, 5B and 5C). Compound 4 and bis POM PMEA generated similar ratios of PMEA:PMEA-monphosphate:PMEA-diphosphate in the tissues examined; the intact prodrugs, however, were not detected in these tissues. The majority of the Compound 4 dose (~60%) was found as intact prodrug in feces after 24 hours. Bis POM PMEA, in contrast, was readily metabolized in the intestinal tract; 43% of the dose was excreted in feces in the form of PMEA.

Liver Organ Targeting Index of Compound 4 and bisPOM PMEA

| Compound | Liver organ | Kidney | Small Intestine | Liver organ selectivity index (Liver organ/ Kidney) | Liver organ selectivity index (Liver organ/ Small Intestine) |
|---|---|---|---|---|---|
| bisPOM PMEA | 284 | 742 | 3206 | 0.38 | 0.09 |
| Compound 4 | 884 | 196 | 118 | 4.51 | 7.47 |
| Compound 4/ bisPOM PMEA (fold difference) | 3.11 | 0.26 | 0.04 | 11.8 | 84.38 |

Conclusion:

These results indicate significant improvements in the liver organ targeting indices (see Table above) for Compound 4 compared to bis POM PMEA. Compound 4 is thus likely to have a better safety and efficacy profile than bis POM PMEA.

Example M

Plasma, and Urine Distribution of PMEA Following Oral Administration of Compound 4 and bisPOM PMEA In a parallel study, PMEA levels were quantified in plasma and urine following administration of Compound 4 vs. bis POM PMEA.

Method:

Compound 4 or bis POM PMEA was administered at 30 mg/kg PMEA equivalents to fasted rats by oral gavage. PMEA levels (0–12 h) were quantified in plasma by fluorescence HPLC following chloroacetaldehyde derivatization. PMEA levels in urine were quantified 48 hours after treatment.

Plasma drug levels: PMEA was determined in plasma by a modification of the procedure described in the literature (Shaw J P, Louie M S, Krishnamurthy V V, Arimilli M N, Jones R J, Bidgood A M, Lee W A, & Cundy K C, *Drug Metabolism and Disposition,* 25:362–366 (1997)). Plasma (100 µL) samples were extracted with 2 volumes of 0.1% TFA in acetonitrile. Following centrifugation to remove the precipitate, the supernatant was evaporated to dryness. The dried plasma was reconstituted with 200 µL of the derivatization cocktail consisting of 0.34% chloroacetaldehyde in 100 mM sodium acetate pH 4.5 and incubated at 95° C. for 40 min. The samples were evaporated to dryness and reconstituted with mobile phase for analysis by HPLC. The derivatized PMEA was analyzed by an HPLC system (Hewlett Packard 1090) consisting of a Beckman Ultrasphere ODS 4.6×150 mm (5 µm) column developed with a 20-min gradient of 0–30% acetonitrile in 20 mM potassium phosphate pH 6.2. Fluorescence was monitored at an excitation and emission wavelength of 240 and 420 nm, respectively. The column temperature was 40° C. and the flow rate was 1.5 mL/min. The derivatized PMEA was detected and quantified by comparison to an authentic standard prepared in plasma and eluted at approximately 6 minutes. The limit of quantitation of PMEA, was 0.25 μg/mL.

Urinary excretion studies: The percent excretion of PMEA in urine was assessed by a modification of a previously described procedure (Russell J W, Marrero D, Whiterock V J, & Klunk L J, *J Chromatog,* 572:321–326 (1991)). Aliquots (0.25–0.5 mL) of urine samples and spiked standards were incubated with an equal volume of 17% (v/v) of 50% chloroacetaldehyde in 100 mM sodium acetate pH 4.5 at 50° C. for 4 hrs. Following centrifugation, the supernatant was analyzed by the HPLC method described in the previous section.

Results:

The $AUC_{0-12h}$ of PMEA in plasma following Compound 4 administration was 6-fold lower than following bis POM PMEA administration (3.5 vs 21.3 nmol*h/mL). The $C_{max}$ of PMEA in plasma following Compound 4 administration was 13-fold lower than following bis POM PMEA administration (0.3 vs 4.1 mmoles/mL). Consistent with the reduced kidney levels of PMEA, urinary levels of PMEA following Compound 4 administration were 5-fold lower than following bis POM PMEA administration (4.1% dose vs. 20.6% dose).

Conclusion:

Thus, the reduced systemic PMEA exposure with Compound 4 led to reduced PMEA exposure in kidney, as assessed by urine levels of PMEA, and is therefore expected to lead to reduced PMEA-related toxicity.

Example N

Comparison of Cis (Compound 56) and Trans (9-{2-[2,4-trans-(S)-(+)-4-(3-chlorophenyl)-2-oxo-1, 3,2-dioxaphosphorinan-2-yl]metboxyethyl}adenine) Prodrugs for Activation in Human Liver Microsomes The activation rates of cis (Compound 56, lot #20010093) and trans (9-{2-[2,4-trans-(S)-(+)-4-(3-chlorophenyl)-2-oxo-1,3,2-dioxaphosphorinan-2-yl]methoxyethyl} adenine, (lot 20010195) PMEA prodrugs was compared in order to establish which prodrug diastereomer is activated the most efficiently in human liver microsomes.

Methods:

Human liver microsomes (mixed pool) were purchased from In Vitro Technologies (Lot RQX). The comparative study was performed at 2 mg/mL human liver microsomes, 100 mM $KH_2PO_4$, 10 mM glutathione, 100 μM prodrug, and 2 mM NADPH (used to initiate reaction), for 5 minutes in an Eppendorf Thermomixer 5436 at 37° C., speed 6. Reactions were quenched with 60% methanol. L-Glutamyl-L-(S-(3-oxo-3-(3-chlorophenyl)propyl)cysteinylglycine, a glutathione adduct of the by-product, 3-Cl-phenyl vinyl ketone, was quantified according to the procedures outlined in Example 8 (In Vitro Activation in Human Liver Microsomes).

Results:

The stereochemical purity and activation rates for cis (Compound 56) and trans (9-{2-[2,4-trans-(S)-(+)-4-(3-chlorophenyl)-2-oxo-1,3,2-dioxaphosphorinan-2-yl]methoxyethyl} adenine) prodrug configurations are shown in the table below. The results indicate that the cis (Compound 56) prodrug form is activated in human liver microsomes much more efficiently than the trans form. Activation of the trans form (9-{2-[2,4-trans-(S)-(+)-4-(3-chlorophenyl)-2-oxo-1, 3,2-dioxaphosphorinan-2-yl]methoxyethyl} adenine) was below the measureable detection limit (0.05 mmol/mg/min.).

| Compound | Stereochemical Purity | Activation Rate (nmol/mg/min.) |
|---|---|---|
| cis- | 98.6% cis/1.4% trans | 0.45 ± 0.01 |
| trans- | 1.6% cis/98.4% trans | ≦0.05 |

Conclusion:

Thus, Compound 56 was selected as the superior prodrug diastereomer based on its higher rate of bioactivation in human liver microsomes.

Example O

Non-Toxic Prodrug By-Products in Isolated Rat Hepatocytes

Studies were performed in isolated rat hepatocytes to evaluate the effect of Compound 4 and its metabolites on hepato-toxicity parameters in normal and CYP3A4 induced primary rat hepatocytes relative to acetaminophen, a drug known to cause acute injury as a result of its microsomal metabolism in the liver.

Method:

Freshly isolated hepatocytes were prepared (according to methods described in example 13) from normal rats or rats pre-treated with dexamethasone. Male Sprague Dawley rats were induced with dexamethasone to increase CYP3A4 enzyme content and accordingly maximize Compound 4 metabolism. Normal fed Sprague-Dawley rats weighing 280–310 g were administered dexamethasone intraperitoneally at 50 mg/kg once a day for four days. Dexamethasone was purchased from Sigma (lot#119H1328) and formulated as a suspension in corn oil (Sigma lot#107H1649) at 50 mg/mL. On the fifth day rats were used for hepatocyte isolations. Freshly isolated hepatocytes were treated with Compound 4 (250 μM and 1 mM) or acetaminophen (1–10 mM) in a suspension assay for up to 6 hours. Effects on glutathione levels were assessed by the DTNB (Ellman's reagent) method and viability was determined by the trypan blue exclusion assay and hepatic enzyme leakage assays (LDH, AST). The leakage of lactate dehydrogenase (LDH) and aspartate aminotransferase (AST) into the supernatant was measured using colorimetric assay kits purchased from Sigma (#500 and #505). Both assays were adapted from the protocol insert for a test tube assay to a microtiter plate assay.

Results:

Following treatment with 3 mM or 10 mM acetaminophen, glutathione stores were depleted, viability was reduced to about 5% by trypan blue exclusion criteria, and enzyme leakage was increased by greater than two-fold in hepatocytes isolated from both normal and dexamethasone induced rats. In normal hepatocytes, Compound 4 treatment (1 mM) caused no significant decrease in glutathione levels and no significant changes with respect to viability or hepatic enzyme leakage. In hepatocytes isolated from dexamethasone pre-treated rats, Compound 4 treatment (250 μM, and 1 mM) resulted in significant glutathione decreases (250 μM=50% reduction, 1 mM Compound 4>95% reduction) after a 2-hour incubation, however, no significant changes were observed with respect to viability or hepatic enzyme leakage following glutathione depletion.

Conclusion:

These studies demonstrate that, following extremely high doses of Compound 4, the Compound 4 by-product can reduce intracellular glutathione content in vitro in CYP3A4 induced rat hepatocytes. However, unlike acetaminophen, the Compound 4 by-product/metabolite is not directly cytotoxic to the glutathione-depleted hepatocytes.

Example P

Pharmacokinetics of Compound 4 in Rat

The pharmacokinetic profile of Compound 4, a cyclic prodrug of PMEA, was compared to bis POM PMEA following oral administration to rats.

Method:

Rats (n=4 per time point) were administered 30 mg/kg (in terms of PMEA equivalents) of the prodrugs of Compound 4 and bis POM PMEA by oral gavage. Intact prodrug and the metabolite 9-[2-(phosophonomethoxy)ethyl]adenine (PMEA) and the respective mono-acids were measured in the plasma at 0 (predose), 0.33, 1, 3, 5, 8, and 12 hrs post dose by HPLC using fluorescence detection. The pharmacokinetic parameters were calculated based on noncompartmental analysis of the concentration-time profile.

Results:

Following oral administration of 30 mg/kg of Compound 4 (in terms of PMEA equivalents) to rats, the intact prodrug, Compound 4 and its breakdown products 9-{2-[1-{(3-chlorophenyl)-1-propyl-3-hydroxy}phosphonomethoxy]ethyl} adenine and 9-[2-(phosophonomethoxy)ethyl]adenine (PMEA) were detectable in the plasma. The plasma half-life of Compound 4, 9-{2-[1-{(3-chlorophenyl)-1-propyl-3-hydroxy}phosphonomethoxy] ethyl}adenine, and 9-[2-(phosophonomethoxy)ethyl]adenine was approximately 3.2, 2.1, and 5.5 hrs, respectively. The $C_{max}$ of PMEA was 0.11 μg/mL at a $T_{max}$ of 5 hr. The AUC to 12 hrs was 0.94 mg*hr/mL. Following oral administration of 30 mg/kg of bis POM PMEA (in terms of PMEA equivalents) to rats, only PMEA was detectable in the plasma with a half-life of 6.1 hrs. The $C_{max}$ of PMEA was 1.11 μg/mL at a $T_{max}$ of 20 min. The AUC to 12 hrs was 5.83 mg*hr/mL.

Conclusions:

Compared to bis POM PMEA, the systemic exposure of PMEA as measured by plasma AUC and $C_{max}$ was substantially reduced in the rat when delivered as the Compound 4 prodrug. Intact Compound 4 was observed in plasma whereas bis POM PMEA was not detected, consistent with literature reports (Noble et al., *Drugs* 58:3 (1999)) that claim bis POM PMEA is rapidly hydrolyzed and not detected in vivo. These results indicate that Compound 4 had a preferable pharmacokinetic profile by circulating longer as intact prodrug, while systemic PMEA exposure was minimized, compared to bis POM PMEA.

Example Q

Pharmacokinetics of Compound 4 in Dog

The pharmacokinetics (PK) and oral bioavailability (OBAV) of Compound 4 were determined in the beagle dog and compared to a literature report for bis POM PMEA.

Method:

Following an i.v. bolus and oral administration of 8 and 40 mg/kg (prodrug equivalent dose), respectively, of Compound 4 in PEG-400 to male beagle dogs (n=4), blood samples were collected at the following times: 5, 15, 30, 45 min and 1, 2, 4, 6, 8, 12, and 24 hrs post each dosing occasion. In addition, urine was collected over the following intervals: 0–12, 12–24, 24–48, and 48–72 hrs. Intact Compound 4 and PMEA were measured in the plasma and urine samples using an LC-MS/MS method. PK parameters were determined by non-compartmental analysis. Animals were observed for signs of ill health and mortality.

Results:

Compound 4 was well tolerated by the beagle dogs with no sign of ill health or mortality. Following i.v. administration of Compound 4, the plasma concentrations of intact Compound 4 declined mono-exponentially with a mean terminal elimination half-life $t_{1/2}$ of 0.8 hr. Compound 4 was cleared from the plasma at 1.77 L/hr/kg and was widely distributed with a volume of distribution ($V_{ss}$) of 1.70 L/kg. The mean residence time ($MRT_{iv}$) was estimated to be 1.0 hr. Of the administered i.v. dose, approximately 30% was excreted in the urine as intact Compound 4 whereas only 2% was excreted as PMEA. Following oral administration, Compound 4 was rapidly absorbed with a mean peak plasma concentration ($C_{max}$) of 10.2 μg/mL (~24 μM) achieved after 0.8 hr ($T_{max}$). The terminal $t_{1/2}$ after p.o. dosing was 1.0 hr. Of the administered p.o. dose, 40% was excreted in the urine as intact prodrug and 1.7% was excreted as PMEA. The mean plasma $C_{max}$ of PMEA following oral administration of Compound 4 was 0.24 μg/mL (~0.88 μM) at a $T_{max}$ of 1.4 hr. The half-life of PMEA after oral dosing of the prodrug was 5.4 hr. OBAV of Compound 4 was estimated to be 112% and 82% based on dose normalized oral-to-i.v. AUC ratios and urinary excretion of Compound 4, respectively.

Conclusions:

Compound 4 was rapidly absorbed ($T_{max}$=0.81 hr) and highly orally bioavailable (% F=~100%) in the beagle dog. Compared to literature reports for bis POM PMEA in dog (Cundy et al., *J. Pharm Sci.* 86:12 (1997)), the systemic exposure of PMEA as measured by dose-normalized plasma AUC was reduced by 18.8 fold when delivered as the Compound 4 prodrug (PMEA AUC=10.9 for bis POM PMEA vs. 0.58 for Compound 4). Intact Compound 4 was observed in plasma whereas bis POM PMEA was not reportedly detected. These results indicate that Compound 4 had a preferable pharmacokinetic profile by circulating longer as intact prodrug while minimizing systemic PMEA exposure, compared to bis POM PMEA.

We claim:

1. An isolated compound of Formula III:

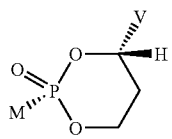

Formula III or a pharmaceutically acceptable salt thereof, wherein:

MPO$_3$H$_2$ is a phosphonic acid selected from the group consisting of 9-(2-phosphonylmethoxyethyl)adenine, (R)-9-(2-phosphonylmethoxypropyl)adenine, 9-(2-phosphonylmethoxyethyloxy)adenine, (S)-9-(3-hydroxy-2-phosphonylmethoxypropyl)adenine, and (S)-9-(3-fluoro-2-phosphonyl-methoxypropyl) adenine;

V is selected from the group consisting of phenyl, 2-pyridyl, 3-pyridyl, 4-pyridyl, 2-furanyl, 3-furanyl, 2-thienyl, and 3-thienyl, all optionally substituted with 1–3 substituents selected from the group consisting of F, Cl, Br, C1–C3 alkyl, CF$_3$ and OR$^6$; and R$^6$ is selected from the group consisting of C1–C3 alkyl, and CF$_3$; wherein said compound has S stereochemistry where V is attached and is isolated apart from the corresponding stereoisomer having R stereochemistry where V is attached, and wherein said compound has greater than 96% diastereomeric purity.

2. The compound of claim 1, wherein MPO$_3$H$_2$ is selected from the group consisting of 9-(2-phosphonylmethoxyethyl)adenine and (R)-9-(2-phosphonylmethoxypropyl)adenine.

3. The compound of claim 1, wherein V is selected from the group consisting of phenyl, 3-pyridyl and 4-pyridyl, all optionally substituted with 1–2 substituents selected from a group consisting of F, Br, Cl, CH$_3$, OCH$_3$, and CF$_3$.

4. The compound of claim 1, wherein V is selected from the group consisting of 4-pyridyl, 2-bromophenyl, and 3-chlorophenyl.

5. The compound of claim 3, wherein said compound is

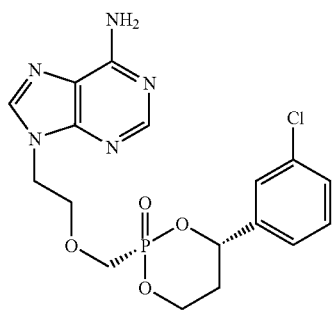

or a pharmaceutically acceptable salt thereof.

6. The compound of claim 5 selected from the group consisting of a pharmaceutically acceptable salt formed with an acid selected from the group consisting of acetic acid, hydrobromic acid, hydrochloric acid, citric acid, maleic acid, methanesulfonic acid, nitric acid, phosphoric acid, succinic acid, sulfuric acid, and tartaric acid.

7. The compound of claim 6 selected from the group consisting of a pharmaceutically acceptable salt formed with an acid selected from the group consisting of methanesulfonic acid and succinic acid.

8. The compound of claim 7, wherein said salt is formed with methanesulfonic acid.

9. A method of treating Hepatitis B in an animal in need thereof, said method comprising administering to the animal the compound of claim 1.

10. The method of claim 9, wherein said compound has Formula IV:

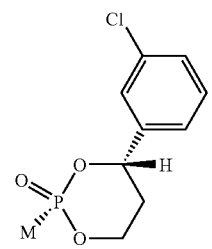

Formula IV or a pharmaceutically acceptable salt thereof.

11. The method of claim 9, wherein MPO$_3$H$_2$ is 9-(2-phosphonylmethoxyethyl)adenine and V is selected from the group consisting of 4-pyridyl, 2-bromophenyl, and 3-chlorophenyl.

12. The method of claim 9, wherein said compound is

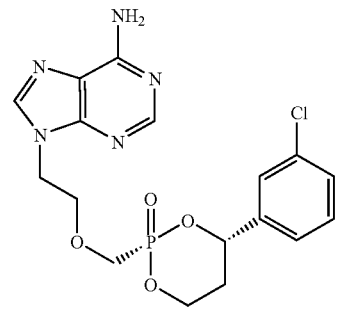

or a pharmaceutically acceptable salt thereof.

13. A method of treating Hepatitis B in an animal in need thereof, said method comprising administering to the animal the compound of claim 1 and a second agent, wherein said second agent is an antiviral agent, and wherein said second agent is effective for treating Hepatitis B.

14. The method of claim 13, wherein said antiviral agent is selected from the group consisting of Vidarabine; Zidovudine; Stavudine; Didanosine; ddA; Zalcitabine; L-ddC; L-FddC; L-d4C; Lamivudine; Ribavirin; FIAU; FIAC; BHCG; BvaraU; E-5-(2-bromovinyl)-2'-deoxyuridine; TFT; Zonavir; CDG; DAPD; FDOC; d4C; d4T; DXG; FEAU; FLG; FLT; Clevudine; Coviracil; Entecavir; Cytallene; Oxetanocin A; Oxetanocin G; NK 84-0218; ddAPR; Cyclobut A; Cyclobut G (Lobucavir); Floxuridine; dFdC; araC; 5-bromodeoxyuridine; IDU; CdA; F-ara-A; ACV; CCV; Penciclovir; Buciclovir; Foscamet; PPA; PMEA; PMEDAP; HPMPC; HPMPA; FPMPA; PMPA; araT; FMdC; AlCAR; AM365; L-dT; L-dC, beta-L-2'-deoxycytosine, a valine prodrug of beta-L-2'-deoxycytosine; ACH 126,443; ddI; ddA; ddC; MCC478; an Interferon; a Pegylated interferon famciclovir; XTL001; an HBV DNA vaccine; Racivir; Robustaflavone; 9-(arabinofuranosyl)-2,6-diaminopurine; 9-(2'-deoxyribofuranosyl)-2,6-diaminopurine; 9-(2'-deoxy-2'-fluororibofuranosyl)-2,6-diaminopurine;

9-(arabinofuranosyl)guanine; 9-(2'-deoxyribofuranosyl) guanine; 9-(2'-deoxy 2'-fluororibofuranosyl)guanine; and a human monoclonal antibody.

15. The method of claim 14, wherein said antiviral agent is selected from the group consisting of Lamivudine, Entecavir, Coviracil, DAPD, Clevudine, AM365, L-dT, L-dC, ACH 126,443, MCC478, Lobucavir, Foscarnet, PPA, interferon alpha, and pegylated interferon alfa.

16. The method of claim 13, wherein said compound has Formula IV:

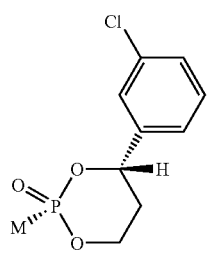

Formula IV or a pharmaceutically acceptable salt thereof;
and said antiviral agent is selected from the group consisting of Lamivudine, Entecavir, Coviracil, DAPD, Clevudine, AM365, L-dT, L-dC, ACH 126,443, MCC478, Lobucavir, Foscarnet, PPA, interferon alpha, and pegylated interferon alfa.

17. The method of claim 16, wherein said antiviral agent is selected from the group consisting of Lamivudine, Entecavir, Coviracil, DAPD, Clevudine, AM365, L-dT, L-dC, and ACH 126,443 and pharmaceutically acceptable salts thereof.

18. The method of claim 16, wherein said compound is

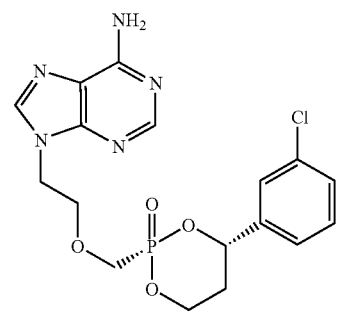

or a pharmaceutically acceptable salt thereof.

19. The method of claim 13, wherein said compound is

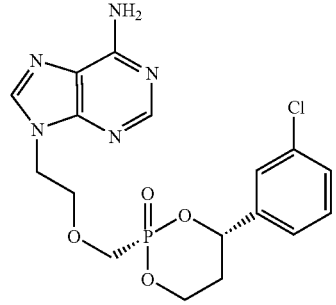

or a pharmaceutically acceptable salt thereof.

20. The method of claim 18, wherein said antiviral agent is Lamivudine, or a pharmaceutically acceptable salt thereof.

21. The method of claim 16, wherein said antiviral agent is selected from the group consisting of interferon alpha and pegylated inteferon alpha.

22. The method of claim 13, wherein said antiviral agent and said compound are administered separately.

23. The method of claim 13, wherein said antiviral agent and said compound are administered simultaneously.

24. A pharmaceutical composition comprising a pharmaceutically effective amount of the compound of claim 1 and a pharmaceutically acceptable excipient.

25. The phannaceutical composition of claim 24, wherein said compound has Formula IV:

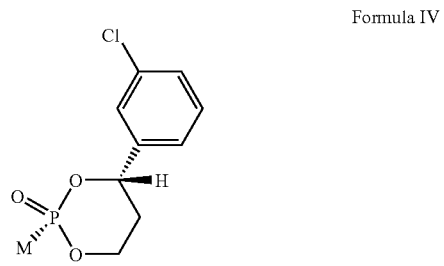

Formula IV or a pharmaceutically acceptable salt thereof.

26. The phannaceutical composition of claim 24, wherein said compound is:

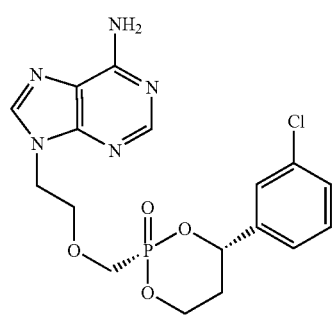

or a pharmaceutically acceptable salt thereof.

27. A pharmaceutical composition comprising a pharmaceutically effective amount of the compound of claim 1;
   a pharmaceutically effective amount of a second agent wherein said second agent is an antiviral agent or salt thereof; and
   a pharmaceutically acceptable excipient.

28. The pharmaceutical composition of claim 27, wherein said antiviral agent is selected from the group consisting of Lamivudine, Entecavir, Coviracil, DAPD, Clevudine, AM365, L-dT, L-dC, ACH 126,443, MCC478, Lobucavir, Foscarnet, PPA, interferon alpha, and pegylated interferon alfa.

29. The pharmaceutical composition of claim 27, wherein said compound has Formula IV:

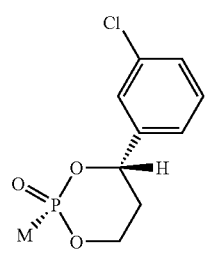

Formula IV or a pharmaceutically acceptable salt thereof.

30. The pharmaceutical composition of claim 27, wherein said compound is:

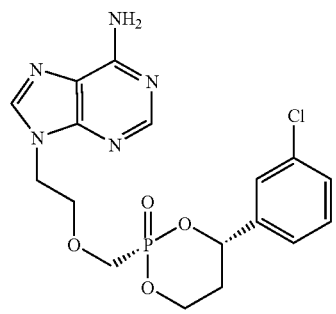

or a pharmaceutically acceptable salt thereof.

* * * * *